US012086985B2

(12) United States Patent
Khojasteh et al.

(10) Patent No.: US 12,086,985 B2
(45) Date of Patent: Sep. 10, 2024

(54) METHODS AND SYSTEMS FOR PREDICTING RESPONSE TO PD-1 AXIS DIRECTED THERAPEUTICS

(71) Applicants: Ventana Medical Systems, Inc., Tucson, AZ (US); Johns Hopkins University, Baltimore, MD (US); Memorial Sloan Kettering Cancer Center, New York, NY (US)

(72) Inventors: Mehrnoush Khojasteh, Tucson, AZ (US); Jim F. Martin, Tucson, AZ (US); Lidija Pestic-Dragovich, Tucson, AZ (US); Lei Tang, Tucson, AZ (US); Xiangxue Wang, Tucson, AZ (US); Wenjun Zhang, Tucson, AZ (US); Robert Anders, Baltimore, MD (US); Luis Diaz, New York, NY (US)

(73) Assignees: Ventana Medical Systems, Inc.; Johns Hopkins University; Memorial Sloan Kettering Cancer Center, New York, NY (US)

( * ) Notice: Subject to any disclaimer, the term of this patent is extended or adjusted under 35 U.S.C. 154(b) by 715 days.

(21) Appl. No.: 17/218,087

(22) Filed: Mar. 30, 2021

(65) Prior Publication Data
US 2021/0374962 A1 Dec. 2, 2021

Related U.S. Application Data

(60) Provisional application No. 62/742,934, filed on Oct. 9, 2018, provisional application No. 62/739,828, filed on Oct. 1, 2018.

(51) Int. Cl.
G16H 50/50 (2018.01)
C07K 16/28 (2006.01)
(Continued)

(52) U.S. Cl.
CPC ........ *G06T 7/0016* (2013.01); *C07K 16/2818* (2013.01); *G16H 10/40* (2018.01);
(Continued)

(58) Field of Classification Search
CPC ......... G06T 7/0016; G06T 2207/10056; G06T 2207/30024; G06T 2207/30096;
(Continued)

(56) References Cited

U.S. PATENT DOCUMENTS

2016/0106836 A1 4/2016 Binnig et al.
2017/0285029 A1 10/2017 Hanks et al.
(Continued)

FOREIGN PATENT DOCUMENTS

JP 2016517115 A 6/2016
WO 2017/079763 A1 5/2017
(Continued)

OTHER PUBLICATIONS

Barrera et al., "Computer-extracted features relating to spatial arrangement of tumor infiltrating lymphocytes to predict response to nivolumab in non-small cell lung cancer (NSCLC)", Journal of Clinical Oncology, May 20, 2018, ASCO Annual Meeting 2018: Abstract #: 12115.
(Continued)

*Primary Examiner* — Charlotte M Baker
(74) *Attorney, Agent, or Firm* — Roche RMS / McBee Moore & Vanik, IP, LLC

(57) ABSTRACT

A scoring functions is developed and used for identifying patients who might be responsive to a PD-1 axis directed therapy. The scoring functions are obtained by extracting features from multiplex-stained sections, selecting features that correlate with response to the therapy using a feature selection function, and fitting one or more of the selected features to a plurality of candidate scoring functions. A
(Continued)

candidate scoring function showing the desired balance between predictive sensitivity and specificity may then selected for incorporation into a scoring system that includes at least an image analysis system.

43 Claims, 29 Drawing Sheets

Specification includes a Sequence Listing.

(51) Int. Cl.
| | |
|---|---|
| *G06T 7/00* | (2017.01) |
| *G16H 10/40* | (2018.01) |
| *G16H 20/10* | (2018.01) |
| *G16H 30/20* | (2018.01) |
| *G16H 30/40* | (2018.01) |
| *G16H 50/20* | (2018.01) |
| *G16H 50/70* | (2018.01) |

(52) U.S. Cl.
CPC ............. *G16H 20/10* (2018.01); *G16H 30/20* (2018.01); *G16H 30/40* (2018.01); *G16H 50/20* (2018.01); *G16H 50/50* (2018.01); *G16H 50/70* (2018.01); *C07K 2317/24* (2013.01); *G06T 2207/10056* (2013.01); *G06T 2207/30024* (2013.01); *G06T 2207/30096* (2013.01)

(58) Field of Classification Search
CPC ............ C07K 16/2818; C07K 2317/24; G16H 10/40; G16H 20/10; G16H 30/20; G16H 30/40; G16H 50/20; G16H 50/50; G16H 50/70
USPC ........................................................ 382/128
See application file for complete search history.

(56) References Cited

U.S. PATENT DOCUMENTS

| | | | |
|---|---|---|---|
| 2018/0112277 A1* | 4/2018 | Krizman | .......... A61K 39/39558 |
| 2018/0134771 A1 | 5/2018 | Nandabalan et al. | |
| 2020/0049599 A1 | 2/2020 | Alexander et al. | |

FOREIGN PATENT DOCUMENTS

| | | |
|---|---|---|
| WO | 2017085307 A1 | 5/2017 |
| WO | 2017/096248 A1 | 6/2017 |
| WO | 2017/181073 A1 | 10/2017 |
| WO | 2018055014 A1 | 3/2018 |
| WO | 2018145023 A1 | 8/2018 |
| WO | 2018160841 A1 | 9/2018 |

OTHER PUBLICATIONS

Meyers et al., "Targeting the PD-1/PD-L1 axis for the treatment of non-small-cell lung cancer", Current Oncology, Aug. 1, 2018, pp. e324-e334, vol. 25 No. 4.
Parra, et al., "Validation of multiplex immunofluorescence panels using multispectral microscopy for immune-profiling of formalin-fixed and paraffin-embedded human tumor tissues," Scientific Reports; 7:13380 (Oct. 17, 2017).
Parra et al., "Validation of multiplex immunofluorescence panels using multispectral microscopy for immune-profiling of formalin-fixed and paraffin-embedded human tumor tissues", Scientific Reports, Oct. 17, 2017, vol. 7. No. 1.
International Search Report of International Patent Application No. PCT/US2019/053774 dated Mar. 25, 2020.
Yi et al., "Biomarkers for predicting efficacy of PD-1/PD-L1 inhibitors", Molecular Cancer, Aug. 23, 2018, 17:129.
Le et al., "PD-1 Blockade in Tumors with Mismatch-Repair Deficiency", The New England Journal of Medicine, Jun. 25, 2015, pp. 2509-2520, vol. 372.
Le et al., "Mismatch-repair deficiency predicts response of solid tumors to PD-1 blockade", Science, Jul. 28, 2017, pp. 409-413, vol. 357.
Wang, et al., "Prediction of recurrence in early stage non-small cell lung cancer using computer extracted nuclear features from digital H&E images", Scientific Reports, Oct. 19, 2017, vol. 7, 13543.
Topalian, et al., "Safety, Activity, and Immune Correlates of Anti-PD-1 Antibody in Cancer", The New England Journal of Medicine, Jul. 28, 2012, pp. 2443-2454, vol. 366 No. 26.
Zhang, et al., "Automated 5-plex fluorescent immunohistochemistry with tyramide signal amplification using antibodies from the same species", Journal for ImmunoTherapy of Cancer, Nov. 4, 2015, 3(supp 2):P111.
Zhang et al., "Abstract 5117: An automated 5-plex fluorescent immunohistochemistry enabled characterization of PD-L1 expression and tumor infiltrating immune cells in lung and bladder cancer specimens", Cancer Research, Jul. 2016, 76(14 Supp):5117.

* cited by examiner

Phenotypes
1. PD-L1+ Tumor cells (Turquoise/Green)
2. PD-L1- Tumor cells (Turquoise)
3. PD-L1+ Macrophages (Red/Green)
4. PD-L1- Macrophages (Red)
5. PD-L1+ T-cells (Magenta/Green)
6. PD-L1- T-cells (Magenta)
7. PD-L1+ Cytotoxic T-cells (Magenta/Yellow/Green)
8. PD-L1- Cytotoxic T-cells (Magenta/Yellow)

| DAPI | PanCK | PD-L1 | CD8 | CD68 | CD3 |
|---|---|---|---|---|---|
| Violet | Turquoise | Green | Yellow | Red | Magenta |

Density of PD-L1+/CD68+ cells in annotated tumor area 2.46/mm²
in epithelium tumor 0.23/mm²
in stroma area 4.88/mm²

Density of CD68+ cells in annotated tumor area 16.7/mm²

Density of PD-L1+/CD68+ cells in annotated tumor area 106.4/mm²
in epithelium tumor 100.9/mm²
in stroma area 169.9/mm²

Density of CD68+ cells in annotated tumor area 123.1/mm²

SEQUENCE LISTING

<160> NUMBER OF SEQ ID NOS: 10

<210> SEQ ID NO 1
<211> LENGTH: 182
<212> TYPE: PRT
<213> ORGANISM: Homo sapiens

<400> SEQUENCE: 1

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
```

```
                100               105               110
Ala Thr Ile Ser Gly Phe Leu Phe Ala Glu Ile Val Ser Ile Phe Val
            115                 120                 125

Leu Ala Val Gly Val Tyr Phe Ile Ala Gly Gln Asp Gly Val Arg Gln
            130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Gln Tyr Ser His Leu Gln Gly
                165                 170                 175

Asn Gln Leu Arg Arg Asn
                180

<210> SEQ ID NO 2
<211> LENGTH: 171
<212> TYPE: PRT
<213> ORGANISM: Homo sapiens

<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 3
<211> LENGTH: 207
<212> TYPE: PRT
<213> ORGANISM: Homo sapiens

<400> SEQUENCE: 3

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
```

```
                65                  70                  75                  80
His Leu Ser Leu Lys Glu Phe Ser Glu Leu Glu Gln Ser Gly Tyr Tyr
                    85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
                115                 120                 125

Ser Val Ala Thr Ile Val Ile Val Asp Ile Cys Ile Thr Gly Gly Leu
            130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
            195                 200                 205

<210> SEQ ID NO 4
<211> LENGTH: 164
<212> TYPE: PRT
<213> ORGANISM: Homo sapiens

<400> SEQUENCE: 4

Met Lys Trp Lys Ala Leu Phe Thr Ala Ala Ile Leu Gln Ala Gln Leu
1                   5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 5
<211> LENGTH: 235
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1                   5                   10                  15

His Ala Ala Arg Pro Ser Gln Phe Arg Val Ser Pro Leu Asp Arg Thr
                20                  25                  30
```

```
Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                    85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
 130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                    165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
 210                 215                 220

Gly Asp Lys Pro Ser Leu Ser Ala Arg Tyr Val
225                 230                 235

<210> SEQ ID NO 6
<211> LENGTH: 210
<212> TYPE: PRT
<213> ORGANISM: Homo sapiens

<400> SEQUENCE: 6

Met Arg Pro Arg Leu Trp Leu Leu Leu Ala Ala Gln Leu Thr Val Leu
 1               5                  10                  15

His Gly Asn Ser Val Leu Gln Gln Thr Pro Ala Tyr Ile Lys Val Gln
                20                  25                  30

Thr Asn Lys Met Val Met Leu Ser Cys Glu Ala Lys Ile Ser Leu Ser
            35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                    85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
 130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
```

```
                165                 170                 175
Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
            195                 200                 205

Tyr Lys
    210

<210> SEQ ID NO 7
<211> LENGTH: 354
<212> TYPE: PRT
<213> ORGANISM: Homo sapiens

<400> SEQUENCE: 7

Met Arg Leu Ala Val Leu Phe Ser Gly Ala Leu Leu Gly Leu Leu Ala
1               5                   10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175

Gln Ile Arg Val Met Tyr Thr Thr Gln Gly Gly Gly Glu Ala Trp Gly
            180                 185                 190

Ile Ser Val Leu Asn Pro Asn Lys Thr Lys Val Gln Gly Ser Cys Glu
        195                 200                 205

Gly Ala His Pro His Leu Leu Leu Ser Phe Pro Tyr Gly His Leu Ser
    210                 215                 220

Phe Gly Phe Met Gln Asp Leu Gln Gln Lys Val Val Tyr Leu Ser Tyr
225                 230                 235                 240

Met Ala Val Glu Tyr Asn Val Ser Phe Pro His Ala Ala Gln Trp Thr
                245                 250                 255

Phe Ser Ala Gln Asn Ala Ser Leu Arg Asp Leu Gln Ala Pro Leu Gly
            260                 265                 270

Gln Ser Phe Ser Cys Ser Asn Ser Ser Ile Ile Leu Ser Pro Ala Val
        275                 280                 285

His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320
```

```
Leu Leu Pro Leu Ile Ile Gly Leu Ile Leu Leu Gly Leu Leu Ala Leu
            325                 330                 335

Val Leu Ile Ala Phe Cys Ile Ile Arg Arg Arg Pro Ser Ala Tyr Gln
            340                 345                 350

Ala Leu

<210> SEQ ID NO 8
<211> LENGTH: 288
<212> TYPE: PRT
<213> ORGANISM: Homo sapiens

<400> SEQUENCE: 8

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 9
<211> LENGTH: 290
<212> TYPE: PRT
<213> ORGANISM: Homo sapiens

<400> SEQUENCE: 9

Met Arg Ile Phe Ala Val Phe Ile Phe Met Thr Tyr Trp His Leu Leu
```

-continued

```
1               5                   10                  15
Asn Ala Phe Thr Val Thr Val Pro Lys Asp Leu Tyr Val Val Glu Tyr
                20                  25                  30
Gly Ser Asn Met Thr Ile Glu Cys Lys Phe Pro Val Glu Lys Gln Leu
                35                  40                  45
Asp Leu Ala Ala Leu Ile Val Tyr Trp Glu Met Glu Asp Lys Asn Ile
            50                  55                  60
Ile Gln Phe Val His Gly Glu Glu Asp Leu Lys Val Gln His Ser Ser
65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
                180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
290

<210> SEQ ID NO 10
<211> LENGTH: 525
<212> TYPE: PRT
<213> ORGANISM: Homo sapiens

<400> SEQUENCE: 10

Met Trp Glu Ala Gln Phe Leu Gly Leu Leu Phe Leu Gln Pro Leu Trp
1               5                   10                  15
Val Ala Pro Val Lys Pro Leu Gln Pro Gly Ala Glu Val Pro Val Val
                20                  25                  30
Trp Ala Gln Glu Gly Ala Pro Ala Gln Leu Pro Cys Ser Pro Thr Ile
                35                  40                  45
Pro Leu Gln Asp Leu Ser Leu Leu Arg Arg Ala Gly Val Thr Trp Gln
            50                  55                  60
His Gln Pro Asp Ser Gly Pro Pro Ala Ala Ala Pro Gly His Pro Leu
65                  70                  75                  80
```

-continued

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Leu Arg Ser Gly
        100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

```
Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Pro Glu Gln Leu
            515                 520                 525
```

METHODS AND SYSTEMS FOR PREDICTING RESPONSE TO PD-1 AXIS DIRECTED THERAPEUTICS

CROSS-REFERENCE TO RELATED APPLICATIONS

This is an International Application claiming priority to U.S. Provisional Patent Application No. 62/739,828, filed Oct. 1, 2018, and to U.S. Provisional Patent Application No. 62/742,934, filed Oct. 9, 2018, the contents of each of which is incorporated herein by reference in its entirety.

SEQUENCE LISTING INCORPORATION BY REFERENCE

A Sequence Listing in the form of an ASCII-compliant text file (entitled "P34928WO_ST25") created on Sep. 18, 2019, and 23442 bytes in size) is submitted concurrently with the instant application, and the entire contents of the Sequence Listing are incorporated herein by reference.

BACKGROUND OF THE INVENTION

Field of the Invention

The invention relates to detection, characterization and enumeration of biomarkers in tumor samples useful for predicting response to checkpoint inhibitor therapy.

Description of Related Art

Cancers may escape immune surveillance and eradication through the up-regulation of the programmed death 1 (PD-1) pathway, and its ligand, programmed death-ligand 1 (PD-L1), on tumor cells and in the tumor microenvironment. Blockade of this pathway with antibodies to PD-1 or PD-L1 has led to remarkable clinical responses in some cancer patients. However, identification of predictive biomarkers for patient selection represents a major challenge.

PD-L1 is the most widely used predictive biomarker for selection of patients to receive PD-1 axis directed therapeutics. However, the results observed have been inconsistent. See Yi.

Mismatch repair (MMR) deficiency predicts response of solid tumors to PD-1 blockade. See Le (I) & Le (II). However, not all patients with mismatch repair deficiency respond to the PD-1 blockade treatment. The predictive values are limited for the variable strength of association among studies and tumor types.

Recent studies suggest spatial arrangement and interaction between cancer cells and immune cells influence patients' prognosis, survival, and response to treatment. Wang & Barrera.

There is increasing need to understand the tumor microenvironment and associated biomarkers to guide cancer immunotherapy.

BRIEF SUMMARY OF THE INVENTION

This disclosure relates generally to systems and methods of identifying and using new biomarkers predictive of a response to of a solid tumor to a PD-1 axis directed therapy.

In an embodiment, a method of developing a scoring function for predicting response of a tumor to a PD-1 axis directed therapy is disclosed, the method comprising: (a) obtaining: (a1) a set of digital images of tumor tissue samples obtained from a plurality of patients prior to treatment with the PD-1 axis directed therapy, wherein at least one digital image for each patient is a digital image of a tissue sections stained in a multiplex affinity histochemical stain for each of one or more epithelial markers, one or more immune cell markers, and one or more PD-1 axis pathway markers; and (a2) post-treatment response data for each patient; (b) extracting a plurality of features from the digital images of the multiplexed stained tissue section; (c) applying the feature selection function to the extracted plurality of features and the post-treatment response data to obtain an rank of each feature for the strength of correlation to response to the PD-1 axis directed therapy; (d) applying a modeling function to one or more of the ranked features and the post-treatment response data to generating a plurality of candidate models predictive of the response to the checkpoint inhibitor therapy and testing each candidate model for concordance with response; (e) selecting the candidate model having the highest concordance to the response as the scoring function. In an embodiment, the multiplex affinity histochemical stain comprises histochemical stain using biomarker-specific reagents for each of PD-L1, CD8, CD3, CD68 and PanCK (panel 1), and the features are selected from the group consisting of the features in Table 4, left column. In an embodiment, the multiplex affinity histochemical stain comprises histochemical stain using biomarker-specific reagents for each of PanCK, PD-L1, PD1, CD8, and LAG3 (panel 2), and the features are selected from the group consisting of the features in Table 4, right column. In an embodiment, the feature selection function is selected from the group consisting of ensemble feature selection methods (including, for example, a Random Forest function), filter methods (including, for example, Mutual information based functions, (mRMR)/correlation coefficient based functions, and Relief based functions), and/or an embedded feature selection function (such as an elastic net/least absolute shrinkage function or a selection operator (LASSO) functions). In an embodiment, candidate models are made using one or more of the top 25, top 20, top 15, top 10, top 9, top 8, top 7, top 6, top 5, top 4 or top 3 features identified by the feature selection function. In another embodiment, the candidate models use at least 1, at least 2, at least 3, at least 4, or at least 5 features identified in the top 10 features of the feature selection function. In another embodiment, the candidate models include at least one feature present in the top 5 features of at least 2 feature selection functions. In an embodiment, the modeling function is selected from the group consisting of quadrant discriminant analysis (QDA), Linear discriminant analysis (LDA), Support vector machine (SVM), and Artificial neural network (ANN). In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a method of scoring a tumor sample for likelihood of responding to a PD-1 axis directed therapy is provided, the method comprising: (a) obtaining a digital image of a tumor section from the tumor sample, wherein the tumor section is stained in a multiplex affinity histochemical stain for each of one or more epithelial markers, one or more immune cell markers, and one or more PD-1 axis pathway markers; (b) identifying a region of interest (ROI) in the digital image; (c) extracting from the ROI one or more features relating to cells stained for the respective biomarkers; and (d) applying a scoring function to a feature vector comprising the extracted feature(s) of (c) to generate a score, wherein the score is indicative of the likelihood that the tumor will respond to the PD-1 axis directed therapy. In an embodiment, the ROI is derived from a digital image of a morphologically stained section of the tumor sample, wherein the morphologically stained section and the multiplex affinity histochemical stained sample are serial sections. In an embodiment, the ROI is identified by a user in the digital image of the morphologically stained section and automatically registered to the digital image of the multiplex affinity histochemical stained section. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of the features in Table 4, left column. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be important to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be one of the top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least 1, 2, 3, 4, 5, 6, 7, 8, 9 or 10 of said top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of: Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise each of Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PanCK, PD-L1, PD1, CD8, and LAG3 (panel 2), the ROI is an ROI according to Table 3, and the features are selected from the group consisting of the features in Table 4, right column. In an embodiment, the multiplex affinity histochemical stain comprises panel 2, the ROI is an ROI according to Table 3, and the features comprise at least one feature of Table 4, right column determined to be important to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature of Table 4, right column determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least at least 1, 2, 3, 4, 5, 6, 7, 8, 9 or 10 of features of Table 4, right column, determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature selected from the group consisting of: Maximum number of CD8+/PD-1low-intensity cells within 20 µm of PD-L1+ cells in epithelial tumor, mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the multiplex affinity histochemical stain comprises panel 2, the ROI is an ROI according to Table 3, and the features comprise each of Maximum number of CD8+/PD-1low-intensity cells within 20 µm of PD-L1+ cells in epithelial tumor, mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the scoring function is derived a modeling function selected from the group consisting of quadrant discriminant analysis (QDA), Linear discriminant analysis (LDA), Support vector machine (SVM), and Artificial neural network (ANN). In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a method of selecting a patient to receive a PD-1 axis directed therapy is provided, the method comprising: (a) obtaining a digital image of a tumor section from the tumor sample, wherein the tumor section is stained in a multiplex affinity histochemical stain for each of one or more epithelial markers, one or more immune cell markers, and one or more PD-1 axis pathway markers; (b) identifying a region of interest (ROI) in the digital image; (c) extracting from the ROI one or more features relating to cells stained for the respective biomarkers; (d) applying a scoring function to a feature vector comprising the extracted feature(s) of (c) to generate a score, wherein the score is indicative of the likelihood that the tumor will respond to the PD-1 axis directed therapy; (e) comparing the score to a pre-determined cutoff value; and (f) selecting the patient to receive the PD-1 axis therapy or an alternate therapy based on the comparison of (e). In an embodiment, the ROI is derived from a digital image of a morphologically stained section of the tumor sample, wherein the morphologically stained section and the multiplex affinity histochemical stained sample are serial sections. In an embodiment, the ROI is identified by a user in the digital image of the morphologically stained section and automatically registered to the digital image of the multiplex affinity histochemical stained section. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of the features in Table 4, left column. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be important to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be one of the top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least 1, 2, 3, 4, 5, 6, 7, 8, 9 or 10 of said top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of: Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise each of Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PanCK, PD-L1, PD1, CD8, and LAG3 (panel 2), the ROI is an ROI according to Table 3, and the features are selected from the group consisting of the features in Table 4, right column. In an embodiment, the multiplex affinity histochemical stain comprises panel 2, the ROI is an ROI according to Table 3, and the features comprise at least one feature of Table 4, right column determined to be important to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature of Table 4, right column determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least at least 1, 2, 3, 4, 5, 6, 7, 8, 9 or 10 of features of Table 4, right column, determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature selected from the group consisting of: Maximum number of CD8+/PD-1low-intensity cells within 20 μm of PD-L1+ cells in epithelial tumor, mean #PD-1Low IntensityCD8+ cells within 20 μm radius of PD-L1+ cells, max value of Lag3 intensity in CD8+Lag3+ cells, average #PD-1+ cells within 20 μm radius of PD-L1+ cells, and the max value of Lag3+ intensity on CD8+ cell. In an embodiment, the multiplex affinity histochemical stain comprises panel 2, the ROI is an ROI according to Table 3, and the features comprise each of Maximum number of CD8+/PD-1low-intensity cells within 20 μm of PD-L1+ cells in epithelial tumor, mean #PD-1Low IntensityCD8+ cells within 20 μm radius of PD-L1+ cells, max value of Lag3 intensity in CD8+Lag3+ cells, average #PD-1+ cells within 20 μm radius of PD-L1+ cells, and the max value of Lag3+ intensity on CD8+ cell. In an embodiment, the scoring function is derived a modeling function selected from the group consisting of quadrant discriminant analysis (QDA), Linear discriminant analysis (LDA), Support vector machine (SVM), and Artificial neural network (ANN). In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a method of treating a patient having a tumor is provided, the method comprising: (a) obtaining a digital image of a tumor section from the tumor sample, wherein the tumor section is stained in a multiplex affinity histochemical stain for each of one or more epithelial markers, one or more immune cell markers, and one or more PD-1 axis pathway markers; (b) identifying a region of interest (ROI) in the digital image; (c) extracting from the ROI one or more features relating to cells stained for the respective biomarkers; (d) applying a scoring function to a feature vector comprising the extracted feature(s) of (c) to generate a score, wherein the score is indicative of the likelihood that the tumor will respond to the PD-1 axis directed therapy; (e) comparing the score to a pre-determined cutoff value; and (f) administering to the patient the PD-1 axis directed therapy if the comparison of (e) indicates the patient is likely to respond to the PD-1 axis directed therapy, or administering to the patient a therapeutic course that does not comprise a PD-1 axis directed therapy if the comparison of (e) indicates the patient is unlikely to respond to the PD-1 axis directed therapy. In an embodiment, the ROI is derived from a digital image of a morphologically stained section of the tumor sample, wherein the morphologically stained section and the multiplex affinity histochemical stained sample are serial sections. In an embodiment, the ROI is identified by a user in the digital image of the morphologically stained section and automatically registered to the digital image of the multiplex affinity histochemical stained section. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of the features in Table 4, left column. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be important to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature determined to be one of the top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least 1, 2, 3, 4, 5, 6, 7, 8, 9 or 10 of said top 10 most important features to prediction of a patient response to a PD-1 axis directed therapy by ReliefF and/or Random Forest. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise at least one feature selected from the group consisting of: Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PD-L1, CD8, CD3, CD68 and PanCK (panel 1), the ROI is an ROI according to Table 3, and the features comprise each of Fraction of PD-L1+ macrophages in stroma, Fraction of PD-L1+ CD3+ CD8− cells in stroma, and Fraction of PD-L1+ CD3+ cells in stroma. In an embodiment, the multiplex affinity histochemical stain comprises histochemical stain using biomarker-specific reagents for each of PanCK, PD-L1, PD1, CD8, and LAG3 (panel 2), the ROI is an ROI according to Table 3, and the features are selected from the group consisting of the features in Table 4, right column. In an embodiment, the multiplex affinity histochemical stain comprises panel 2, the ROI is an ROI according to Table 3, and the features comprise at least one feature of Table 4, right column determined to be important to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature of Table 4, right column determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least at least 1, 2, 3, 4, 5, 6, 7, 8, 9 or 10 of features of Table 4, right column, determined to be one of the top 10 most important features to prediction of a patient response to a PD-1 axis directed therapy by ReliefF and/or Random Forest. In an embodiment, the multiplex affinity histochemical stain comprises panel 2, the ROI is an ROI according to Table 3, and the features comprise at least one feature selected from the group consisting of: Maximum number of CD8+/PD-1low-intensity cells within 20 µm of PD-L1+ cells in epithelial tumor, mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the multiplex affinity histochemical stain comprises panel 2, the ROI is an ROI according to Table 3, and the features comprise each of Maximum number of CD8+/PD-1low-intensity cells within 20 µm of PD-L1+ cells in epithelial tumor, mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the scoring function is derived a modeling function selected from the group consisting of quadrant discriminant analysis (QDA), Linear discriminant analysis (LDA), Support vector machine (SVM), and Artificial neural network (ANN). In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a method is provided comprising: (a) annotating a region of interest (ROI) on a digital image of a test sample of a tumor, wherein said digital image is a digital image of a sample multiplex affinity stained for PD-L1, CD8, CD3, CD68 and PanCK (panel 1); (b) extracting from the ROI one or more features of Table 9; (c) applying a scoring function to a feature vector comprising the feature(s) of (b), wherein the output of said scoring function is a value that is predictive of a response of a patient to a PD-1 axis directed therapy. In an embodiment, the one or more features are determined to be important to prediction of a patient response to a PD-1 axis directed therapy by ReliefF and/or Random Forest. In an embodiment, the feature is determined to be one of the top 10 most important features to prediction of a patient response to a PD-1 axis directed therapy by ReliefF and/or Random Forest. In an embodiment, the at least one feature is selected from the group consisting of: Fraction of PD-L1+ macrophages in stroma, Fraction of PD-L1+CD3+ CD8− cells in stroma, and Fraction of PD-L1+ CD3+ cells in stroma. In an embodiment, the feature vector comprises each of Fraction of PD-L1+ macrophages in stroma, Fraction of PD-L1+ CD3+ CD8− cells in stroma, and Fraction of PD-L1+ CD3+ cells in stroma. In an embodiment, the feature vector comprises at least 1, 2, 3, 4, 5, 6, 7, 8, 9 or 10 of said top 10 most important features to prediction of a patient response to a PD-1 axis directed therapy by ReliefF and/or Random Forest. In an embodiment, said scoring function is derived by fitting a quadrant discriminant classifier model to the selected features to predict response to treatment. In an embodiment, the treatment outcomes used to fit the quadrant discriminant classifier model are grouped together in a configuration selected from the group consisting of PD vs. SD vs. PR+CR; PD vs. SD+PR+CR; and PD+SD vs. PR+CR. In an embodiment, the ROI is identified in a digital image of a first serial section of the test sample, wherein the first serial section is stained with hematoxylin and eosin, and wherein the ROI is automatically registered to a digital image of at least a second serial section of the test sample, wherein the second serial section is stained with panel 1. In an embodiment, the method is computer implemented. In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a method is provided comprising: (a) annotating a region of interest (ROI) on a digital image of a test sample of a tumor, wherein said digital image is a digital image of a sample multiplex affinity stained for PanCK, PD-L1, PD1, CD8, and LAG3 (panel 2); (b) extracting from the ROI one or more features of Table 16; (c) applying a scoring function to a feature vector comprising the feature(s) of (b), wherein the output of said scoring function is a value that is predictive of a response of a patient to a PD-1 axis directed therapy. In an embodiment, the one or more features are features determined to be important to prediction of a patient response to a PD-1 axis directed therapy by ReliefF and/or Random Forest. In an embodiment, the one or more features are features determined to be one of the top 10 most important features to prediction of a patient response to a PD-1 axis directed therapy by ReliefF and/or Random Forest. In an embodiment, the feature vector comprises at least one feature selected from the group consisting of "Maximum number of CD8+/PD-1low-intensity cells within 20 µm of PD-L1+ cells in epithelial tumor," mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the feature vector comprises each of Maximum number of CD8+/PD-1low-intensity cells within 20 µm of PD-L1+ cells in epithelial tumor, and optionally further comprises one or more additional features selected from the group consisting of mean #PD-1Low IntensityCD8+ cells within 20 µm radius of PD-L1+ cells, max value of Lag3 intensity in CD8+Lag3+ cells, average #PD-1+ cells within 20 µm radius of PD-L1+ cells, and the max value of Lag3+ intensity on CD8+ cell. In an embodiment, the feature vector comprises at least 1, 2, 3, 4, 5, 6, 7, 8, 9 or 10 features determined to be one of the top 10 most important features to prediction of a patient response to a PD-1 axis directed therapy by ReliefF and/or Random Forest. In an embodiment, said scoring function is derived by fitting a quadrant discriminant classifier model to the selected features to predict response to treatment. In an embodiment, the treatment outcomes used to fit the quadrant discriminant classifier model are grouped together in a configuration selected from the group consisting of: PD vs. SD vs. PR+CR; PD vs. SD+PR+CR; and PD+SD vs. PR+CR. In an embodiment, the ROI is identified in a digital image of a first serial section of the test sample, wherein the first serial section is stained with hematoxylin and eosin, and wherein the ROI is automatically registered to a digital image of at least a second serial section of the test sample, wherein the second serial section is stained with panel 2. In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a system for predicting a response of a patient to a PD-1 axis therapy is provided, the system comprising: a processor; and a memory coupled to the processor, the memory to store computer-executable instructions that, when executed by the processor, cause the processor to perform operations comprising one or more of the methods of predicting a patient response to a PD-1 directed therapy set forth in this application. In an embodiment, the system further comprises a scanner or microscope adapted to capture a digital image of a section of the tissue sample and to communicate the image to the computer apparatus. In an embodiment, the system further comprises an automated slide stainer programmed to histochemically stain a section of the tissue sample with panel 1 or panel 2. In an embodiment, the system further comprises an automated hematoxylin and eosin stainer programmed to stain one or more serial sections of the section stained by the automated slide stainer. In an embodiment, the system further comprises a laboratory information system (LIS) for tracking sample and image workflow and diagnostic information, the LIS comprising a central database configured to receive and store information related to the tissue sample, the information comprising at least one of the following: processing steps to be carried out on the tumor tissue sample, processing steps to be carried out on digital images of sections of the tumor tissue sample, processing history of the tumor tissue sample and digital images; and one or more clinical variables relevant to likelihood that the patient will respond to the therapy (such as MMR or MSI status). In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

In an embodiment, a non-transitory computer readable storage medium for storing computer-executable instructions that are executed by a processor to perform operations is provided, the operations comprising one or more of the methods of predicting a patient response to a PD-1 directed therapy set forth in this application. In an embodiment, the PD-1 axis directed therapy is a PD-1 specific monoclonal antibody or a PD-L1 specific monoclonal antibody. In an embodiment, the PD-1 axis directed therapy is selected from the group consisting of pembrolizumab, nivolumab, atezolizumab, avelumab, durvalumab, cemiplimab, tislelizumab, and LY3300054.

BRIEF DESCRIPTION OF THE DRAWINGS

This patent or application file contains at least one drawing executed in color. Copies of this patent or patent application publication with the color drawings will be provided by the Office upon request and payment of the necessary fee.

DETAILED DESCRIPTION OF THE INVENTION

I. Definitions

Figure 1:
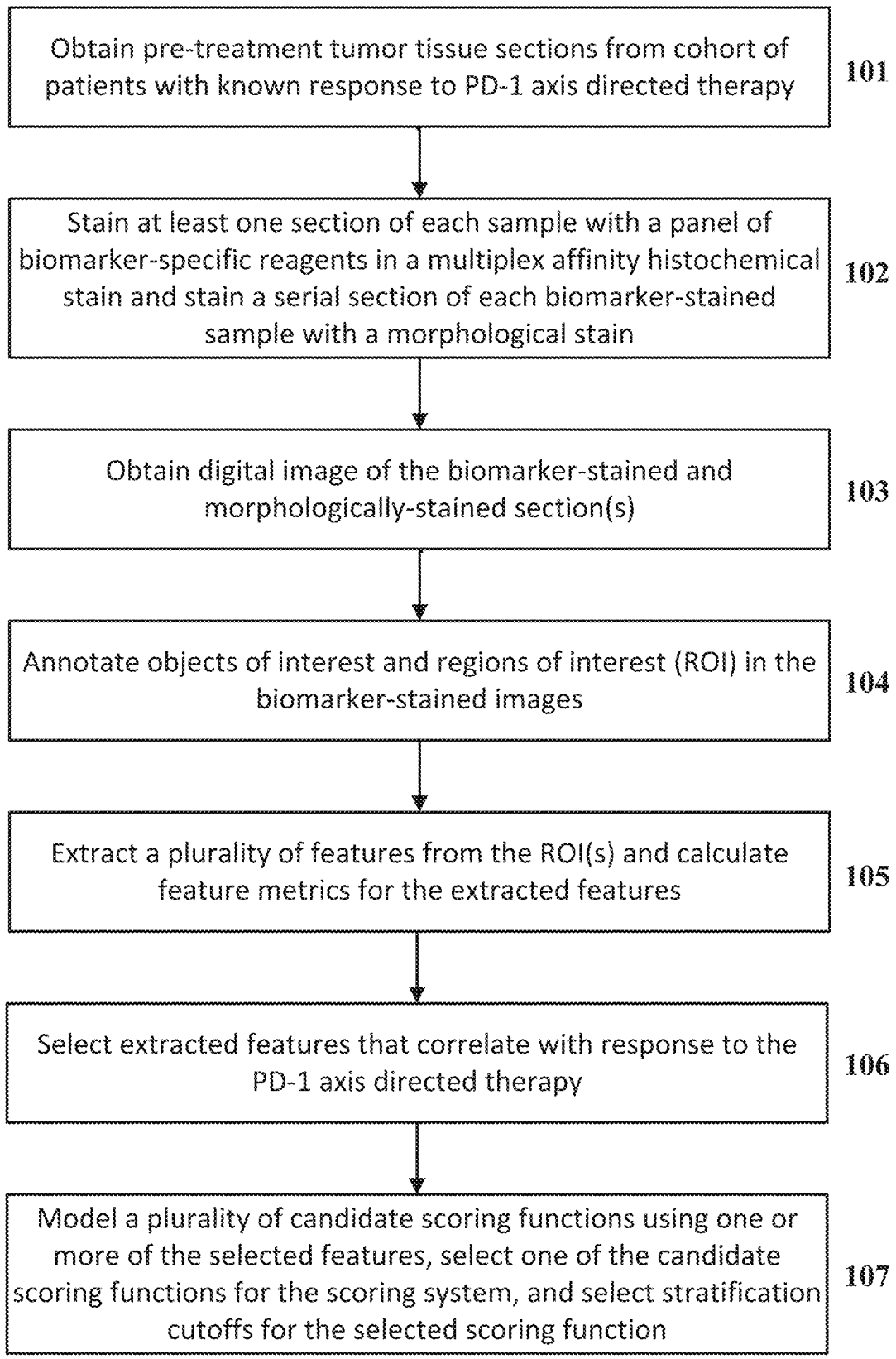
FIG. 1 is a flow chart illustrating an exemplary approach to deriving the scoring functions disclosed herein.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is characteristic of a particular cell or tissue type or state; or characteristic of a particular pathological condition or state; or indicative of the severity of a pathological condition, the likelihood of progression or regression of the pathological condition, and/or the likelihood that the pathological condition will respond to a particular treatment. As another example, the biomarker may be a cell type or a microorganism (such as a bacterium, mycobacterium, fungus, virus, and the like), or a substituent molecule or group of molecules thereof.

Biomarker-specific reagent: A specific detection reagent that is capable of specifically binding directly to one or more biomarkers in the cellular sample, such as a primary antibody.

Cellular sample: As used herein, the term "cellular sample" refers to any sample containing intact cells, such as cell cultures, bodily fluid samples or surgical specimens taken for pathological, histological, or cytological interpretation.

Detection reagent: A "detection reagent" is any reagent that is used to deposit a stain in proximity to a biomarker-specific reagent in a cellular sample. Non-limiting examples include biomarker-specific reagents (such as primary antibodies), secondary detection reagents (such as secondary antibodies capable of binding to a primary antibody), tertiary detection reagents (such as tertiary antibodies capable of binding to secondary antibodies), enzymes directly or indirectly associated with the biomarker specific reagent, chemicals reactive with such enzymes to effect deposition of a fluorescent or chromogenic stain, wash reagents used between staining steps, and the like.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultra-violet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, $11^{th}$ Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocya-nine (Cy5), and Rhodamine 110 (Rhodamine).

Feature metric: A value indicative of a level of a biomarker or a relationship between biomarkers in a sample. Examples include: expression intensity (for example, on a 0+, 1+, 2+, 3+ scale), number of cells positive for the biomarker, cell density (for example, number of biomarker-positive cells over an area of an ROI, number of biomarker-positive cells over a linear distance of an edge defining an ROI, and the like), pixel density (i.e. number of biomarker-positive pixels over an area of an ROI, number of biomarker-positive pixels over a linear distance of an edge defining an ROI, and the like), mean or median distance between cells expressing biomarker(s), etcetera. A feature metric can be a total metric or a global metric.

Histochemical detection: A process involving labelling biomarkers or other structures in a tissue sample with biomarker-specific reagents and detection reagents in a manner that permits microscopic detection of the biomarker or other structures in the context of the cross-sectional relationship between the structures of the tissue sample. Examples include immunohistochemistry (IHC), chromogenic in situ hybridization (CISH), fluorescent in situ hybridization (FISH), silver in situ hybridization (SISH), and hematoxylin and eosin (H & E) staining of formalin-fixed, paraffin-embedded tissue sections.

Immune checkpoint molecule: A protein expressed by an immune cell whose activation down-regulates a cytotoxic T-cell response. Examples include PD-1, TIM-3, LAG-4, and CTLA-4.

Immune escape biomarker: A biomarker expressed by a tumor cell that helps the tumor avoid a T-cell mediated immune response. Examples of immune escape biomarkers include PD-L1, PD-L2, and IDO.

Immunological biomarker: A biomarker that is characteristic of or impacts upon an immune response to an abnormal cell, including but not limited to biomarkers that: are indicative of a particular class of immune cell (such as a CD3), characterize an immune response (such as the presence, absence, or amount of cytokine proteins or particular immune cell subtype(s)), or that are expressed by, presented by, or otherwise located on non-immune cell structure that affect the type or extent of responses of immune cell (such as cell surface expressed antigens, MHC-ligand complexes, and immune escape biomarkers).

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

Multiplex histochemical stain: A histochemical staining method in which multiple biomarker-specific reagents that bind to different biomarkers are applied to a single section and stained with different color stains.

PD-1 axis directed therapy: A therapeutic agent that disrupts the ability of PD-1 to down-regulate T-cell activity. Exemplary the PD-1 axis directed therapy include PD-1 specific monoclonal antibodies (e.g. pembrolizumab, nivolumab, cemiplimab, and tislelizumab), PD-L1 specific monoclonal antibodies (e.g. atezolizumab, avelumab, durvalumab, and LY3300054), and PD-1 small molecule inhibitors (e.g. CA-170, others in pre-clinical development reviewed by Li & Tian).

Sample: As used herein, the term "sample" shall refer to any material obtained from a subject capable of being tested for the presence or absence of a biomarker.

Secondary detection reagent: A specific detection reagent capable of specifically binding to a biomarker-specific reagent.

Section: When used as a noun, a thin slice of a tissue sample suitable for microscopic analysis, typically cut using a microtome. When used as a verb, the process of generating a section.

Serial section: As used herein, the term "serial section" shall refer to any one of a series of sections cut in sequence by a microtome from a tissue sample. For two sections to be considered "serial sections" of one another, they do not necessarily need to be consecutive sections from the tissue, but they should generally contain sufficiently similar tissue structures in the same spatial relationship, such that the structures can be matched to one another after histological staining.

Simplex histochemical stain: A histochemical staining method in which a single biomarker-specific reagent is applied to a single section and stained with a single color stain.

Specific detection reagent: Any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of ≤1 µM, ≤100 nM, ≤10 nM, ≤1 nM, or ≤0.1 nM. In another embodiment, specific binding can include, but does not require exclusive binding. Exemplary specific detection reagents include nucleic acid probes specific for particular nucleotide sequences; antibodies and antigen binding fragments thereof; and engineered specific binding compositions, including ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor, Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zurich, CH), ANTICALINs (scaffold based on lipocalins; Pieris AG, Freising, DE), NANOBODYs (scaffold based on VHH (camelid Ig); Ablynx N/V, Ghent, BE), TRANS-BODYs (scaffold based on Transferrin; Pfizer Inc., New York, NY), SMIPs (Emergent Biosolutions, Inc., Rockville, MD), and TETRANECTINs (scaffold based on C-type lectin domain (CTLD), tetranectin; Borean Pharma A/S, Aarhus, DK). Descriptions of such engineered specific binding structures are reviewed by Wurch et al., *Development of Novel Protein Scaffolds as Alternatives to Whole Antibodies for Imaging and Therapy: Status on Discovery Research and Clinical Validation*, Current Pharmaceutical Biotechnology, Vol. 9, pp. 502-509 (2008), the content of which is incorporated by reference.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

Test sample: A tumor sample obtained from a subject having an unknown outcome at the time the sample is obtained.

Tissue sample: As used herein, the term "tissue sample" shall refer to a cellular sample that preserves the cross-sectional spatial relationship between the cells as they existed within the subject from which the sample was obtained.

Tumor sample: A tissue sample obtained from a tumor.

II. Biomarker Descriptions

CD3: CD3 is a cell surface receptor complex that is frequently used as a defining biomarker for cells having a T-cell lineage. The CD3 complex is composed of 4 distinct polypeptide chains: CD3-gamma chain, CD3-delta chain, CD3epsilon chain, and CD3-zeta chain. CD3-gamma and CD3-delta each form heterodimers with CD3-epsilon (εγ-homodimer and εδ-heterodimer) while CD3-zeta forms a homodimer (ζζ-homodimer). Functionally, the εγ-homodimer, εδ-heterodimer, and ζζ-homodimer form a signaling complex with T-cell receptor complexes. Exemplary sequences for (and isoforms and variants of) the human CD3-gamma chain, CD3-delta chain, CD3epsilon chain, and CD3-zeta chain can be found at Uniprot Accession Nos. P09693 (the canonical amino acid sequence for which is disclosed herein at SEQ ID NO: 1), P04234 (the canonical amino acid sequence for which is disclosed herein at SEQ ID NO: 2), P07766 (the canonical amino acid sequence for which is disclosed herein at SEQ ID NO: 3), and P20963 (the canonical amino acid sequence for which is disclosed herein at SEQ ID NO: 4), respectively. As used herein, the term "human CD3 protein biomarker" encompasses any CD3-gamma chain, CD3-delta chain, CD3epsilon chain, and CD3-zeta chain polypeptide having a canonical human sequence and natural variants thereof that maintain the function of the canonical sequence; εγ-homodimers, εδ-heterodimers, and ζζ-homodimers including one of more of CD3-gamma chain, CD3-delta chain, CD3epsilon chain, and CD3-zeta chain polypeptide having a canonical human sequence and natural variants thereof that maintain the function of the canonical sequence; and any signaling complex including one or more of the foregoing CD3 homodimers or heterodimers. In some embodiments, a human CD3 protein biomarker-specific agent encompasses any biomarker-specific agent that specifically binds a structure (such as an epitope) within CD3-gamma chain polypeptide (such as the polypeptide at SEQ ID NO: 1), CD3-delta chain polypeptide (such as the polypeptide at SEQ ID NO: 2), CD3epsilon chain polypeptide (such as the polypeptide at SEQ ID NO: 3), or CD3-zeta chain polypeptide (such as the polypeptide at SEQ ID NO: 4), or that binds to a structure (such as an epitope) located within εγ-homodimer, εδ-heterodimer, or ζζ-homodimer.

CD8: CD8 is a heterodimeric, disulphide linked, transmembrane glycoprotein found on the cytotoxic-suppressor T cell subset, on thymocytes, on certain natural killer cells, and in a subpopulation of bone marrow cells. Exemplary sequences for (and isoforms and variants of) the human alpha- and beta-chain of the CD8 receptor can be found at Uniprot Accession Nos. P01732 (the canonical amino acid sequence for which is disclosed herein at SEQ ID NO: 5) and P10966 (the canonical amino acid sequence for which is disclosed herein at SEQ ID NO: 6), respectively. As used herein, the term "human CD8 protein biomarker" encompasses any CD8-alpha chain polypeptide having a canonical human sequence and natural variants thereof that maintain the function of the canonical sequence; any CD8-beta chain polypeptide having a canonical human sequence and natural variants thereof that maintain the function of the canonical sequence; any dimers including a CD8-alpha chain polypeptide having a canonical human sequence and natural variants thereof that maintain the function of the canonical sequence and/or a CD8-beta chain polypeptide having a canonical human sequence and natural variants thereof that maintain the function of the canonical sequence. In some embodiments, a human CD8 protein biomarker-specific agent encompasses any biomarker-specific agent that specifically binds a structure (such as an epitope) within CD8-alpha chain polypeptide (such as the polypeptide at SEQ ID NO: 5), CD8-beta chain polypeptide (such as the polypeptide at SEQ ID NO: 6), or that binds to a structure (such as an epitope) located within a CD8 dimer.

CD68: CD68 is a glycoprotein encoded by the CD68 gene located on chromosome 17 at location 17p13.1. CD68 protein is found in the cytoplasmic granules of a variety of different blood cells and myocytes, and is frequently used as a biomarker for cells of macrophage lineage, including monocytes, histiocytes, giant cells, Kupffer cells, and osteoclasts. Exemplary sequences for (and isoforms and variants of) human CD68 can be found at Uniprot Accession No. P34810 (the canonical amino acid sequence for which is disclosed herein at SEQ ID NO: 7). As used herein, the term "human CD68 protein biomarker" encompasses any CD68 polypeptide having a canonical human sequence and natural variants thereof that maintain the function of the canonical sequence. In some embodiments, a human CD20 protein biomarker-specific agent encompasses any biomarker-specific agent that specifically binds a structure (such as an epitope) within a human CD68 polypeptide (such as the polypeptide at SEQ ID NO: 7).

Pancytokeratin: As used herein, "pancytokeratin" and "PanCK" refer to any biomarker-specific reagent or group of biomarker-specific reagents that specifically bind to a sufficient plurality of cytokeratins to specifically stain epithelial tissue in a tissue sample. Exemplary pancytokeratin biomarker-specific reagents typically include either: (a) a single cytokeratin-specific reagent that recognizes an epitope common to the plurality of cytokeratins, wherein most epithelial cells of the tissue express at least one of the plurality of cytokeratins; or (b) a cocktail of a biomarker-specific reagents such that the cocktail is specifically reactive with a plurality of cytokeratins, wherein most epithelial cells of the tissue express at least one of the plurality of cytokeratins. Reference to a "cocktail" in this definition includes both a single composition comprising each member of the plurality, or providing each member of the plurality as separate compositions, but staining them with a single dye, or combinations thereof. PanCK cocktails are reviewed by NordiQC. In some embodiments, the PanCK biomarker-specific reagent includes antibody cocktails containing two or more of antibody clones selected from the group consisting of 5D3, LP34, AE1, AE2, AE3, MNF116, and PCK-26. In an embodiment, a PanCK cocktail is selected from the group consisting of: a cocktail of AE1 & AE3, a cocktail of AE1, AE3, and 5D3, and a cocktail of AE1, AE3, and PCK26. Cocktails of AE1 & AE3 are commercially available from Agilent Technologies (Cat. Nos. GA05361-2, IS05330-2, IR05361-2, M351501-2 and M351529-2). Cocktails of AE1, AE3, and 5D3 are commercially available from BioCare (Cat. Nos. CM162, IP162, OAI162, and PM162) and Abcam (Cat. No. ab86734). Cocktails of AE1, AE3, and PCK26 are available from Roche (Cat. No. 760-2135).

PD-1: Programmed death-1 (PD-1) is a member of the CD28 family of receptors encoded by the PDCD1 gene on chromosome 2. Exemplary sequences for (and isoforms and variants of) the human PD-1 protein can be found at Uniprot Accession No. Q15116 (the canonical amino acid sequence for which is disclosed herein at SEQ ID NO: 8). In some embodiments, a human PD-1 protein biomarker-specific agent encompasses any biomarker-specific agent that specifically binds a structure (such as an epitope) within a human PD-1 polypeptide (such as the polypeptide at SEQ ID NO: 8).

PD-L1: Programmed death ligand 1 (PD-L1) is a type 1 transmembrane protein encoded by the CD274 gene on chromosome 9. PD-L1 acts as a ligand for PD-1 and CD80. Exemplary sequences for (and isoforms and variants of) the human PD-L1 protein can be found at Uniprot Accession No. Q9NZQ7 (the canonical amino acid sequence for which is disclosed herein at SEQ ID NO: 9). In some embodiments, a human PD-L1 protein biomarker-specific agent encompasses any biomarker-specific agent that specifically binds a structure (such as an epitope) within a human PD-L1 polypeptide (such as the polypeptide at SEQ ID NO: 9).

LAG3: Lymphocyte activation gene 3 protein (LAG3) is a member of the immunoglobulin (Ig) superfamily encoded by the LAG3 gene on human chromosome 12. Exemplary sequences for (and isoforms and variants of) the human LAG3 protein can be found at Uniprot Accession No. P18627 (the canonical amino acid sequence for which is disclosed herein at SEQ ID NO: 10). In some embodiments, a human LAG3 protein biomarker-specific agent encompasses any biomarker-specific agent that specifically binds a structure (such as an epitope) within a human LAG3 polypeptide (such as the polypeptide at SEQ ID NO: 10).

III. Generation of Scoring Functions

FIG. 1 is a flow chart illustrating an exemplary approach to deriving the scoring functions disclosed herein. The scoring functions of the present methods and systems are generally derived from tumor samples obtained from a cohort of patients prior to treatment with a PD-1 axis directed therapy and for whom outcome data is available (such as 3 or 5 year overall survival, progression free survival, recurrence free survival, progressive disease, stable disease, partial response, complete response, and the like) 101. A panel of biomarkers to test is selected, the samples of the cohort are stained for the biomarkers 102 and imaged (often along with a morphologically-stained serial section) 103. Regions of interest (ROIs) are identified in the digital image(s) 104 and a plurality of biomarker features are extracted from the ROI(s) 105. The extracted features are evaluated by a feature selection function to identify those features that correlate with response to the PD-1 axis by using a feature selection function 106. The one or more of the selected features are modeled against the outcomes using a one or more modeling functions, a candidate scoring function is identified, and one or more cutoffs optionally are selected to separate the cohort into groups according to their score (for example "likely to respond" and "unlikely to respond" groups or "high likelihood of response" and "low likelihood of response"), for example by using ROC curves, and the cutoffs are tested using Kaplan-Meier curves comparing the groups 107. The scoring function and cutoff combination showing the desired separation between groups is then selected for inclusion in a scoring system and methods as described herein.

III.A. Samples and Sample Preparation for Generation of the Scoring Function The scoring function is typically modeled on tissue sections obtained from a cohort of subjects having a tumor and known response to the PD-1 axis directed therapy 101. In some embodiments, the tumor is a solid tumor, such as a carcinoma, lymphoma, or sarcoma. In an embodiment, the tumor is a tumor of the skin, breast, head and/or neck, lung, upper gastrointestinal tract (including the esophagus and stomach), female reproductive system (including uterine, fallopian, and ovarian tumors), lower gastrointestinal tract (including the colon, rectal, and anal tumors), urogenital tract, exocrine, endocrine, renal, neural, or of lymphocytic origin. In an embodiment, subject has a melanoma, breast cancer, ovarian cancer, pancreatic cancer, head and neck cancer, lung cancer, esophageal cancer, gastric cancer, colorectal cancer (including cancer of the colon, rectum, and anus), prostate, urothelial cancer, or lymphoma. In specific embodiments, the tumor is a non-small cell lung carcinoma, squamous cell carcinoma of the head and neck, Hodgkin Lymphoma, urothelial carcinoma, gastric cancer, renal cell carcinoma, hepatocellular carcinoma, or a colorectal cancer.

The samples obtained 101 are typically tissue samples processed in a manner compatible with histochemical staining, including, for example, fixation, embedding in a wax matrix (such as paraffin), and sectioning (such as with a microtome). No specific processing step is required by the present disclosure, so long as the sample obtained is compatible with histochemical staining of the sample for the biomarkers of interest and generating a digital image of the stained sample. In a specific embodiment, the scoring function is modeled using microtome sections of formalin-fixed, paraffin-embedded (FFPE) samples. Additionally, for generation of the scoring function, the samples of the cohort 101 should be samples with a known outcome, such as recurrence of disease, progression of disease, death from disease, overall death, progressive disease, stable disease, partial response, and/or complete response.

III.B. Biomarker Panels

When generating the scoring function, at least one section of the sample is stained with a panel of biomarker-specific reagents 102. The panels typically include at least one epithelial marker-specific reagent (such as a Pan-CK-specific reagent), at least one immune cell-specific reagent (such as CD3-, CD8-, and/or CD68-specific reagents), and at least one PD-1 axis biomarker-specific reagent (such as a PD-1-, PD-L1-, and/or PD-L2-specific reagents). In some embodiments, the panel may further comprise one or more additional immune checkpoint biomarker-specific reagents, such as a LAG3-specific reagent. In an embodiment, the biomarker-specific reagent panel is selected from the group consisting of: panel 1, comprising CD8, an epithelial marker (EM-), CD68, CD3, and PD-L1; and panel 2, comprising CD8, an epithelial marker (EM-), PD-L1, PD-1, and LAG3. Examples of epithelial markers useful in Panels 1 and 2 include cytokeratins. In an embodiment, the epithelial marker is a set of cytokeratins stained by a PanCK biomarker-specific reagent.

The panels of biomarker-specific reagents re used in combination with a set of appropriate detection reagents to generate a biomarker-stained section. Biomarker staining is typically accomplished by contacting a section of the sample with a biomarker-specific reagent under conditions that facilitate specific binding between the biomarker and the biomarker-specific reagent. The sample is then contacted with a set of detection reagents that interact with the biomarker-specific reagent to facilitate deposition a detectable moiety in close proximity the biomarker, thereby generating a detectable signal localized to the biomarker. Typically, wash steps are performed between application of different reagents to prevent unwanted non-specific staining of tissues. Biomarker-stained sections may optionally be additionally stained with a contrast agent (such as a hematoxylin stain) to visualize macromolecular structures. Additionally, a serial section of the biomarker-stained section may be stained with a morphological stain to facilitate ROI identification.

III.C.1. Labeling Schemes and Associated Reagents

The biomarker-specific reagent facilitates detection of the biomarker by mediating deposition of a detectable moiety in close proximity to the biomarker-specific reagent.

In some embodiments, the detectable moiety is directly conjugated to the biomarker-specific reagent, and thus is deposited on the sample upon binding of the biomarker-specific reagent to its target (generally referred to as a direct labeling method). Direct labeling methods are often more directly quantifiable, but often suffer from a lack of sensitivity. In other embodiments, deposition of the detectable moiety is effected by the use of a detection reagent associated with the biomarker-specific reagent (generally referred to as an indirect labeling method). Indirect labeling methods have the increase the number of detectable moieties that can be deposited in proximity to the biomarker-specific reagent, and thus are often more sensitive than direct labeling methods, particularly when used in combination with dyes.

In some embodiments, an indirect method is used, wherein the detectable moiety is deposited via an enzymatic reaction localized to the biomarker-specific reagent. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:
(a) a specific detection reagent; and
(b) an enzyme conjugated to the specific detection reagent, wherein the enzyme is reactive with the chromogenic substrate, signaling conjugate, or enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate](ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indodicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of biomarker-specific reagent and detection reagent combinations are set forth in Table 1 are specifically included.

TABLE 1

A. Biomarker-specific reagent linked directly to detectable moiety

Biomarker-specific reagent-Dye conjugate
B. Biomarker-specific reagent linked to enzyme reacting with detectable moiety Biomarker-specific reagent-Enzyme conjugate + DAB
Biomarker-specific reagent-Enzyme conjugate + Chromogen
C. Biomarker-specific reagent linked to Enzyme reacting with detectable moiety

| | |
|---|---|
| C1. Signaling conjugate comprises detectable moiety | Biomarker-specific reagent-Enzyme conjugate + QM-Dye conjugate |
| | Biomarker-specific reagent-Enzyme conjugate + Tyramide-Dye conjugate |
| C2. Signaling conjugate comprises enzyme that reacts directly with detectable moiety | Biomarker-specific reagent-Enzyme conjugate + QM-Enzyme conjugate + DAB |
| | Biomarker-specific reagent-Enzyme conjugate + QM-Enzyme conjugate + Chromogen |
| | Biomarker-specific reagent-Enzyme conjugate + Tyramide-Enzyme conjugate + DAB |
| | Biomarker-specific reagent-Enzyme conjugate + Tyramide-Enzyme conjugate + Chromogen |
| C3. Signaling conjugate comprises enzyme that reacts with second signaling conjugate comprising detectable moiety | Biomarker-specific reagent-Enzyme conjugate + QM-Enzyme conjugate + QM-Dye conjugate |
| | Biomarker-specific reagent-Enzyme conjugate + QM-Enzyme conjugate + Tyramide-Dye conjugate |
| | Biomarker-specific reagent-Enzyme conjugate + Tyramide-Enzyme conjugate + QM-Dye conjugate |
| | Biomarker-specific reagent-Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent-Enzyme conjugate + Tyramide-(biotin/hapten) conjugate + Dye-(avidin/anti-hapten biomarker-specific reagent) conjugate |
| | Biomarker-specific reagent-Enzyme conjugate + QM-(biotin/hapten) conjugate + Dye-(avidin/anti-hapten biomarker-specific reagent) conjugate |
| C5. Signaling conjugate comprises member of a specific binding pair and other member of binding pair is linked to enzyme reactive with detectable moiety | Biomarker-specific reagent-Enzyme conjugate + QM-(biotin/hapten) conjugate + Enzyme-(avidin/anti-hapten biomarker-specific reagent) conjugate + DAB |
| | Biomarker-specific reagent-Enzyme conjugate + QM-(biotin/hapten) conjugate + Enzyme-(avidin/anti-hapten biomarker-specific reagent) conjugate + Chromogen |
| | Biomarker-specific reagent-Enzyme conjugate + Tyramide-(biotin/hapten) conjugate + Enzyme-(avidin/anti-hapten biomarker-specific reagent) conjugate + DAB |
| | Biomarker-specific reagent-Enzyme conjugate + Tyramide-(biotin/hapten) conjugate + Enzyme-(avidin/anti-hapten biomarker-specific reagent) conjugate + Chromogen |

TABLE 1-continued

| | |
|---|---|
| C6. Signaling conjugate comprises member of a specific binding pair and other member of binding pair is linked to enzyme reactive with second detectable moiety linked to a detectable moiety | Biomarker-specific reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent-Enzyme conjugate + QM-(biotin/hapten) conjugate + Enzyme-(avidin/anti-hapten biomarker-specific reagent) conjugate + QM-Dye conjugate<br>Biomarker-specific reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent-Enzyme conjugate + Tyramide-(biotin/hapten) conjugate + Enzyme-(avidin/anti-hapten biomarker-specific reagent) conjugate + QM-Dye conjugate |
| D. Biomarker-specific reagent linked to member of specific binding pair | |
| D1. Dye linked to other member of specific binding pair | Biomarker-specific reagent-(biotin/hapten) conjugate + Dye-(avidin/anti-hapten biomarker-specific reagent) conjugate |
| D2. Enzyme linked to other member of specific binding pair, wherein the enzyme is reactive with detectable moiety | Biomarker-specific reagent-(biotin/hapten) conjugate + Enzyme-(avidin/anti-hapten biomarker-specific reagent) conjugate + DAB<br>Biomarker-specific reagent-(biotin/hapten) conjugate + Enzyme-(avidin/anti-hapten biomarker-specific reagent) conjugate + Chromogen<br>Biomarker-specific reagent-(biotin/hapten) conjugate + Enzyme-(avidin/anti-hapten biomarker-specific reagent) conjugate + QM-Dye conjugate<br>Biomarker-specific reagent-(biotin/hapten) conjugate + Enzyme-(avidin/anti-hapten biomarker-specific reagent) conjugate + Tyramide-Dye conjugate |
| E. Secondary detection reagent linked directly to detectable moiety | |
| Biomarker-specific reagent + 2° specific detection reagent-Dye conjugate | |
| F. Secondary detection reagent linked to Enzyme reacting with detectable moiety | |
| Biomarker-specific reagent + 2° specific detection reagent-Enzyme conjugate + DAB<br>Biomarker-specific reagent + 2° specific detection reagent-Enzyme conjugate + Chromogen | |
| G. Secondary detection reagent linked to Enzyme reacting with detectable moiety | |
| G1. Signaling conjugate comprises detectable moiety | Biomarker-specific reagent + 2° specific detection reagent-Enzyme conjugate + QM-Dye conjugate<br>Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB<br>Biomarker-specific reagent + 2° specific detection reagent-Enzyme conjugate + QM-Enzyme conjugate + Chromogen<br>Biomarker-specific reagent + 2° specific detection reagent-Enzyme conjugate + Tyramide-Enzyme conjugate + DAB<br>Biomarker-specific reagent + 2° specific detection reagent-Enzyme conjugate + Tyramide-Enzyme conjugate + Chromogen |
| G3. Signaling conjugate comprises enzyme that reacts with second signaling conjugate comprising detectable moiety | Biomarker-specific reagent + 2° specific detection reagent-Enzyme conjugate + QM-Enzyme conjugate + QM-Dye conjugate<br>Biomarker-specific reagent + 2° specific detection reagent-Enzyme conjugate + QM-Enzyme conjugate + Tyramide-Dye conjugate<br>Biomarker-specific reagent + 2° specific detection reagent-Enzyme conjugate + Tyramide-Enzyme conjugate + QM-Dye conjugate<br>Biomarker-specific reagent + 2° specific detection reagent-Enzyme conjugate + Tyramide-Enzyme conjugate + Tyramide-Dye conjugate |
| G4. Signaling conjugate comprises member of a specific binding pair and other member of binding pair is linked to detectable moiety | Biomarker-specific reagent + 2° specific detection reagent-Enzyme conjugate + Tyramide-(biotin/hapten) conjugate + Dye-(avidin/anti-hapten biomarker-specific reagent) conjugate<br>Biomarker-specific reagent + 2° specific detection reagent-Enzyme conjugate + QM-(biotin/hapten) conjugate + Dye-(avidin/anti-hapten biomarker-specific reagent) conjugate |

TABLE 1-continued

| | |
|---|---|
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + DAB<br>Biomarker-specific reagent + 2° specific detection reagent-Enzyme conjugate + QM-(biotin/hapten) conjugate + Enzyme-(avidin/anti-hapten biomarker-specific reagent) conjugate + Chromogen<br>Biomarker-specific reagent + 2° specific detection reagent-Enzyme conjugate + Tyramide-(biotin/hapten) conjugate + Enzyme-(avidin/anti-hapten biomarker-specific reagent) conjugate + DAB<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Chromogen |
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + QM-(biotin/hapten) conjugate + Enzyme-(avidin/anti-hapten biomarker-specific reagent) conjugate + QM-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + QM-Dye conjugate |
| H. Secondary detection reagent linked to member of specific binding pair | |
| H1. Dye linked to other member of specific binding pair | Biomarker-specific reagent + 2° specific detection reagent-(biotin/hapten) conjugate + Dye-(avidin/anti-hapten biomarker-specific reagent) conjugate |
| H2. Enzyme linked to other member of specific binding pair, wherein the enzyme is reactive with detectable moiety | Biomarker-specific reagent + 2° specific detection reagent-(biotin/hapten) conjugate + Enzyme-(avidin/anti-hapten biomarker-specific reagent) conjugate + DAB<br>Biomarker-specific reagent + 2° specific detection reagent-(biotin/hapten) conjugate + Enzyme-(avidin/anti-hapten biomarker-specific reagent) conjugate + Chromogen<br>Biomarker-specific reagent + 2° specific detection reagent-(biotin/hapten) conjugate + Enzyme-(avidin/anti-hapten biomarker-specific reagent) conjugate + QM-Dye conjugate<br>Biomarker-specific reagent + 2° specific detection reagent-(biotin/hapten) conjugate + Enzyme-(avidin/anti-hapten biomarker-specific reagent) conjugate + Tyramide-Dye conjugate |
| I. Tertiary specific detection reagent linked directly to detectable moiety | |
| | Biomarker-specific reagent + 2° specific detection reagent + 3° specific detection reagent-Dye conjugate |
| J. Tertiary specific detection reagent linked to Enzyme reacting with detectable moiety | |
| | Biomarker-specific reagent + 2° specific detection reagent + 3° specific detection reagent-Enzyme conjugate + DAB<br>Biomarker-specific reagent + 2° specific detection reagent + 3° specific detection reagent-Enzyme conjugate + Chromogen |
| K. Tertiary specific detection reagent linked to Enzyme reacting with detectable moiety | |
| K1. Signaling conjugate comprises detectable moiety | Biomarker-specific reagent + 2° specific detection reagent + 3° specific detection reagent-Enzyme conjugate + QM-Dye conjugate<br>Biomarker-specific reagent + 2° specific detection reagent + 3° specific detection reagent-Enzyme conjugate + Tyramide-Dye conjugate |
| K2. Signaling conjugate comprises enzyme that reacts directly with detectable moiety | Biomarker-specific reagent + 2° specific detection reagent + 3° specific detection reagent-Enzyme conjugate + QM-Enzyme conjugate + DAB<br>Biomarker-specific reagent + 2° specific detection reagent + 3° specific detection reagent-Enzyme conjugate + QM-Enzyme conjugate + Chromogen |

TABLE 1-continued

| | |
|---|---|
| | Biomarker-specific reagent + 2° specific detection reagent + 3° specific detection reagent-Enzyme conjugate + Tyramide-Enzyme conjugate + DAB |
| | Biomarker-specific reagent + 2° specific detection reagent + 3° specific detection reagent-Enzyme conjugate + Tyramide-Enzyme conjugate + Chromogen |
| K3. Signaling conjugate comprises enzyme that reacts with second signaling conjugate comprising detectable moiety | Biomarker-specific reagent + 2° specific detection reagent + 3° specific detection reagent-Enzyme conjugate + QM-Enzyme conjugate + QM-Dye conjugate |
| | Biomarker-specific reagent + 2° specific detection reagent + 3° specific detection reagent-Enzyme conjugate + QM-Enzyme conjugate + Tyramide-Dye conjugate |
| | Biomarker-specific reagent + 2° specific detection reagent + 3° specific detection reagent-Enzyme conjugate + Tyramide-Enzyme conjugate + QM-Dye conjugate |
| | Biomarker-specific reagent + 2° specific detection reagent + 3° specific detection reagent-Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent-Enzyme conjugate + Tyramide-(biotin/hapten) conjugate + Dye-(avidin/anti-hapten biomarker-specific reagent) conjugate |
| | Biomarker-specific reagent + 2° specific detection reagent + 3° specific detection reagent-Enzyme conjugate + QM-(biotin/hapten) conjugate + Dye-(avidin/anti-hapten biomarker-specific reagent) conjugate |
| K5. Signaling conjugate comprises member of a specific binding pair and other member of binding pair is linked to enzyme reactive with detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + DAB |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + DAB |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Chromogen |
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin/hapten) conjugate + Dye-(avidin/anti-hapten biomarker-specific reagent) conjugate |
| L2. Enzyme linked to other member of specific binding pair, wherein the enzyme is reactive with detectable moiety | Biomarker-specific reagent + 2° specific detection reagent + 3° specific detection reagent-(biotin/hapten) conjugate + Enzyme-(avidin/anti-hapten biomarker-specific reagent) conjugate + DAB |
| | Biomarker-specific reagent + 2° specific detection reagent + 3° specific detection reagent-(biotin/hapten) |

TABLE 1-continued conjugate + Enzyme-(avidin/anti-hapten biomarker-specific reagent) conjugate + Chromogen
Biomarker-specific reagent + 2° specific detection reagent + 3° specific detection reagent-(biotin/hapten) conjugate + Enzyme-(avidin/anti-hapten biomarker-specific reagent) conjugate + QM-Dye conjugate
Biomarker-specific reagent + 2° specific detection reagent + 3° specific detection reagent-(biotin/hapten) conjugate + Enzyme-(avidin/anti-hapten biomarker-specific reagent) conjugate + Tyramide-Dye conjugate In a specific embodiment, the biomarker-specific reagents and the specific detection reagents set forth in Table 1 are antibodies. As would be appreciated by a person having ordinary skill in the art, the detection scheme for each of the biomarker-specific reagent may be the same, or it may be different.

Non-limiting examples of commercially available detection reagents or kits comprising detection reagents suitable for use with present methods include: VENTANA ultraView detection systems (secondary antibodies conjugated to enzymes, including HRP and AP); VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Arizona); PowerVision and PowerVision+ IHC Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

III.C.2. Multiplex Labeling Schemes

In an embodiment, the biomarker-specific reagents and detection reagents are applied in a multiplex staining method. In multiplex methods, the biomarker-specific reagents and detection reagents are applied in a manner that allows the different biomarkers to be differentially labeled.

One way to accomplish differential labelling of different biomarkers is to select combinations of biomarker-specific reagents, detection reagents, and enzyme combinations that will not result in off-target cross-reactivity between different antibodies or detection reagents (termed "combination staining"). For example, where secondary detection reagents are used, each secondary detection reagent is capable of binding to only one of the primary antibodies used on the section. For example, primary antibodies could be selected that are derived from different animal species (such as mouse, rabbit, rat, and got antibodies), in which case species-specific secondary antibodies may be used. As another example, each primary antibody may include a different hapten or epitope tag, and the secondary antibodies are selected to specifically bind to the hapten or epitope tag. Additionally, each set of detection reagents should be adapted to deposit a different detectable entity on the section, such as by depositing a different enzyme in proximity to each biomarker-specific reagent. An example of such an arrangement is shown at U.S. Pat. No. 8,603,765. Such arrangements have the potential advantage of being able to have each set of biomarker-specific reagents and associated specific binding reagents present on the sample at the same time and/or to perform staining with cocktails of biomarker-specific reagents and detection reagents, thereby reducing the number of staining steps. However, such arrangements may not always be feasible, as reagents may cross-react with different enzymes, and the various antibodies may cross-react with one another, leading to aberrant staining.

Another way to accomplish differential labelling of different biomarkers is to sequentially stain the sample for each biomarker. In such an embodiment, a first biomarker-specific reagent is reacted with the section, followed by a secondary detection reagent to the first biomarker-specific reagent and other detection reagents resulting in deposition of a first detectable entity. The section is then treated to remove the biomarker-specific reagents and associated detection reagents from the section while leaving the deposited stain in place. The process is repeated for subsequent biomarker-specific reagent. Examples of methods for removing the biomarker-specific reagents and associated detection reagents include heating the sample in the presence of a buffer that elutes the antibodies from the sample (termed a "heat-kill method"), such as those disclosed by Stack et al., *Multiplexed immunohistochemistry, imaging, and quantitation: A review, with an assessment of Tyramide signal amplification, multispectral imaging and multiplex analysis*, Methods, Vol. 70, Issue 1, pp 46-58 (November 2014), and PCT/EP2016/057955, the contents of which are incorporated by reference.

As will be appreciated by the skilled artisan, combination staining and sequential staining methods may be combined. For example, where only a subset of the primary antibodies is compatible with combination staining, the sequential staining method can be modified, wherein the antibodies compatible with combination staining are applied to the sample using a combination staining method, and the remaining antibodies are applied using a sequential staining method.

III.C.3. Counterstaining

If desired, the biomarker-stained slides may be counterstained to assist in identifying morphologically relevant areas for identifying ROIs, either manually or automatically. Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4',6-diamino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III.C.4. Morphological Staining of Samples

In certain embodiments, it is also desirable to morphologically stain a serial section of the biomarker-stained section 102. This section can be used to identify the ROIs from which scoring is conducted 103. Basic morphological staining techniques often rely on staining nuclear structures with a first dye, and staining cytoplasmic structures with a second stain. Many morphological stains are known, including but not limited to, hematoxylin and eosin (H & E) stain and Lee's Stain (Methylene Blue and Basic Fuchsin). In a specific embodiment, at least one serial section of each biomarker-stained slide is H & E stained. Any method of applying H & E stain may be used, including manual and automated methods. In an embodiment, at least one section of the sample is an H & E stained sampled stained on a automated staining system. Automated systems for performing H & E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent.

Examples of commercially available H & E stainers include the VENTANA SYMPHONY (individual slide stainer) and VENTANA HE 600 (individual slide stainer) series H & E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H & E stainers from Leica Biosystems Nussloch GmbH.

III.D. ROIs, Objects, and Features

In an embodiment, one or more objects associated with the biomarkers of the panels are identified in a digital image of the biomarker-stained sample 104. The quantity of objects and/or the relationship of different objects to one another are used to define the features that will be evaluated for development of the scoring function. Non-limiting exemplary panels of potential objects which could be detected from each panel are set forth below in Table 2:

TABLE 2

| Biomarker Panel 1 Potential Objects | Biomarker Panel 2 Potential Objects |
| --- | --- |
| T-cells (CD3+ cells) | Cytotoxic T-cells (CD8$^+$) |
| Cytotoxic T-cells (CD8$^+$ cells) | Epithelial cells (EM$^+$ cells) |
| Epithelial cells (EM+ cells) | Stromal cells (EM– cells) |
| Stromal cells (EM– cells) | PD-L1$^+$ cells |
| Macrophages (CD68$^+$ cells) | PD-L1$^-$ cells |
| PD-L1$^+$ cells | PD-1$^+$ cells |
| PD-L1$^-$ cells | PD-1$^-$ cells |
| PD-L1$^+$ CTL (PD-L1$^+$ CD8$^+$); | LAG3$^+$ cells |
| PD-L1$^-$ CTL (PD-L1$^-$ CD8$^+$) | LAG3$^-$ cells |
| PD-L1$^+$ epithelial cell (PD-L1+ EM+ cells) | PD-1$^+$ CTL (PD-1$^+$ CD8$^+$ cells); |
| PD-L1$^+$ stroma (PD-L1+ EM– cells) | PD-1$^-$ CTL (PD-1$^-$ CD8$^+$ cells) |
| PD-L1$^-$ epithelial cell (PD-L1– EM+ cells) | PD-L1$^+$ CTL (PD-L1$^+$ CD8$^+$ cells); |
| PD-L1– stroma (PD-L1– EM– cells) | PD-L1$^-$ CTL (PD-L1$^-$ CD8$^+$) |
| PD-L1$^+$ Macrophages (PD-L1$^+$ CD68$^+$) | PD-L1$^+$ epithelial cell (PD-L1+ EM+ cells) |
| PD-L1$^-$ Macrophages (PD-L1$^-$ CD68$^+$) | PD-L1$^+$ stroma (PD-L1+ EM– cells) |
| PD-L1$^+$ T-cells (PD-L1$^+$ CD3$^+$) | PD-L1$^-$ epithelial cell (PD-L1– EM+ cells) |
| PD-L1$^-$ T-cells (PD-L1$^-$ CD3$^+$) | PD-L1– stroma (PD-L1– EM– cells) |
| | LAG3$^+$ CTL (LAG3$^+$ CD8$^+$); |
| | LAG3$^-$ CTL (LAG3$^-$ CD8$^+$) |
| | LAG3$^+$ epithelial cell (LAG3+ EM+ cells) |
| | LAG3$^+$ stroma (LAG3+ EM– cells) |
| | LAG3$^-$ epithelial cell (LAG3– EM+ cells) |
| | LAG3– stroma (LAG3– EM– cells) |

In some embodiments, one or more regions of interest (ROI) are also identified in the digital images of the biomarker-stained samples 104. The ROI encompasses a biologically relevant location of the tissue section from which relevant objects are identified for feature calculation. In an embodiment, the ROI is a morphological region of a tumor-containing tissue section, such as a tumor region (TR), an invasive front, and a peri-tumoral (PT) region.

The ROI may be limited to the morphological region, may be expanded to include regions outside of the morphological region (i.e. by extending the margin of the ROI a defined distance outside of the morphological region), or may be restricted to a sub-region of the morphological region (for example, by shrinking the ROI a defined distance inside of the circumference of the morphological region or by identifying regions within the ROI having certain characteristics (such as a baseline density of certain cell types)). Where the morphological region defined by an edge (such as an invasive front), the ROI may be defined as, for example, all points within a defined distance of any point of the edge, all points on one side of the edge within a defined distance of any point of the edge, a minimal geometric region (such as a circle, oval, square, rectangle, etc.) encompassing the entire edge region, all points within a circle having a defined radius centered on a center point of the edge region, etc.

In some embodiments, the same ROI may be used for all sections and biomarkers. For example, a morphologically defined ROI may be identified in an H & E-stained section of the sample and used for all biomarker-stained sections. In other embodiments, different ROIs may be used for different biomarkers. For example, an H & E stained slide could be used to identify a particular morphological region used as a first ROI, such as a tumor region. A second ROI or ROIs may then be identified in one of the biomarker-stained sections, for example, used for identifying regions having a class of cells at a certain threshold density (such as epithelial versus stromal regions). The second ROI or ROIs may then be used for feature calculation.

Non-limiting examples of different ROIs are displayed at Table 3:

system may also apply a pattern recognition function that uses computer vision and machine learning to identify regions having similar morphological characteristics to delineated and/or auto-generated regions. Thus, for example, a tumor region could be annotated in a semi-automated manner by a method comprising:
 (a) a user annotates the tumor region in an H & E image of the sample by outlining the tumor region; and
 (b) a computer system applies a pattern recognition function to identify additional areas of the sample that have the morphological characteristics of the outlined area, wherein the overall tumor region includes the area annotated by the user and the areas automatically identified by the system.

In another example, a PR, PI, and/or PO ROI could be annotated in a semi-automated manner by a method comprising:
 (a) a user annotates the tumor region in an H & E image of the sample by outlining the tumor region and invasive front; and
 (b) the computer system automatically defines the PR, PI, and/or PO region(s) encompassing all pixels within the defined distance of the annotated invasive front; and
 (c) the computer system applies a pattern recognition function to identify additional areas of the sample that have the morphological characteristics of the PI, PO, and/or PR regions identified by step (b).

TABLE 3

| ROI | Description |
| --- | --- |
| Tumor area (TA) | Area delineated by a trained user (such as a pathologist) identifying any regions of tumor cells |
| Epithelial area (EA) | Area of EM+ cell aggregates |
| Stromal area (SA) | Any area of a sample not contained within an epithelial area |
| Peritumor inner (PI) | An area entirely inside of the tumor area extending a pre-determined distance away from the invasive front |
| Peritumor outer (PO) | An area entirely outside of the tumor area extending a pre-determined distance away from the invasive front |
| Peritumor region (PR) | An area encompassing the invasive front and extending a predetermined distance away from the invasive front into the tumor and a predetermined distance away from the invasive front toward the outside of the tumor |

In some embodiments, the ROI is manually identified in the digital image. For example, a trained expert may manually delineate one or more morphological region(s) (such as a tumor area and/or an invasive front) on a digital image of the sample. The area(s) delineated in the image may then be used as the ROI for calculation of the features or a reference point for calculation of the ROI.

In other embodiments, a computer-implemented system may assist the user in annotating the ROI (termed, "semi-automated ROI annotation"). For example, the user may delineate one or more regions on the digital image, which the system then automatically transforms into a complete ROI. For example, if the desired ROI is an PI, PO, and/or PR region, a user can delineate a tumor region and an invasive front, and the system automatically draws the PI, PO, and PR regions as defined by the user. In another embodiment, where the ROI is an EA or a SA, the user may draw the tumor region and, optionally, the invasive front in the image, which is then registered to the biomarker-stained image, and the system creates the relevant EA and SA ROIs by marking all cells within the pre-defined distance of an EM+ cell as being within the EA, and all cells beyond the pre-defined distance as being within the SA. In another embodiment, the Many other arrangements could be used as well. In cases in which ROI generation is semi-automated, the user may be given an option to modify the ROI annotated by the computer system, such as by expanding the ROI, annotating regions of the ROI or objects within the ROI to be excluded from analysis, etc.

In other embodiments, a computer system may automatically suggest an ROI without any direct input from the user (termed an "automated ROI annotation"). For example, a previously-trained tissue segmentation function or other pattern recognition function may be applied to an unannotated image to identify the desired morphological region to use as an ROI. The user may be given an option to modify the ROI annotated by the computer system, such as by expanding the ROI, annotating regions of the ROI or objects within the ROI to be excluded from analysis, etc.

One or more features is extracted from the ROI(s) and quantitated to obtain a feature metric for each sample 105. Exemplary features include, for example, total number of objects in the ROI, density of specific objects in the ROI, spatial relationships between different objects in the ROI, spatial distribution of specific object within the ROI, ratios of numbers and/or densities of different objects within the ROI, ratio of the same objects in different ROIs (for example, ratio of specific cells in a EA ROI versus an SA ROI or ratio of specific cells in a PI ROI versus a PO ROI), fraction of total objects of a larger ROI that fall within a smaller ROI that falls within the larger ROI (for example, fraction of a specific cell type of a TA ROI that falls within an EA, SA, PI, PO, or PT ROI. Specific exemplary features for each panel are set forth in Table 4:

TABLE 4

| Panel 1<br>(CD8; EM; CD68; CD3; PD-L1) | Panel 2<br>(CD8; EM; PD-L1; PD-1; LAG3) |
|---|---|
| T.CD8–PDL1+CD68 Dist;<br>T.CD8–PDL1+CD3All Dist;<br>T.EM–CD8 Dist;<br>T.No.PDL1+EM in10 μm CD8;<br>T.No.PDL1+EM in30 μm CD8;<br>T.No.CD8 in10 μm EM;<br>T.No.CD8 in30 μm EM;<br>Epith.CD8toPDL1+CD68 Dist;<br>Epith.CD8toPDL1+CD3All Dist;<br>Epith.EMtoCD8 Dist;<br>Epith.No. PDL1+EM in10 μm CD8;<br>Epith.No.PDL1+EM in30 μm CD8;<br>Epith.No.CD8 in 10 μm EM;<br>Epith.No.CD8 in30 μm EM;<br>Str.CD8toPDL1+CD68 Dist;<br>Str.CD8toPDL1+CD3All Dist;<br>Str.EMtoCD8 Dist;<br>Str.No.PDL1+EM in10 μm CD8;<br>Str.No.PDL1+EM in30 μm CD8;<br>Str.No.CD8 in10 μm EM;<br>Str.No.CD8 in30 μm EM;<br>PI.CD8toPDL1+CD68 Dist;<br>PI.CD8toPDL1+CD3All Dist;<br>PI.EMtoCD8 Dist;<br>PI.No.PDL1+EM in10 μm CD8;<br>PI.No.PDL1+EM in30 μm CD8;<br>PI.No.CD8 in10 μm EM;<br>PI.No.CD8 in30 μm EM;<br>PO.CD8toPDL1+CD68 Dist;<br>PO.CD8toPDL1+CD3All Dist;<br>PO.EMtoCD8 Dist;<br>PO.No.PDL1+EM in10 μm CD8;<br>PO.No.PDL1+EM in30 μm CD8;<br>PO.No.CD8 in10 μm EM;<br>PO.No.CD8 in30 μm EM;<br>PDL1+CD3All density in T;<br>PDL1+CD3+CD8– density in T;<br>PDL1+CD8+ density in T;<br>PDL1+CD68+ density in T;<br>PDL1+EM+ density in T;<br>CD3All density in T;<br>CD8+ density in T;<br>CD68+ density in T;<br>EM+ density in T;<br>PDL1+CD3All density in Epith;<br>PDL1+CD3+CD8– density in Epith;<br>PDL1+CD8+ density in Epith;<br>PDL1+CD68+ density in Epith;<br>PDL1+EM+ density in Epith;<br>CD3All density in Epith;<br>CD8+ density in Epith;<br>CD68+ density in Epith;<br>EM+ density in Epith;<br>PDL1+CD3All density in Str;<br>PDL1+CD3+CD8– density in Str;<br>PDL1+CD8+ density in Str;<br>PDL1+CD68+ density in Str;<br>PDL1+EM+ density in Str;<br>CD3All density in Str;<br>CD8+ density in Str;<br>CD68+ density in Str;<br>EM+ density in Str;<br>PDL1+CD3All density in PI;<br>PDL1+CD3+CD8– density in PI;<br>PDL1+CD8+ density in PI;<br>PDL1+CD68+ density in PI;<br>PDL1+EM+ density in PI;<br>CD3All density in PI;<br>CD8+ density in PI;<br>CD68+ density in PI; | 'number of PD1 positive cells in panCK positive area';<br>'number of PD1 positive cells in panCK negative area';<br>'number of PD1+ panCK+ cells divided by area of panCK positive cells';<br>'number of PD1+ panCK– cells divided by area of panCK negative cells';<br>'number of PDL1 positive cells in panCK positive area';<br>'number of PDL1 positive cells in panCK negative area';<br>'number of PDL1+ panCK+ cells divided by area of panCK positive cells';<br>'number of PDL1+ panCK– cells divided by area of panCK negative cells';<br>'number of CD8 positive cells in panCK positive area';<br>'number of CD8 positive cells in panCK negative area';<br>'number of CD8+ panCK+ cells divided by area of panCK positive cells';<br>'number of CD8+ panCK– cells divided by area of panCK negative cells';<br>'number of Lag3 positive cells in panCK positive area';<br>'number of Lag3 positive cells in panCK negative area';<br>'number of Lag3+ panCK– cells divided by area of panCK positive cells';<br>'number of Lag3+ panCK– cells divided by area of panCK negative cells';<br>'number of Lag3 positive cells in panCK positive area';<br>'number of Lag3 positive cells in panCK negative area';<br>'number of Lag3+ panCK+ cells divided by area of panCK positive cells';<br>'number of Lag3+ panCK– cells divided by area of panCK negative cells';<br>'ratio of number of PD1+&CD8+ to CD8+ cell in panCK positive area';<br>'ratio of number of PD1+&CD8+ to CD8+ cell in panCK negative area';<br>'ratio of number of PD1–&CD8+ to CD8+ cell in panCK positive area';<br>'ratio of number of PD1–&CD8+ to CD8+ cell in panCK negative area';<br>'ratio of number of Lag3+&CD8+ to CD8+ cell in panCK positive area';<br>'ratio of number of Lag3+&CD8+ to CD8+ cell in panCK negative area';<br>'ratio of number of Lag3–&CD8+ to CD8+ cell in panCK positive area';<br>'ratio of number of Lag3–&CD8+ to CD8+ cell in panCK negative area';<br>'ratio of number of PDL1+&CD8+ to CD8+ cell in panCK positive area';<br>'ratio of number of PDL1+&CD8+ to CD8+ cell in panCK negative area';<br>'ratio of number of PDL1–&CD8+ to CD8+ cell in panCK positive area';<br>'ratio of number of PDL1–&CD8+ to CD8+ cell in panCK negative area';<br>'ratio of number of PD1+&Lag3+&CD8+ to CD8+ cell in panCK positive area';<br>'ratio of number of PD1+&Lag3+&CD8+ to CD8+ cell in panCK negative area';<br>'ratio of number of PD1+&PDL1+&CD8+ to CD8+ cell in panCK positive area'; |

TABLE 4-continued

| Panel 1<br>(CD8; EM; CD68; CD3; PD-L1) | Panel 2<br>(CD8; EM; PD-L1; PD-1; LAG3) |
|---|---|
| EM+ density in PI;<br>PDL1+CD3All density in PO;<br>PDL1+CD3+CD8− density in PO;<br>PDL1+CD8+ density in PO;<br>PDL1+CD68+ density in PO;<br>PDL1+EM+ density in PO;<br>CD3All density in PO;<br>CD8+ density in PO;<br>CD68+ density in PO;<br>EM+ density in PO;<br>PDL1+EM+ area ratio in T;<br>EM+ area ratio in T;<br>PDL1+EM+ area ratio in Epith;<br>EM+ area ratio in Epith;<br>PDL1+EM+ area ratio in Str;<br>EM+ area ratio in Str;<br>PDL1+EM+ area ratio in PI;<br>EM+ area ratio in PI;<br>PDL1+EM+ area ratio in PO;<br>EM+ area ratio in PO;<br>PDL1+EM/EM in T;<br>PDL1+EM/EM in Epith;<br>PDL1+EM/EM in Str;<br>PDL1+EM/EM in PI;<br>PDL1+EM/EM in PO;<br>PDL1+CD3All/CD3All in T;<br>PDL1+CD3All/CD3All in Epith;<br>PDL1+CD3All/CD3All in Str;<br>PDL1+CD3All/CD3All in PI;<br>PDL1+CD3All/CD3All in PO;<br>PDL1+CD3+CD8−/CD3+CD8− in T;<br>PDL1+CD3+CD8−/CD3+CD8− in Epith;<br>PDL1+CD3+CD8−/CD3+CD8− in Str;<br>PDL1+CD3+CD8−/CD3+CD8− in PI;<br>PDL1+CD3+CD8−/CD3+CD8− in PO;<br>PDL1+CD8+/CD8+ in T;<br>PDL1+CD8+/CD8+ in Epith;<br>PDL1+CD8+/CD8+ in Str;<br>PDL1+CD8+/CD8+ in PI;<br>PDL1+CD8+/CD8+ in PO;<br>PDL1+CD68+/CD68+ in T;<br>PDL1+CD68+/CD68+ in Epith;<br>PDL1+CD68+/CD68+ in Str;<br>PDL1+CD68+/CD68+ in PI;<br>PDL1+CD68+/CD68+ in PO;<br>CD3+CD8−/CD3All in T;<br>CD3+CD8−/CD3All in Epith;<br>CD3+CD8−/CD3All in Str;<br>CD3+CD8−/CD3All in PI;<br>CD3+CD8−/CD3All in PO;<br>CD3All density in EM in T;<br>CD3All density in EM in Epith;<br>CD3All density in EM in PI;<br>CD8 density in EM in T;<br>CD8 density in EM in Epith;<br>CD8 density in EM in PI;<br>CD3 Aggregate Area;<br>CD8 Aggregate Area | 'ratio of number of PD1+&PDL1+&CD8+ to CD8+ cell in panCK negative area';<br>'ratio of number of PD1+&PDL1+&Lag3+&CD8+ to CD8+ cell in panCK positive area';<br>'ratio of number of PD1+&PDL1+&Lag3+&CD8+ to CD8+ cell in panCK negative area';<br>'ratio of number of PD1−&PDL1+&Lag3+&CD8+ to CD8+ cell in panCK positive area';<br>'ratio of number of PD1−&PDL1+&Lag3+&CD8+ to CD8+ cell in panCK negative area';<br>'ratio of number of PD1+&PDL1−&Lag3+&CD8+ to CD8+ cell in panCK positive area';<br>'ratio of number of PD1+&PDL1−&Lag3+&CD8+ to CD8+ cell in panCK negative area';<br>'mean value of all cell PD1 intensity';<br>'variance of all cell PD1 intensity';<br>'min value of all cell PD1 intensity';<br>'max value of all cell PD1 intensity';<br>'mean value of CD8+ cell PD1 intensity';<br>'variance of CD8+ cell PD1 intensity';<br>'min value of CD8+ cell PD1 intensity';<br>'max value of CD8+ cell PD1 intensity';<br>'mean value of all cell PDL1 intensity';<br>'variance of all cell PDL1 intensity';<br>'min value of all cell PDL1 intensity';<br>'max value of all cell PDL1 intensity';<br>'mean value of CD8+ cell PDL1 intensity';<br>'variance of CD8+ cell PDL1 intensity';<br>'min value of CD8+ cell PDL1 intensity';<br>'max value of CD8+ cell PDL1 intensity';<br>'mean value of panCK+ cell PDL1 intensity';<br>'variance of panCK+ cell PDL1 intensity';<br>'min value of panCK+ cell PDL1 intensity';<br>'max value of panCK+ cell PDL1 intensity';<br>'mean value of all cell Lag3 intensity';<br>'variance of all cell Lag3 intensity';<br>'min value of all cell Lag3 intensity';<br>'max value of all cell Lag3 intensity';<br>'mean value of CD8+ cell Lag3 intensity';<br>'variance of CD8+ cell Lag3 intensity';<br>'min value of CD8+ cell Lag3 intensity';<br>'max value of CD8+ cell Lag3 intensity';<br>'mean number of PD1 within 10 μm radius of PDL1';<br>'variance of number of PD1 within 10 μm radius of PDL1';<br>'min number of PD1 within 10 μm radius of PDL1';<br>'max number of PD1 within 10 μm radius of PDL1';<br>'mean number of PD1 within 20 μm radius of PDL1';<br>'variance of number of PD1 within 20 μm radius of PDL1';<br>'min number of PD1 within 20 μm radius of PDL1';<br>'max number of PD1 within 20 μm radius of PDL1';<br>'mean number of PDL1 within 10 μm radius of PD1';<br>'variance of number of PDL1 within 10 μm radius of PD1';<br>'min number of PDL1 within 10 μm radius of PD1';<br>'max number of PDL1 within 10 μm radius of PD1';<br>'mean number of PDL1 within 20 μm radius of PD1';<br>'variance of number of PDL1 within 20 μm radius of PD1';<br>'min number of PDL1 within 20 μm radius of PD1';<br>'max number of PDL1 within 20 μm radius of PD1';<br>'mean number of PD1+&CD8+ within 10 μm radius of PDL1';<br>'variance of number of PD1+&CD8+ within 10 μm radius of PDL1';<br>'min number of PD1+&CD8+ within 10 μm radius of PDL1';<br>'max number of PD1+&CD8+ within 10 μm radius of PDL1'; |

TABLE 4-continued

| Panel 1<br>(CD8; EM; CD68; CD3; PD-L1) | Panel 2<br>(CD8; EM; PD-L1; PD-1; LAG3) |
|---|---|
| | 'mean number of PD1+&CD8+ within 20 μm radius of PDL1';<br>'variance of number of PD1+&CD8+ within 20 μm radius of PDL1';<br>'min number of PD1+&CD8+ within 20 μm radius of PDL1';<br>'max number of PD1+&CD8+ within 20 μm radius of PDL1';<br>'mean number of PD1+&CD8+ within 10 μm radius of PDL1+&panCK+';<br>'variance of number of PD1+&CD8+ within 10 μm radius of PDL1+&panCK+';<br>'min number of PD1+&CD8+ within 10 μm radius of PDL1+&panCK+';<br>'max number of PD1+&CD8+ within 10 μm radius of PDL1+&panCK+';<br>'mean number of PD1+&CD8+ within 20 μm radius of PDL1+&panCK+';<br>'variance of number of PD1+&CD8+ within 20 μm radius of PDL1+&panCK+';<br>'min number of PD1+&CD8+ within 20 μm radius of PDL1+&panCK+';<br>'max number of PD1+&CD8+ within 20 μm radius of PDL1+&panCK+';<br>'mean number of PD1+&CD8+ within 10 μm radius of PDL1+&CD8+';<br>'variance of number of PD1+&CD8+ within 10 μm radius of PDL1+&CD8+';<br>'min number of PD1+&CD8+ within 10 μm radius of PDL1+&CD8+';<br>'max number of PD1+&CD8+ within 10 μm radius of PDL1+&CD8+';<br>'mean number of PD1+&CD8+ within 20 μm radius of PDL1+&CD8+';<br>'variance of number of PD1+&CD8+ within 20 μm radius of PDL1+&CD8+';<br>'min number of PD1+&CD8+ within 20 μm radius of PDL1+&CD8+';<br>'max number of PD1+&CD8+ within 20 μm radius of PDL1+&CD8+';<br>'mean number of PD1Low&CD8+ within 10 μm radius of PDL1';<br>'variance of number of PD1Low&CD8+ within 10 μm radius of PDL1';<br>'min number of PD1Low&CD8+ within 10 μm radius of PDL1';<br>'max number of PD1Low&CD8+ within 10 μm radius of PDL1';<br>'mean number of PD1Low&CD8+ within 20 μm radius of PDL1';<br>'variance of number of PD1Low&CD8+ within 20 μm radius of PDL1';<br>'min number of PD1Low&CD8+ within 20 μm radius of PDL1';<br>'max number of PD1Low&CD8+ within 20 μm radius of PDL1';<br>'mean number of PD1Low&CD8+ within 10 μm radius of PDL1+&panCK+';<br>'variance of number of PD1Low&CD8+ within 10 μm radius of PDL1+&panCK+';<br>'min number of PD1Low&CD8+ within 10 μm radius of PDL1+&panCK+';<br>'max number of PD1Low&CD8+ within 10 μm radius of PDL1+&panCK+';<br>'mean number of PD1Low&CD8+ within 20 μm radius of PDL1+&panCK+';<br>'variance of number of PD1Low&CD8+ within 20 μm radius of PDL1+&panCK+';<br>'min number of PD1Low&CD8+ within 20 μm radius of PDL1+&panCK+';<br>'max number of PD1Low&CD8+ within 20 μm radius of PDL1+&panCK+';<br>'mean number of PD1Low&CD8+ within 10 μm radius of PDL1+&CD8+';<br>'variance of number of PD1Low&CD8+ within 10 μm radius of PDL1+&CD8+'; |

TABLE 4-continued

| Panel 1<br>(CD8; EM; CD68; CD3; PD-L1) | Panel 2<br>(CD8; EM; PD-L1; PD-1; LAG3) |
|---|---|
| | 'min number of PD1Low&CD8+ within 10 μm radius of PDL1+&CD8+';<br>'max number of PD1Low&CD8+ within 10 μm radius of PDL1+&CD8+';<br>'mean number of PD1Low&CD8+ within 20 μm radius of PDL1+&CD8+';<br>'variance of number of PD1Low&CD8+ within 20 μm radius of PDL1+&CD8+';<br>'min number of PD1Low&CD8+ within 20 μm radius of PDL1+&CD8+';<br>'max number of PD1Low&CD8+ within 20 μm radius of PDL1+&CD8+';<br>'mean number of PD1Med&CD8+ within 10 μm radius of PDL1';<br>'variance of number of PD1Med&CD8+ within 10 μm radius of PDL1';<br>'min number of PD1Med&CD8+ within 10 μm radius of PDL1';<br>'max number of PD1Med&CD8+ within 10 μm radius of PDL1';<br>'mean number of PD1Med&CD8+ within 20 μm radius of PDL1';<br>'variance of number of PD1Med&CD8+ within 20 μm radius of PDL1';<br>'min number of PD1Med&CD8+ within 20 μm radius of PDL1';<br>'max number of PD1Med&CD8+ within 20 μm radius of PDL1';<br>'mean number of PD1Med&CD8+ within 10 μm radius of PDL1+&panCK+';<br>'variance of number of PD1Med&CD8+ within 10 μm radius of PDL1+&panCK+';<br>'min number of PD1Med&CD8+ within 10 μm radius of PDL1+&panCK+';<br>'max number of PD1Med&CD8+ within 10 μm radius of PDL1+&panCK+';<br>'mean number of PD1Med&CD8+ within 20 μm radius of PDL1+&panCK+';<br>'variance of number of PD1Med&CD8+ within 20 μm radius of PDL1+&panCK+';<br>'min number of PD1Med&CD8+ within 20 μm radius of PDL1+&panCK+';<br>'max number of PD1Med&CD8+ within 20 μm radius of PDL1+&panCK+';<br>'mean number of PD1Med&CD8+ within 10 μm radius of PDL1+&CD8+';<br>'variance of number of PD1Med&CD8+ within 10 μm radius of PDL1+&CD8+';<br>'min number of PD1Med&CD8+ within 10 μm radius of PDL1+&CD8+';<br>'max number of PD1Med&CD8+ within 10 μm radius of PDL1+&CD8+';<br>'mean number of PD1Med&CD8+ within 20 μm radius of PDL1+&CD8+';<br>'variance of number of PD1Med&CD8+ within 20 μm radius of PDL1+&CD8+';<br>'min number of PD1Med&CD8+ within 20 μm radius of PDL1+&CD8+';<br>'max number of PD1Med&CD8+ within 20 μm radius of PDL1+&CD8+';<br>'mean number of PD1High&CD8+ within 10 μm radius of PDL1';<br>'variance of number of PD1High&CD8+ within 10 μm radius of PDL1';<br>'min number of PD1High&CD8+ within 10 μm radius of PDL1';<br>'max number of PD1High&CD8+ within 10 μm radius of PDL1';<br>'mean number of PD1High&CD8+ within 20 μm radius of PDL1';<br>'variance of number of PD1High&CD8+ within 20 μm radius of PDL1';<br>'min number of PD1High&CD8+ within 20 μm radius of PDL1'; |

TABLE 4-continued

| Panel 1<br>(CD8; EM; CD68; CD3; PD-L1) | Panel 2<br>(CD8; EM; PD-L1; PD-1; LAG3) |
|---|---|
| | 'max number of PD1High&CD8+ within 20 μm radius of PDL1';<br>'mean number of PD1High&CD8+ within 10 μm radius of PDL1+&panCK+';<br>'variance of number of PD1High&CD8+ within 10 μm radius of PDL1+&panCK+';<br>'min number of PD1High&CD8+ within 10 μm radius of PDL1+&panCK+';<br>'max number of PD1High&CD8+ within 10 μm radius of PDL1+&panCK+';<br>'mean number of PD1High&CD8+ within 20 μm radius of PDL1+&panCK+';<br>'variance of number of PD1High&CD8+ within 20 μm radius of PDL1+&panCK+';<br>'min number of PD1High&CD8+ within 20 μm radius of PDL1+&panCK+';<br>'max number of PD1High&CD8+ within 20 μm radius of PDL1+&panCK+';<br>'mean number of PD1High&CD8+ within 10 μm radius of PDL1+&CD8+';<br>'variance of number of PD1High&CD8+ within 10 μm radius of PDL1+&CD8+';<br>'min number of PD1High&CD8+ within 10 μm radius of PDL1+&CD8+';<br>'max number of PD1High&CD8+ within 10 μm radius of PDL1+&CD8+';<br>'mean number of PD1High&CD8+ within 20 μm radius of PDL1+&CD8+';<br>'variance of number of PD1High&CD8+ within 20 μm radius of PDL1+&CD8+';<br>'min number of PD1High&CD8+ within 20 μm radius of PDL1+&CD8+';<br>'max number of PD1High&CD8+ within 20 μm radius of PDL1+&CD8+';<br>'number of co-expressed PD1/PDL1 cells';<br>'number of co-expressed PD1PosCD8Pos/PDL1 cells';<br>'average distance from PD1 to its nearest PDL1';<br>'average distance from PD1Pos&CD8Pos to its nearest PDL1';<br>'average distance from PDL1 to its nearest PD1';<br>'std of distance from PD1 to its nearest PDL1';<br>'std of distance from PD1 to its nearest PDL1';<br>'std of distance from PDL1 to its nearest PD1' |

Unless otherwise stated, the ROI for the features of Table 4 is the tumor area. Unless otherwise stated, any densities recited in Table 4 are area density (i.e. number of positive cells over area of the ROI). As used in Table 4, "PD1Low," "PD1Med," and "PD1High" refer to individual cells having low, medium, and high PD-1 staining intensities. In an embodiment, a "PD1low" cell is a PD-1+ cell having a staining intensity in the lowest third of all measured PD-1+ cells across all samples tested, a "PD1med" cell is a PD-1+ cell having a staining intensity in the middle third of all measured PD-1+ cells across all samples tested, and a "PD1high" cell is a PD-1+ cell having a staining intensity in the highest third of all measured PD-1+ cells across all samples tested.

III.F. Modeling the Scoring Function

In order to identify the scoring function, the features are modeled for their ability to predict the relative likelihood of responding to a PD-1 axis directed therapeutic course.

In an embodiment, the features may be selected by executing a feature selection function 106. Feature metric and outcome data for each member of the cohort are input into the feature selection function, which then uses the data to rank the different features according to their relative correlation with the desired outcome. Exemplary feature selection functions include ensemble feature selection functions (including, for example, a Random Forest function), filter method functions (including, for example, Mutual information based functions, (mRMR)/correlation coefficient based functions, and Relief based functions), and/or an embedded feature selection function (such as an elastic net/least absolute shrinkage function or a selection operator (LASSO) functions). In an embodiment, candidate models are made using the top 25, top 20, top 15, top 10, top 9, top 8, top 7, top 6, top 5, top 4 or top 3 features identified by the feature selection function. In another embodiment, the candidate models use at least 1, at least 2, at least 3, at least 4, or at least 5 features identified in the top 10 features of at least two different feature selection functions. In another embodiment, the candidate models include at least one feature present in the top 5 features of at least 2 feature selection functions. In an embodiment, a "responder" is considered a patient having either a partial response or a complete response. In an embodiment, a "responder" is considered a patient having stable disease, a partial response, or a complete response.

Candidate models are generated by inputting selected feature metrics and outcome data for each member of the cohort into a modeling function. The model having the highest concordance with response is selected as the scoring function. Exemplary modeling functions include quadrant discriminant analysis (QDA), Linear discriminant analysis (LDA), Support vector machine (SVM), and Artificial neural network (ANN). In an embodiment, the candidate functions modeled only on features extracted from the digital image. In other embodiments, the candidate functions include other clinical variables, such as age, sex, mismatch repair status, and/or microsatellite instability status. In an embodiment, the model is used to predict the likelihood of progressive disease after treatment versus stable disease after treatment versus a partial or complete response to the therapy. In an embodiment, the model is used to predict the likelihood that the patient will have progressive disease after treatment versus the likelihood that the patient will have stable disease, a partial response, or a complete response to the therapy. In an embodiment, the model is used to predict the likelihood that the patient will have progressive disease or stable disease after treatment versus the likelihood that the patient will have a partial or complete response to the therapy.

Additionally, one or more stratification cutoffs may be selected to separate the patients into "risk bins" according to relative risk (such as "high risk" and "low risk," quartiles, deciles, etc.) 107. In one example, stratification cutoffs are selected using receiver operator characteristic (ROC) curves. ROC curves allow users to balance the sensitivity of the model (i.e. prioritize capturing as many "positive" or "likely to respond" candidates as possible) with the specificity of the model (i.e. minimizing false-positives for "likely to respond" candidates). In an embodiment, a cutoff is selected between likely to respond and unlikely to respond risk bins, the cutoff chosen having the sensitivity and specificity balanced. In an embodiment, stratification cutoffs differentiate between (a) patients likely to have progressive disease after treatment and (b) patients likely to have stable disease, a partial response, or a complete response to the therapy. In an embodiment, the stratification cutoffs differentiate between (a) patients likely to have progressive disease after treatment, (b) patients likely to have stable disease after treatment, and (c) patients likely to have a partial response or a complete response to the therapy. In an embodiment, the stratification cutoffs differentiate between (a) patients likely to have progressive disease or stable disease after treatment and (b) patients likely to have a partial or complete response to the therapy.

Models may be performed, if desired, using a computerized statistical analysis software suite (such as The R Project for Statistical Computing (available at https://www.r-project.org/), SAS, MATLAB, among others).

IV. Scoring with a Scoring Function

Figure 2:
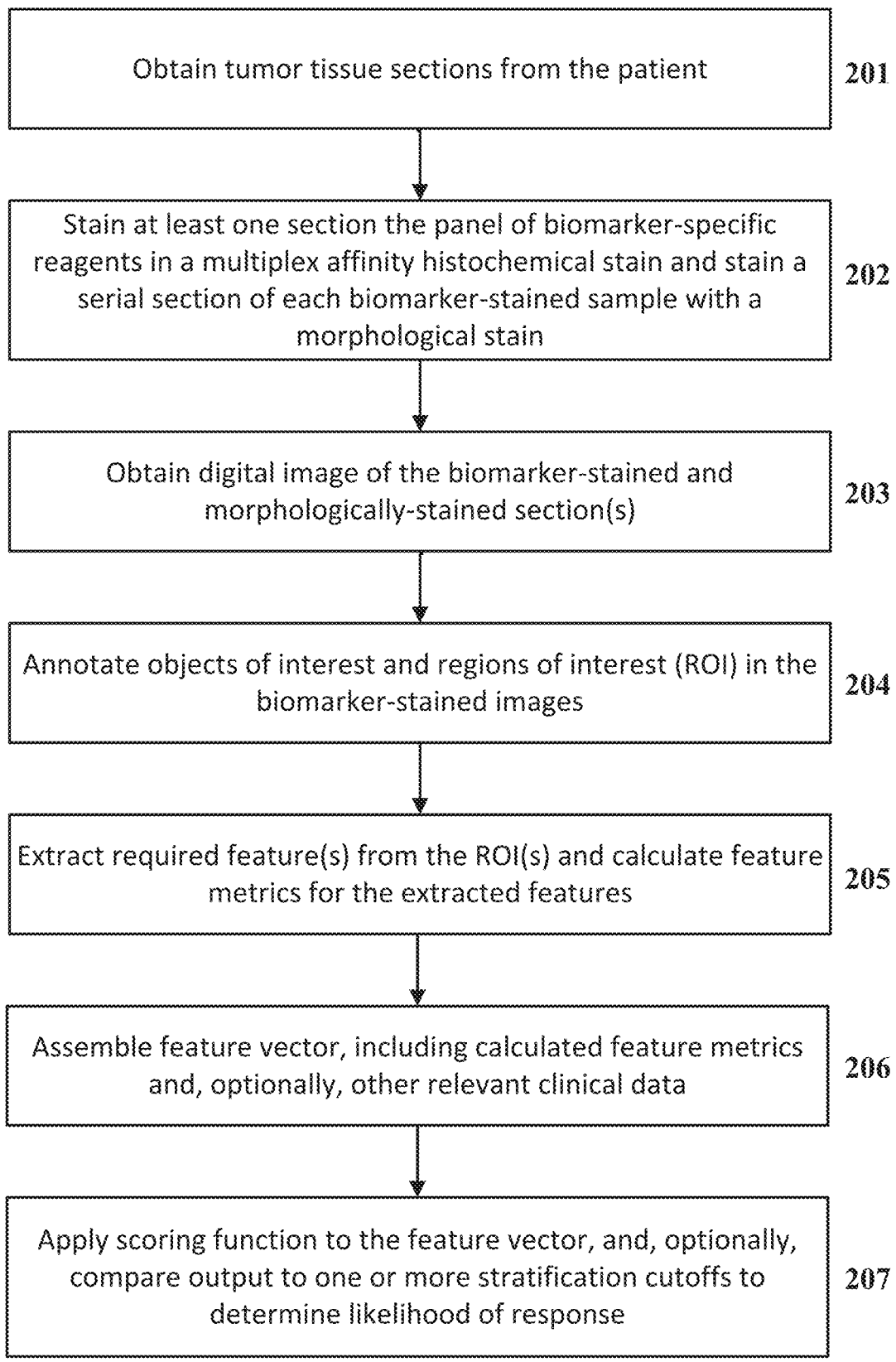
FIG. 2 is a flow chart illustrating an exemplary approach to scoring test samples using a scoring function as described herein.

After the scoring function has been modeled and optional stratification cutoffs have been selected, the scoring function may be applied to images of test samples to calculate a score for the test sample. FIG. 2 is a flow chart illustrating an exemplary approach to scoring test samples using a scoring functions as described above. Tumor tissue sections are first obtained from a patient for whom a PD-1 axis directed therapy is being considered 201. The tissue sections are typically similar to the sample types used for modeling the scoring function, except that outcomes are not yet known. At least one of the tissue sections is stained for the biomarkers relevant to the scoring function and a serial section thereof is stained with a morphological stain (such as H & E) if needed for ROI selection 202. The stained sections are imaged 203, and one or more ROIs relevant to the scoring function are annotated in the biomarker-stained image, along with any objects used in calculation of the relevant feature metrics 204. The relevant features are extracted from the ROI and a feature metric for each feature is calculated 205. A feature vector is then assembled including all variables used by the scoring function 206, and the scoring function is applied to the feature vector 207. In some instances, the variables are only the feature metrics extracted from the ROIs. In other instances, additional clinical variables may be included, such as, for example, age, sex, mismatch repair status (such as whether the patient has deficient MMR (dMMR) or proficient MMR (pMMR)), microsatellite instability status (such as whether the patient is $MSI^{high}$ or $MSI^{low}$. If stratification cutoffs are being used, the output score may also be assigned to the relevant risk bin. The score may then be integrated into diagnostic and/or treatment decisions by a clinician, including, for example, by integrating the score with other clinical variables that may weigh into a decision whether or not to administer a PD-1 axis directed therapy.

In an embodiment, the scoring function is integrated into a scoring system. An exemplary scoring system is illustrated at FIG. 3.

The scoring system includes an image analysis system 300. Image analysis system 300 may include one or more computing devices such as desktop computers, laptop computers, tablets, smartphones, servers, application-specific computing devices, or any other type(s) of electronic device(s) capable of performing the techniques and operations described herein. In some embodiments, image analysis system 300 may be implemented as a single device. In other embodiments, image analysis system 300 may be implemented as a combination of two or more devices together achieving the various functionalities discussed herein. For example, image analysis system 300 may include one or more server computers and a one or more client computers communicatively coupled to each other via one or more local-area networks and/or wide-area networks such as the Internet.

Figure 3:
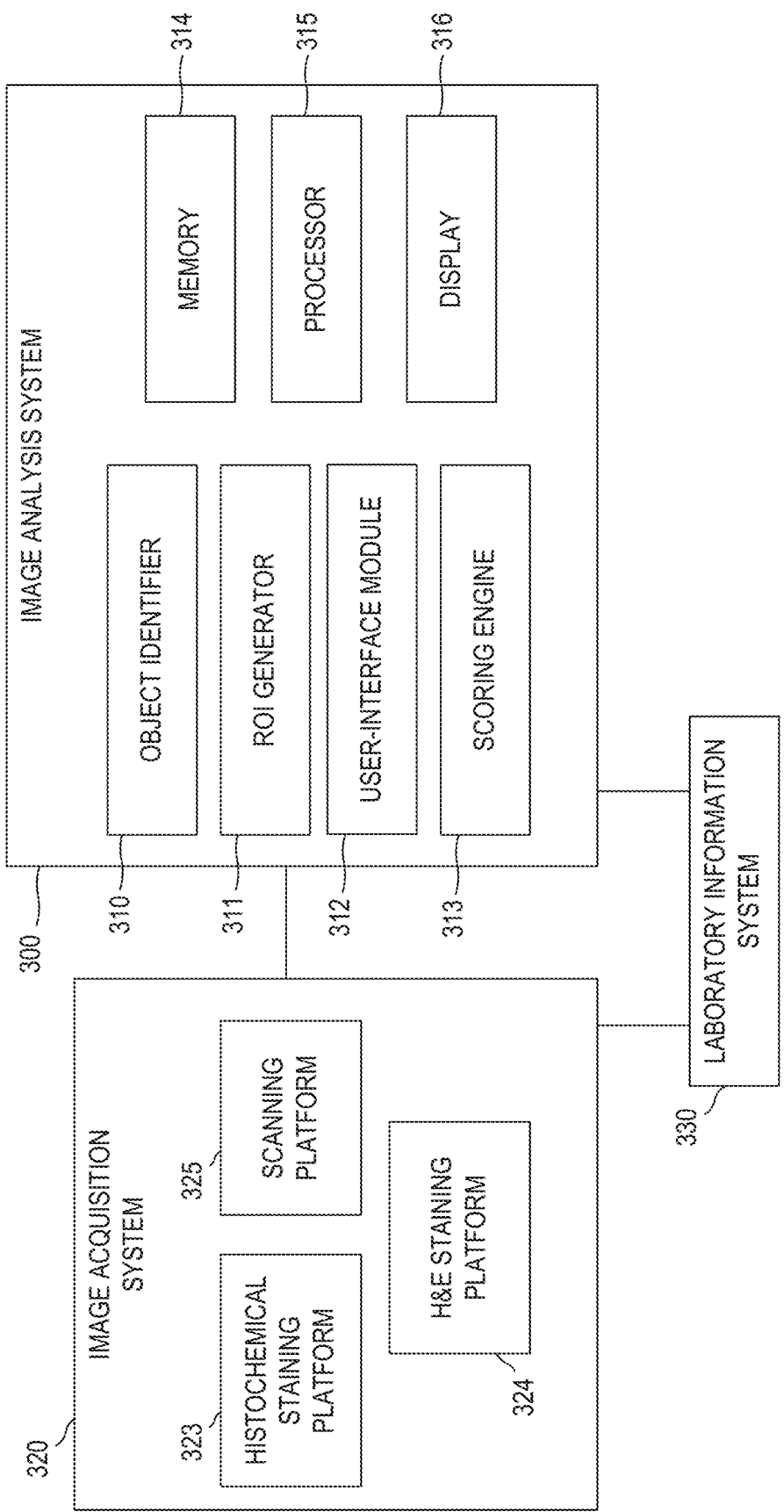
FIG. 3 illustrates an exemplary scoring system that integrates a scoring function as described herein.

As illustrated in FIG. 3, image analysis system 300 may include a memory 314, a Processor 315, and a display 316. Memory 314 may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. For brevity purposes memory 314 is depicted in FIG. 3 as a single device, but it is appreciated that memory 314 can also be distributed across two or more devices.

Processor 315 may include one or more processors of any type, such as central processing units (CPUs), graphics processing units (GPUs), special-purpose signal or image processors, field-programmable gate arrays (FPGAs), tensor processing units (TPUs), and so forth. For brevity purposes Processor 315 is depicted in FIG. 3 as a single device, but it is appreciated that Processor 315 can also be distributed across any number of devices.

Display 316 may be implemented using any suitable technology, such as LCD, LED, OLED, TFT, Plasma, etc. In some implementations, display 316 may be a touch-sensitive display (a touchscreen).

As illustrated in FIG. 3, image analysis system 300 may also include an object identifier 310, a region of interest (ROI) generator 311, a user-interface module 312, and a scoring engine 313. While these modules are depicted in FIG. 3 as standalone modules, it will be evident to persons having ordinary skill in the art that each module may instead be implemented as a number of sub-modules, and that in some embodiments any two or more modules can be combined into a single module. Furthermore, in some embodiments, system 100 may include additional engines and modules (e.g., input devices, networking and communication modules, etc.) not depicted in FIG. 3 for brevity. Furthermore, in some embodiments, some of the blocks depicted in FIG. 3 may be disabled or omitted. As will be discussed in more detail below, the functionality of some or all modules of system 100 can be implemented in hardware, software, firmware, or as any combination thereof. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

After acquiring the image, image analysis system 300 may pass the image to an object identifier 310, which functions to identify and mark relevant objects and other features within the image that will later be used for scoring. Object identifier 310 may extract from (or generate for) each image a plurality of image features characterizing the various objects in the image as a well as pixels representing expression of the biomarker(s). The extracted image features may include, for example, texture features such as Haralick features, bag-of-words features and the like. The values of the plurality of image features may be combined into a high-dimensional vector, hereinafter referred to as the "feature vector" characterizing the expression of the biomarker relevant to the features of the scoring function. For example, if M features are extracted for each object and/or pixel, each object and/or pixel can be characterized by an M-dimensional feature vector. The output of object identifier 310 is effectively a map of the image annotating the position of objects and pixels of interest and associating those objects and pixels with a feature vector describing the object or pixels.

For biomarkers that are scored on the basis of the biomarker's association with a particular type of object (such as membranes, nuclei, cells, etc.), the features extracted by object identifier 310 may include features or feature vectors sufficient to categorize the objects in the sample as biomarker-positive objects of interest or biomarker-negative markers of interest and/or by level or intensity of biomarker staining of the object. In cases where the biomarker may be weighted differently depending on the object type that is expressing it, the features extracted by object identifier 310 may include features relevant to determining the type of objects associated with biomarker-positive pixels. Thus, the objects may then be categorized at least on the basis of biomarker expression (for example, biomarker-positive or biomarker-negative cells) and, if relevant, a sub-type of the object (e.g. tumor cell, immune cell, etc.). In cases where extent of biomarker-expression is scored regardless of association with objects, the features extracted by object identifier 310 may include for example location and/or intensity of biomarker-positive pixels. The precise features extracted from the image will depend on the type of classification function being applied, and would be well-known to a person of ordinary skill in the art.

An example of objects identified for certain biomarker panels is set forth below in Table 5:

TABLE 5

| Biomarker Panel 1 Objects | Biomarker Panel 2 Potential Objects |
|---|---|
| T-cells (CD3) | Cytotoxic T-cells (CD8$^+$) |
| Cytotoxic T-cells (CD8$^+$) | Epithelial cells (EM$^+$ cell) |
| Epithelial cells (EM$^+$ cell) | Stromal cells (cell outside of endothelial region) |
| Stromal cells (cell outside of epithelial region) | PD-L1$^+$ cells |
| Macrophages (CD68$^+$) | PD-L1$^-$ cells |
| PD-L1$^+$ cells | PD-1$^+$ cells |
| PD-L1$^-$ cells | PD-1$^-$ cells |
| PD-L1$^+$ CTL (PD-L1$^+$ CD8$^+$); | LAG3$^+$ cells |
| PD-L1$^-$ CTL (PD-L1$^-$ CD8$^+$) | LAG3$^-$ cells |
| PD-L1$^+$ epithelial cell (PD-L1$^+$ EM$^+$ cell) | PD-1$^+$ CTL (PD-1$^+$ CD8$^+$); |
| PD-L1$^+$ Stroma (PD-L1$^+$ cell outside of epithelial region) | PD-1$^-$ CTL (PD-1$^-$ CD8$^+$) |
| | PD-1$^+$ cells within epithelial cell area (PD-1$^+$ cell within an Epithelial region) |
| PD-L1$^-$ epithelial cell (PD-L1$^-$ EM$^+$ cell) | |
| PD-L1$^-$ Stroma (PD-L1$^-$ outside of epithelial region) | PD-1$^+$ cells within stroma (PD-1$^+$ cell outside of epithelial region) |
| PD-L1$^+$ Macrophages (PD-L1$^+$ CD68$^+$) | PD-1$^-$ cells within epithelial cell area (PD-1$^-$ cell within an epithelial region) |
| PD-L1$^-$ Macrophages (PD-L1$^-$ CD68$^+$) | |
| PD-L1$^+$ T-cells (PD-L1$^+$ CD3$^+$) | PD-1$^-$ cells within Stroma (PD-1$^-$ cell outside of an Epithelial region) |
| PD-L1$^-$ T-cells (PD-L1$^-$ CD3$^+$) | PD-L1$^+$ CTL (PD-L1$^+$ CD8$^+$); |
| | PD-L1$^-$ CTL (PD-L1$^-$ CD8$^+$) |
| | PD-L1$^+$ epithelial cell (PD-L1$^+$ EM$^+$ cell) |
| | PD-L1$^+$ Stroma (PD-L1$^+$ cell outside of epithelial region) |
| | PD-L1$^-$ epithelial cell (PD-L1$^-$ EM$^+$ cell) |
| | PD-L1$^-$ Stroma (PD-L1$^-$ outside of epithelial region) |
| | PD-L1$^+$ cells within epithelial cell area (PD-L1$^+$ cell within an Epithelial region) |
| | PD-L1$^+$ cells within stroma (PD-L1$^+$ cell outside of EM$^+$ dense region) |
| | PD-L1$^-$ cells within epithelial cell area (PD-L1$^-$ cell within an Epithelial region) |
| | PD-L1$^-$ cells within Stroma (PD-L1$^-$ outside of an Epithelial region) |
| | LAG3$^+$ CTL (LAG3$^+$ CD8$^+$); |

TABLE 5-continued

| Biomarker Panel 1 Objects | Biomarker Panel 2 Potential Objects |
|---|---|
| | LAG3⁻ CTL (LAG3⁻ CD8⁺) |
| | LAG3⁺ cells within epithelial cell area (LAG3⁺ cell within an Epithelial region) |
| | LAG3⁺ cells within stroma (LAG3⁺ cell outside of EM⁺ dense region) |
| | LAG3⁻ cells within epithelial cell area (LAG3⁻ cell within an Epithelial region) |
| | LAG3⁻ cells within Stroma (LAG3⁻ outside of an Epithelial region) |

The image analysis system 300 may also pass the image to ROI generator 311. ROI generator 311 is used to identify the ROI or ROIs of the image from which the immune context score will be calculated. In cases where the object identifier 310 is not applied to the whole image, the ROI or ROIs generated by the ROI generator 311 may also be used to define a subset of the image on which object identifier 310 is executed.

In one embodiment, ROI generator 311 may be accessed through user-interface module 312. An image of the biomarker-stained sample (or a morphologically-stained serial section of the biomarker-stained sample) is displayed on a graphic user interface of the user interface module 112, and the user annotates one or more region(s) in the image to be considered ROIs. ROI annotation can take a number of forms in this example. For example, the user may manually define the ROI (referred to hereafter as "manual ROI annotation"). In other examples, the ROI generator 311 may assist the user in annotating the ROI (termed, "semi-automated ROI annotation"). For example, the user may delineate one or more regions on the digital image, which the system then automatically transforms into a complete ROI. For example, if the desired ROI is a tumor region, a user delineates the tumor region, and the system identifies similar morphological regions by, for example, using computer vision and machine learning. As another example, the user could annotate an edge in the image (for example, by tracing a line defining the invasive front of the tumor), and ROI generator 311 may automatically define an ROI based on the user-defined edge. For example, the user may annotate the edge of the invasive front or the tumor region in user-interface module 312, and the ROI generator 311 creates an ROI using the edge as a guide, for example, by drawing an ROI encompassing all objects within a predefined distance of the edge (for example, a PT ROI), or within a predefined distance of one side of the edge (for example, a PO or PI ROI), or within a first predefined distance on a first side of the edge and within a second predefined distance on a second side of the edge (for example, a PT ROI wherein the inner and outer portions thereof have different standard distances from the invasive front).

In other embodiments, ROI generator 311 may automatically suggest an ROI without any direct input from the user (for example, by applying a tissue segmentation function to an unannotated image), which the user may then chose to accept, reject, or edit as appropriate.

In some embodiments, ROI generator 311 may also include a registration function, whereby an ROI annotated in one section of a set of serial sections is automatically transferred to other sections of the set of serial sections. This functionality is especially useful when an H & E-stained serial section is provided along with the biomarker-labeled sections. In such an embodiment, the user may draw, for example, the tumor region in the digital image of the H & E-stained section. The ROI generator 311 then registers the ROI from the H & E image to the image of the biomarker-stained serial section, matching the tissue structures from the H & E image to the corresponding tissue structures in the serial section. Exemplary registration methods can be found at, for example, WO2013/140070 and US 2016-0321809

Figure 4B:
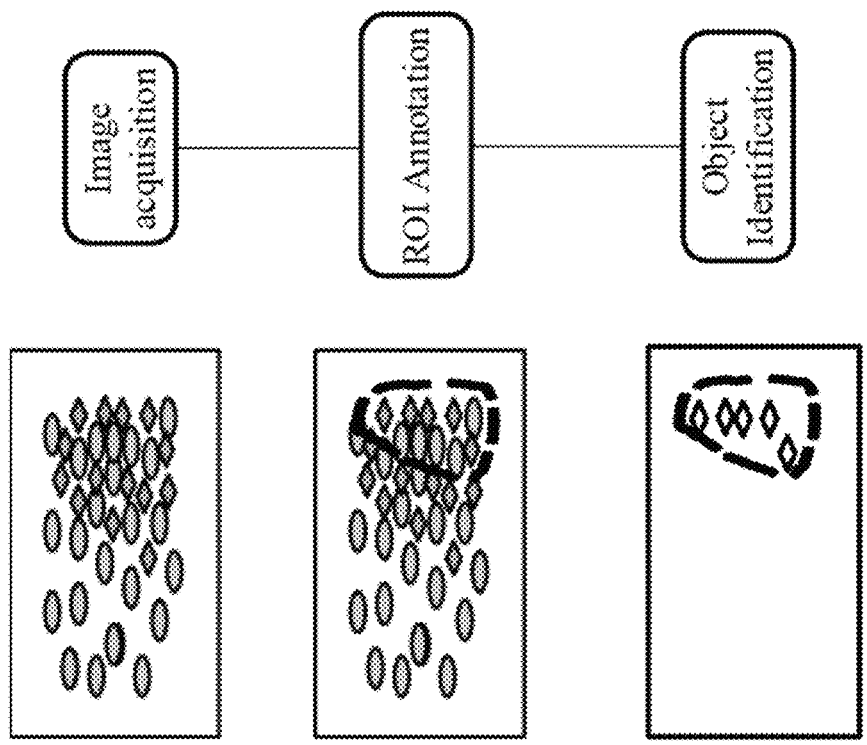
FIG. 4B illustrates an exemplary workflow implemented on an image analysis system as disclosed herein, wherein the object identification function is executed on only the ROI after the ROI generator function is executed.
Figure 4A:
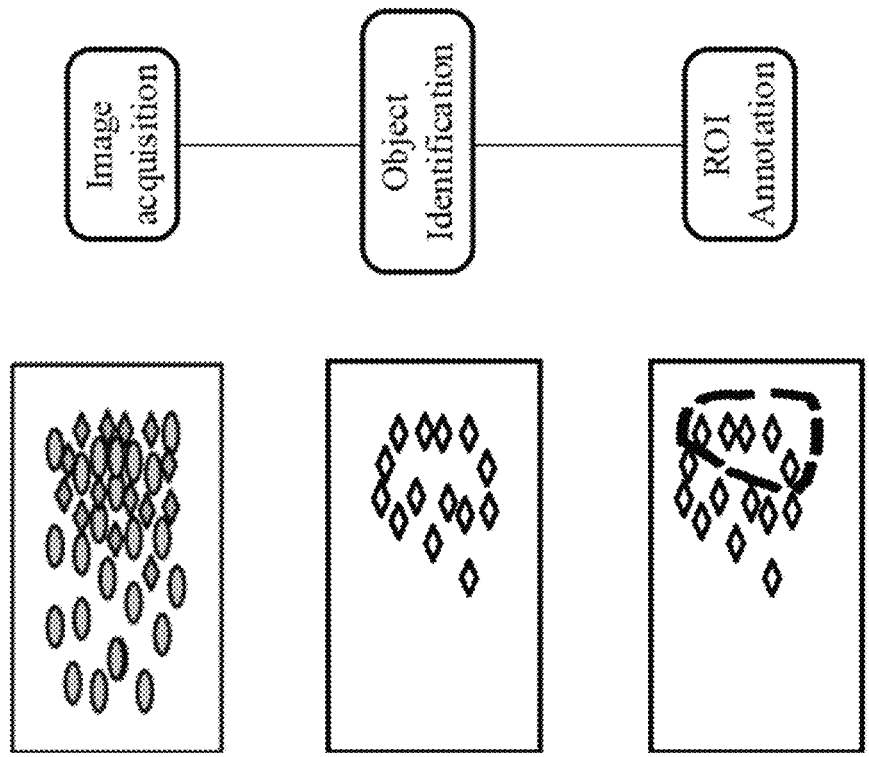
FIG. 4A illustrates an exemplary workflow implemented on an image analysis system as disclosed herein, wherein the object identification function is executed on the whole image before the ROI generator function is executed.

The object identifier 310 and the ROI generator 311 may be implemented in any order. For example, the object identifier 310 may be applied to the entire image first. The positions and features of the identified objects can then be stored and recalled later when the ROI generator 311 is implemented. In such an arrangement, a score can be generated by the scoring engine 313 immediately upon generation of the ROI. Such a workflow is illustrated at FIG. 3A. As can be seen at FIG. 4A, an image is obtained having a mixture of different object (illustrated by dark ovals and dark diamonds). After object identification task is implemented, all diamonds in the image are identified (illustrated by open diamonds). When the ROI is appended to the image (illustrated by the dashed line), only the diamonds located in the ROI region are included in the metric calculation for the ROI. A feature vector is then calculated including the feature metric and any additional metrics used by the scoring function executed by the scoring engine 313. Alternatively, the ROI generator 311 can be implemented first. In this work flow, the object identifier 310 may be implemented only on the ROI (which minimizes computation time), or it may still be implemented on the whole image (which would allow on-the-fly adjustments without re-running the object identifier 310). Such a workflow is illustrated at FIG. 4B. As can be seen at FIG. 4B, an image is obtained having a mixture of different object (illustrated by dark ovals and dark diamonds). The ROI is appended to the image (illustrated by the dashed line), but no objects have been marked yet. After object identification task is implemented on the ROI, all diamonds in the ROI are identified (illustrated by open diamonds) and included in the feature metric calculation for the ROI. A feature vector is then calculated including the feature metric(s) and any additional metrics used by the scoring function executed by the scoring engine 313. It may also be possible to implement the object identifier 310 and ROI generator 311 simultaneously.

After both the object identifier 310 and ROI generator 311 have been implemented, a scoring engine 313 is implemented. The scoring engine 313 calculates feature metric(s) for the ROI, and, if being used, pre-determined maximum and/or minimum cutoffs. A feature vector including the calculated feature metrics and any other variable used by the scoring function is assembled by the scoring engine and the scoring function is applied to the feature vector.

Specific exemplary features for each panel are set forth in Table 6:

TABLE 6

| Panel 1<br>(CD8; EM; CD68; CD3; PD-L1) | Panel 2<br>(CD8; EM; PD-L1; PD-1; LAG3) |
|---|---|
| T.CD8–PDL1+CD68 Dist; | 'number of PD1 positive cells in EM positive area'; |
| T.CD8–PDL1+CD3All Dist; | 'number of PD1 positive cells in EM negative area'; |
| T.EM–CD8 Dist; | 'number of PD1+ EM+ cells divided by area of EM positive cells'; |
| T.No.PDL1+EM in10 μm CD8; | |
| T.No.PDL1+EM in30 μm CD8; | 'number of PD1+ EM– cells divided by area of EM negative cells'; |
| T.No.CD8 in10 μm EM; | |
| T.No.CD8 in30 μm EM; | 'number of PDL1 positive cells in EM positive area'; |
| Epith.CD8toPDL1+CD68 Dist; | |
| Epith.CD8toPDL1+CD3All Dist; | 'number of PDL1 positive cells in EM negative area'; |
| Epith.EMtoCD8 Dist; | |
| Epith.No. PDL1+EM in10 μm CD8; | 'number of PDL1+ EM+ cells divided by area of EM positive cells'; |
| Epith.No.PDL1+EM in30 μm CD8; | |
| Epith.No.CD8 in 10 μm EM; | 'number of PDL1+ EM– cells divided by area of EM negative cells'; |
| Epith.No.CD8 in30 μm EM; | |
| Str.CD8toPDL1+CD68 Dist; | 'number of CD8 positive cells in EM positive area'; |
| Str.CD8toPDL1+CD3All Dist; | 'number of CD8 positive cells in EM negative area'; |
| Str.EMtoCD8 Dist; | 'number of CD8+ EM+ cells divided by area of EM positive cells'; |
| Str.No.PDL1+EM in10 μm CD8; | |
| Str.No.PDL1+EM in30 μm CD8; | 'number of CD8+ EM– cells divided by area of EM negative cells'; |
| Str.No.CD8 in10 μm EM; | |
| Str.No.CD8 in30 μm EM; | 'number of Lag3 positive cells in EM positive area'; |
| PI.CD8toPDL1+CD68 Dist; | 'number of Lag3 positive cells in EM negative area'; |
| PI.CD8toPDL1+CD3All Dist; | 'number of Lag3+ EM+ cells divided by area of EM positive cells'; |
| PI.EMtoCD8 Dist; | |
| PI.No.PDL1+EM in10 μm CD8; | 'number of Lag3+ EM– cells divided by area of EM negative cells'; |
| PI.No.PDL1+EM in30 μm CD8; | |
| PI.No.CD8 in10 μm EM; | 'number of Lag3 positive cells in EM positive area'; |
| PI.No.CD8 in30 μm EM; | 'number of Lag3 positive cells in EM negative area'; |
| PO.CD8toPDL1+CD68 Dist; | 'number of Lag3+ EM+ cells divided by area of EM positive cells'; |
| PO.CD8toPDL1+CD3All Dist; | |
| PO.EMtoCD8 Dist; | 'number of Lag3+ EM– cells divided by area of EM negative cells'; |
| PO.No.PDL1+EM in10 μm CD8; | |
| PO.No.PDL1+EM in30 μm CD8; | 'ratio of number of PD1+&CD8+ to CD8+ cell in EM positive area'; |
| PO.No.CD8 in10 μm EM; | |
| PO.No.CD8 in30 μm EM; | 'ratio of number of PD1+&CD8+ to CD8+ cell in EM negative area'; |
| PDL1+CD3All density in T; | |
| PDL1+CD3+CD8– density in T; | 'ratio of number of PD1–&CD8+ to CD8+ cell in EM positive area'; |
| PDL1+CD8+ density in T; | |
| PDL1+CD68+ density in T; | 'ratio of number of PD1–&CD8+ to CD8+ cell in EM negative area'; |
| PDL1+EM+ density in T; | |
| CD3All density in T; | 'ratio of number of Lag3+&CD8+ to CD8+ cell in EM positive area'; |
| CD8+ density in T; | |
| CD68+ density in T; | 'ratio of number of Lag3+&CD8+ to CD8+ cell in EM negative area'; |
| EM+ density in T; | |
| PDL1+CD3All density in Epith; | 'ratio of number of Lag3–&CD8+ to CD8+ cell in EM positive area'; |
| PDL1+CD3+CD8– density in Epith; | |
| PDL1+CD8+ density in Epith; | 'ratio of number of Lag3–&CD8+ to CD8+ cell in EM negative area'; |
| PDL1+CD68+ density in Epith; | |
| PDL1+EM+ density in Epith; | 'ratio of number of PDL1+&CD8+ to CD8+ cell in EM positive area'; |
| CD3All density in Epith; | |
| CD8+ density in Epith; | 'ratio of number of PDL1+&CD8+ to CD8+ cell in EM negative area'; |
| CD68+ density in Epith; | |
| EM+ density in Epith; | 'ratio of number of PDL1–&CD8+ to CD8+ cell in EM positive area'; |
| PDL1+CD3All density in Str; | |
| PDL1+CD3+CD8– density in Str; | 'ratio of number of PDL1–&CD8+ to CD8+ cell in EM negative area'; |
| PDL1+CD8+ density in Str; | |
| PDL1+CD68+ density in Str; | 'ratio of number of PD1+&Lag3+&CD8+ to CD8+ cell in EM positive area'; |
| PDL1+EM+ density in Str; | |
| CD3All density in Str; | 'ratio of number of PD1+&Lag3+&CD8+ to CD8+ cell in EM negative area'; |
| CD8+ density in Str; | |
| CD68+ density in Str; | 'ratio of number of PD1+&PDL1+&CD8+ to CD8+ cell in EM positive area'; |
| EM+ density in Str; | |
| PDL1+CD3All density in PI; | 'ratio of number of PD1+&PDL1+&CD8+ to CD8+ cell in EM negative area'; |
| PDL1+CD3+CD8– density in PI; | |
| PDL1+CD8+ density in PI; | 'ratio of number of PD1+&PDL1+&Lag3+&CD8+ to CD8+ cell in EM positive area'; |
| PDL1+CD68+ density in PI; | 'ratio of number of PD1+&PDL1+&Lag3+&CD8+ to CD8+ cell in EM negative area'; |
| PDL1+EM+ density in PI; | 'ratio of number of PD1-&PDL1+&Lag3+&CD8+ to CD8+ cell in EM positive area'; |
| CD3All density in PI; | |
| CD8+ density in PI; | 'ratio of number of PD1–&PDL1+&Lag3+&CD8+ to CD8+ cell in EM negative area'; |
| CD68+ density in PI; | |
| EM+ density in PI; | 'ratio of number of PD1+&PDL1–&Lag3+&CD8+ to CD8+ cell in EM positive area'; |
| PDL1+CD3All density in PO; | |
| PDL1+CD3+CD8– density in PO; | 'ratio of number of PD1+&PDL1–&Lag3+&CD8+ to CD8+ cell in EM negative area'; |
| PDL1+CD8+ density in PO; | |
| PDL1+CD68+ density in PO; | 'mean value of all cell PD1 intensity'; |
| PDL1+EM+ density in PO; | 'variance of all cell PD1 intensity'; |
| CD3All density in PO; | 'min value of all cell PD1 intensity'; |

TABLE 6-continued

| Panel 1<br>(CD8; EM; CD68; CD3; PD-L1) | Panel 2<br>(CD8; EM; PD-L1; PD-1; LAG3) |
|---|---|
| CD8+ density in PO;<br>CD68+ density in PO;<br>EM+ density in PO;<br>PDL1+EM+ area ratio in T;<br>EM+ area ratio in T;<br>PDL1+EM+ area ratio in Epith;<br>EM+ area ratio in Epith;<br>PDL1+EM+ area ratio in Str;<br>EM+ area ratio in Str;<br>PDL1+EM+ area ratio in PI;<br>EM+ area ratio in PI;<br>PDL1+EM+ area ratio in PO;<br>EM+ area ratio in PO;<br>PDL1+EM/EM in T;<br>PDL1+EM/EM in Epith;<br>PDL1+EM/EM in Str;<br>PDL1+EM/EM in PI;<br>PDL1+EM/EM in PO;<br>PDL1+CD3All/CD3All in T;<br>PDL1+CD3All/CD3All in Epith;<br>PDL1+CD3All/CD3All in Str;<br>PDL1+CD3All/CD3All in PI;<br>PDL1+CD3All/CD3All in PO;<br>PDL1+CD3+CD8−/CD3+CD8− in T;<br>PDL1+CD3+CD8−/CD3+CD8− in Epith;<br>PDL1+CD3+CD8−/CD3+CD8− in Str;<br>PDL1+CD3+CD8−/CD3+CD8− in PI;<br>PDL1+CD3+CD8−/CD3+CD8− in PO;<br>PDL1+CD8+/CD8+ in T;<br>PDL1+CD8+/CD8+ in Epith;<br>PDL1+CD8+/CD8+ in Str;<br>PDL1+CD8+/CD8+ in PI;<br>PDL1+CD8+/CD8+ in PO;<br>PDL1+CD68+/CD68+ in T;<br>PDL1+CD68+/CD68+ in Epith;<br>PDL1+CD68+/CD68+ in Str;<br>PDL1+CD68+/CD68+ in PI;<br>PDL1+CD68+/CD68+ in PO;<br>CD3+CD8−/CD3All in T;<br>CD3+CD8−/CD3All in Epith;<br>CD3+CD8−/CD3All in Str;<br>CD3+CD8−/CD3All in PI;<br>CD3+CD8−/CD3All in PO;<br>CD3All density in EM in T;<br>CD3All density in EM in Epith;<br>CD3All density in EM in PI;<br>CD8 density in EM in T;<br>CD8 density in EM in Epith;<br>CD8 density in EM in PI;<br>CD3 Aggregate Area;<br>CD8 Aggregate Area | 'max value of all cell PD1 intensity';<br>'mean value of CD8+ cell PD1 intensity';<br>'variance of CD8+ cell PD1 intensity';<br>'min value of CD8+ cell PD1 intensity';<br>'max value of CD8+ cell PD1 intensity';<br>'mean value of all cell PDL1 intensity';<br>'variance of all cell PDL1 intensity';<br>'min value of all cell PDL1 intensity';<br>'max value of all cell PDL1 intensity';<br>'mean value of CD8+ cell PDL1 intensity';<br>'variance of CD8+ cell PDL1 intensity';<br>'min value of CD8+ cell PDL1 intensity';<br>'max value of CD8+ cell PDL1 intensity';<br>'mean value of EM+ cell PDL1 intensity';<br>'variance of EM+ cell PDL1 intensity';<br>'min value of EM+ cell PDL1 intensity';<br>'max value of EM+ cell PDL1 intensity';<br>'mean value of all cell Lag3 intensity';<br>'variance of all cell Lag3 intensity';<br>'min value of all cell Lag3 intensity';<br>'max value of all cell Lag3 intensity';<br>'mean value of CD8+ cell Lag3 intensity';<br>'variance of CD8+ cell Lag3 intensity';<br>'min value of CD8+ cell Lag3 intensity';<br>'max value of CD8+ cell Lag3 intensity';<br>'mean number of PD1 within 10 μm radius of PDL1';<br>'variance of number of PD1 within 10 μm radius of PDL1';<br>'min number of PD1 within 10 μm radius of PDL1';<br>'max number of PD1 within 10 μm radius of PDL1';<br>'mean number of PD1 within 20 μm radius of PDL1';<br>'variance of number of PD1 within 20 μm radius of PDL1';<br>'min number of PD1 within 20 μm radius of PDL1';<br>'max number of PD1 within 20 μm radius of PDL1';<br>'mean number of PDL1 within 10 μm radius of PD1';<br>'variance of number of PDL1 within 10 μm radius of PD1';<br>'min number of PDL1 within 10 μm radius of PD1';<br>'max number of PDL1 within 10 μm radius of PD1';<br>'mean number of PDL1 within 20 μm radius of PD1';<br>'variance of number of PDL1 within 20 μm radius of PD1';<br>'min number of PDL1 within 20 μm radius of PD1';<br>'max number of PDL1 within 20 μm radius of PD1';<br>'mean number of PD1+&CD8+ within 10 μm radius of PDL1';<br>'variance of number of PD1+&CD8+ within 10 μm radius of PDL1';<br>'min number of PD1+&CD8+ within 10 μm radius of PDL1';<br>'max number of PD1+&CD8+ within 10 μm radius of PDL1';<br>'mean number of PD1+&CD8+ within 20 μm radius of PDL1';<br>'variance of number of PD1+&CD8+ within 20 μm radius of PDL1';<br>'min number of PD1+&CD8+ within 20 μm radius of PDL1';<br>'max number of PD1+&CD8+ within 20 μm radius of PDL1';<br>'mean number of PD1+&CD8+ within 10 μm radius of PDL1+&EM+';<br>'variance of number of PD1+&CD8+ within 10 μm radius of PDL1+&EM+';<br>'min number of PD1+&CD8+ within 10 μm radius of PDL1+&EM+';<br>'max number of PD1+&CD8+ within 10 μm radius of PDL1+&EM+';<br>'mean number of PD1+&CD8+ within 20 μm radius of PDL1+&EM+';<br>'variance of number of PD1+&CD8+ within 20 μm radius of PDL1+&EM+'; |

TABLE 6-continued

| Panel 1<br>(CD8; EM; CD68; CD3; PD-L1) | Panel 2<br>(CD8; EM; PD-L1; PD-1; LAG3) |
|---|---|
| | 'min number of PD1+&CD8+ within 20 μm radius of PDL1+&EM+';<br>'max number of PD1+&CD8+ within 20 μm radius of PDL1+&EM+';<br>'mean number of PD1+&CD8+ within 10 μm radius of PDL1+&CD8+';<br>'variance of number of PD1+&CD8+ within 10 μm radius of PDL1+&CD8+';<br>'min number of PD1+&CD8+ within 10 μm radius of PDL1+&CD8+';<br>'max number of PD1+&CD8+ within 10 μm radius of PDL1+&CD8+';<br>'mean number of PD1+&CD8+ within 20 μm radius of PDL1+&CD8+';<br>'variance of number of PD1+&CD8+ within 20 μm radius of PDL1+&CD8+';<br>'min number of PD1+&CD8+ within 20 μm radius of PDL1+&CD8+';<br>'max number of PD1+&CD8+ within 20 μm radius of PDL1+&CD8+';<br>'mean number of PD1Low&CD8+ within 10 μm radius of PDL1';<br>'variance of number of PD1Low&CD8+ within 10 μm radius of PDL1';<br>'min number of PD1Low&CD8+ within 10 μm radius of PDL1';<br>'max number of PD1Low&CD8+ within 10 μm radius of PDL1';<br>'mean number of PD1Low&CD8+ within 20 μm radius of PDL1';<br>'variance of number of PD1Low&CD8+ within 20 μm radius of PDL1';<br>'min number of PD1Low&CD8+ within 20 μm radius of PDL1';<br>'max number of PD1Low&CD8+ within 20 μm radius of PDL1';<br>'mean number of PD1Low&CD8+ within 10 μm radius of PDL1+&EM+';<br>'variance of number of PD1Low&CD8+ within 10 μm radius of PDL1+&EM+';<br>'min number of PD1Low&CD8+ within 10 μm radius of PDL1+&EM+';<br>'max number of PD1Low&CD8+ within 10 μm radius of PDL1+&EM+';<br>'mean number of PD1Low&CD8+ within 20 μm radius of PDL1+&EM+';<br>'variance of number of PD1Low&CD8+ within 20 μm radius of PDL1+&EM+';<br>'min number of PD1Low&CD8+ within 20 μm radius of PDL1+&EM+';<br>'max number of PD1Low&CD8+ within 20 μm radius of PDL1+&EM+';<br>'mean number of PD1Low&CD8+ within 10 μm radius of PDL1+&CD8+';<br>'variance of number of PD1Low&CD8+ within 10 μm radius of PDL1+&CD8+';<br>'min number of PD1Low&CD8+ within 10 μm radius of PDL1+&CD8+';<br>'max number of PD1Low&CD8+ within 10 μm radius of PDL1+&CD8+';<br>'mean number of PD1Low&CD8+ within 20 μm radius of PDL1+&CD8+';<br>'variance of number of PD1Low&CD8+ within 20 μm radius of PDL1+&CD8+';<br>'min number of PD1Low&CD8+ within 20 μm radius of PDL1+&CD8+';<br>'max number of PD1Low&CD8+ within 20 μm radius of PDL1+&CD8+';<br>'mean number of PD1Med&CD8+ within 10 μm radius of PDL1';<br>'variance of number of PD1Med&CD8+ within 10 μm radius of PDL1';<br>'min number of PD1Med&CD8+ within 10 μm radius of PDL1';<br>'max number of PD1Med&CD8+ within 10 μm radius of PDL1'; |

TABLE 6-continued

| Panel 1<br>(CD8; EM; CD68; CD3; PD-L1) | Panel 2<br>(CD8; EM; PD-L1; PD-1; LAG3) |
|---|---|
| | 'mean number of PD1Med&CD8+ within 20 µm radius of PDL1';
'variance of number of PD1Med&CD8+ within 20 µm radius of PDL1';
'min number of PD1Med&CD8+ within 20 µm radius of PDL1';
'max number of PD1Med&CD8+ within 20 µm radius of PDL1';
'mean number of PD1Med&CD8+ within 10 µm radius of PDL1+&EM+';
'variance of number of PD1Med&CD8+ within 10 µm radius of PDL1+&EM+';
'min number of PD1Med&CD8+ within 10 µm radius of PDL1+&EM+';
'max number of PD1Med&CD8+ within 10 µm radius of PDL1+&EM+';
'mean number of PD1Med&CD8+ within 20 µm radius of PDL1+&EM+';
'variance of number of PD1Med&CD8+ within 20 µm radius of PDL1+&EM+';
'min number of PD1Med&CD8+ within 20 µm radius of PDL1+&EM+';
'max number of PD1Med&CD8+ within 20 µm radius of PDL1+&EM+';
'mean number of PD1Med&CD8+ within 10 µm radius of PDL1+&CD8+';
'variance of number of PD1Med&CD8+ within 10 µm radius of PDL1+&CD8+';
'min number of PD1Med&CD8+ within 10 µm radius of PDL1+&CD8+';
'max number of PD1Med&CD8+ within 10 µm radius of PDL1+&CD8+';
'mean number of PD1Med&CD8+ within 20 µm radius of PDL1+&CD8+';
'variance of number of PD1Med&CD8+ within 20 µm radius of PDL1+&CD8+';
'min number of PD1Med&CD8+ within 20 µm radius of PDL1+&CD8+';
'max number of PD1Med&CD8+ within 20 µm radius of PDL1+&CD8+';
'mean number of PD1High&CD8+ within 10 µm radius of PDL1';
'variance of number of PD1High&CD8+ within 10 µm radius of PDL1';
'min number of PD1High&CD8+ within 10 µm radius of PDL1';
'max number of PD1High&CD8+ within 10 µm radius of PDL1';
'mean number of PD1High&CD8+ within 20 µm radius of PDL1';
'variance of number of PD1High&CD8+ within 20 µm radius of PDL1';
'min number of PD1High&CD8+ within 20 µm radius of PDL1';
'max number of PD1High&CD8+ within 20 µm radius of PDL1';
'mean number of PD1High&CD8+ within 10 µm radius of PDL1+&EM+';
'variance of number of PD1High&CD8+ within 10 µm radius of PDL1+&EM+';
'min number of PD1High&CD8+ within 10 µm radius of PDL1+&EM+';
'max number of PD1High&CD8+ within 10 µm radius of PDL1+&EM+';
'mean number of PD1High&CD8+ within 20 µm radius of PDL1+&EM+';
'variance of number of PD1High&CD8+ within 20 µm radius of PDL1+&EM+';
'min number of PD1High&CD8+ within 20 µm radius of PDL1+&EM+';
'max number of PD1High&CD8+ within 20 µm radius of PDL1+&EM+';
'mean number of PD1High&CD8+ within 10 µm radius of PDL1+&CD8+'; |

TABLE 6-continued

| Panel 1<br>(CD8; EM; CD68; CD3; PD-L1) | Panel 2<br>(CD8; EM; PD-L1; PD-1; LAG3) |
|---|---|
| | 'variance of number of PD1High&CD8+ within 10 µm radius of PDL1+&CD8+';<br>'min number of PD1High&CD8+ within 10 µm radius of PDL1+&CD8+';<br>'max number of PD1High&CD8+ within 10 µm radius of PDL1+&CD8+';<br>'mean number of PD1High&CD8+ within 20 µm radius of PDL1+&CD8+';<br>'variance of number of PD1High&CD8+ within 20 µm radius of PDL1+&CD8+';<br>'min number of PD1High&CD8+ within 20 µm radius of PDL1+&CD8+';<br>'max number of PD1High&CD8+ within 20 µm radius of PDL1+&CD8+';<br>'number of co-expressed PD1/PDL1 cells';<br>'number of co-expressed PD1PosCD8Pos/PDL1 cells';<br>'average distance from PD1 to its nearest PDL1';<br>'average distance from PD1Pos&CD8Pos to its nearest PDL1';<br>'average distance from PDL1 to its nearest PD1';<br>'std of distance from PD1 to its nearest PDL1';<br>'std of distance from PD1 to its nearest PDL1';<br>'std of distance from PDL1 to its nearest PD1' |

As depicted in FIG. 3, in some embodiments image analysis system 300 may be communicatively coupled to an image acquisition system 320. Image acquisition system 320 may obtain images of samples and provide those images to image analysis system 300 for analysis and presentation to the user.

Image acquisition system 320 may include a scanning platform 325 such as a slide scanner that can scan the stained slides at 20×, 40×, or other magnifications to produce high resolution whole-slide digital images, including for example slide scanners. At a basic level, the typical slide scanner includes at least: (1) a microscope with lens objectives, (2) a light source (such as halogen, light emitting diode, white light, and/or multispectral light sources, depending on the dye), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., *Whole slide imaging in pathology: advantages, limitations, and emerging perspectives*, Pathology and Laboratory Medicine Int'l, Vol. 7, p. 23-33 (June 2015), the content of which is incorporated by reference in its entirety. Examples of commercially available slide scanners include: 3DHistech PANORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VIA, and VL120; PerkinElmerLAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

Images generated by scanning platform 325 may be transferred to image analysis system 300 or to a server or database accessible by image analysis system 300. In some embodiments, the images may be transferred automatically via one or more local-area networks and/or wide-area networks. In some embodiments, image analysis system 300 may be integrated with or included in scanning platform 325 and/or other modules of image acquisition system 320, in which case the image may be transferred to image analysis system, e.g., through a memory accessible by both platform 325 and system 320. In some embodiments, image acquisition system 320 may not be communicatively coupled to image analysis system 300, in which case the images may be stored on a non-volatile storage medium of any type (e.g., a flash drive) and downloaded from the medium to image analysis system 300 or to a server or database communicatively coupled thereto. In any of the above examples, image analysis system 300 may obtain an image of a biological sample, where the sample may have been affixed to a slide and stained by histochemical staining platform 323, and where the slide may have been scanned by a slide scanner or another type of scanning platform 325. It is appreciated, however, that in other embodiments, below-described techniques may also be applied to images of biological samples acquired and/or stained through other means.

Image acquisition system 320 may also include an automated histochemical staining platform 323, such as an automated IHC/ISH slide stainer. Automated IHC/ISH slide stainers typically include at least: reservoirs of the various reagents used in the staining protocols, a reagent dispense unit in fluid communication with the reservoirs for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, Overview of Automated Immunohistochemistry, Arch Pathol Lab Med., Vol. 138, pp. 1578-1582 (2014), incorporated herein by reference in its entirety, describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform 323.

Image acquisition system 320 may also include an automated H & E staining platform 324. Automated systems for performing H & E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H & E stainers include the VENTANA SYMPHONY (individual slide stainer) and VENTANA HE 600 (individual slide stainer) series H & E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H & E stainers from Leica Biosystems Nussloch GmbH. H & E staining platform 324 is typically used in workflows in which a morphologically-stained serial section of the biomarker-stained section(s) is desired.

The scoring system may further include a laboratory information system (LIS) 330. LIS 330 typically performs one or more functions selected from: recording and tracking processes performed on samples and on slides and images derived from the samples, instructing different components of the scoring system to perform specific processes on the samples, slides, and/or images, and track information about specific reagents applied to samples and or slides (such as lot numbers, expiration dates, volumes dispensed, etc.). LIS 330 usually comprises at least a database containing information about samples; labels associated with samples, slides, and/or image files (such as barcodes (including 1-dimensional barcodes and 2-dimensional barcodes), radio frequency identification (RFID) tags, alpha-numeric codes affixed to the sample, and the like); and a communication device that reads the label on the sample or slide and/or communicates information about the slide between the LIS 330 and the other components of the immune context scoring system. Thus, for example, a communication device could be placed at each of a sample processing station, automated histochemical stainer 323, H & E staining platform 324, and scanning platform 325. When the sample is initially processed into sections, information about the sample (such as patient ID, sample type, processes to be performed on the section(s)) may be entered into the communication device, and a label is created for each section generated from the sample. At each subsequent station, the label is entered into the communication device (such as by scanning a barcode or RFID tag or by manually entering the alpha-numeric code), and the station electronically communicates with the database to, for example, instruct the station or station operator to perform a specific process on the section and/or to record processes being performed on the section. At scanning platform 325, the scanning platform 325 may also encode each image with a computer-readable label or code that correlates back to the section or sample from which the image is derived, such that when the image is sent to the image analysis system 300, image processing steps to be performed may be sent from the database of LIS 330 to the image analysis system and/or image processing steps performed on the image by image analysis system 300 are recorded by database of LIS 330. Commercially available LIS systems useful in the present methods and systems include, for example, VENTANA Vantage Workflow system (Roche).

Examples

I. Characterization of PD-L1, CD8, CD3, CD68 and PanCK In Tumor Microenvironment of GI Tract Tumors with Respect to Patients' Mismatch Repair Status and Anti-PD-1 Treatment Outcome Using 5Plex IHC and Whole Slide Image Analysis I.A. Background There is increasing need to understand the tumor microenvironment to guide cancer immunotherapy. Multiplexed immunohistochemistry (IHC) enables the characterization of tumor microenvironments by detecting multiple biomarkers and their co-expression on a single slide while preserving tissue morphology. Extracting information about co-expression of multiple biomarkers and their spatial relationships requires whole slide image analysis algorithms that are tailored to individual assays and their intended uses. Cancers may escape immune surveillance and eradication through the up-regulation of the programmed death 1 (PD-1) pathway, and its ligand, programmed death-ligand 1 (PD-L1), on tumor cells and in the tumor microenvironment. Blockade of this pathway with antibodies to PD-1 or PD-L1 has led to remarkable clinical responses in some cancer patients.

Mismatch repair (MMR) deficiency predicts response of solid tumors to PD-1 blockade. However, not all patients with mismatch repair deficiency respond to the PD-blockade treatment. To understand the different responses, we evaluated the tumor micro environment by detecting PD-L1 expression in relationship with tumor cells and tumor infiltrating immune cells.

I.B. Samples, Staining, and Image Acquisition

A cohort of 60 pre-treatment (anti-PD-1 pembrolizumab) patient gastrointestinal tract tumor specimens with acceptable image and tissue quality for automated analysis was available to this study. After eliminating the non-evaluable responses, 54 cases were left. Table 7 shows the breakdown of responses with respect to mismatch repair deficiency.

TABLE 7

|  | Mismatch Repair Proficient | Mismatch Repair Deficient |
| --- | --- | --- |
| Progressive disease | 13 | 5 |
| Stable disease | 3 | 10 |
| Partial response + complete response | 1 | 22 |

Samples were formalin fixed, paraffin embedded, sectioned, and mounted on microscope slides.

Slides were stained in a multiplex format on a BenchMark ULTRA IHC/ISH automated slide stainer with fluorescent tyramide dye conjugates in a tyramide signal amplification procedure as set forth in Table 8:

TABLE 8

|  | Primary antibody | Secondary antibody | Tyramide conjugate | Cells of Interest |
| --- | --- | --- | --- | --- |
| 1 | CD8 (SP239) rabbit monoclonal | Goat anti-rabbit HRP | Rhodamine-6-G | Cytotoxic T-cells |
| 2 | PanCK mouse monoclonal | Goat anti-mouse HRP | N,N'-dicyclohexyl-carbodiimide (DCC) | Epithelial cells |
| 3 | CD68 (SP251) rabbit monoclonal | Goat anti-rabbit HRP | Red610 | Tissue macrophages |
| 4 | CD3 (SP162) rabbit monoclonal | Goat anti-rabbit HRP | SulfoCy5 | T-cells |
| 5 | PD-L1 (SP263) rabbit monoclonal | Goat anti-rabbit HRP | FAM | PD-L1-positive cells |

Figure 5:
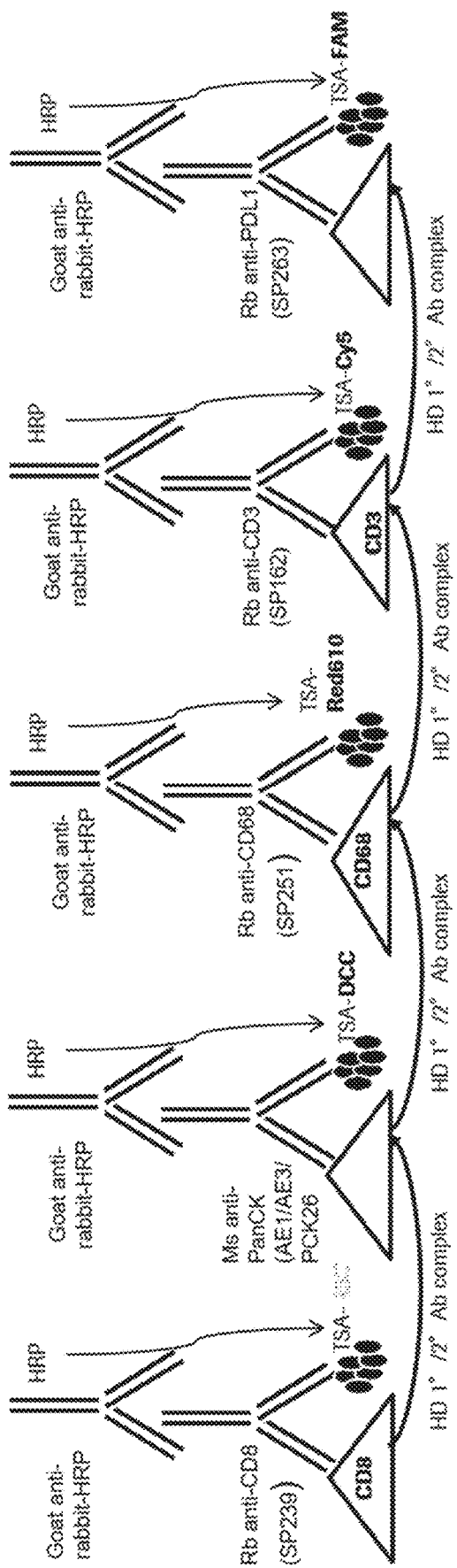
FIG. 5 illustrates the multiplex staining process using panel 1 as described in Example I.
Figure 6:
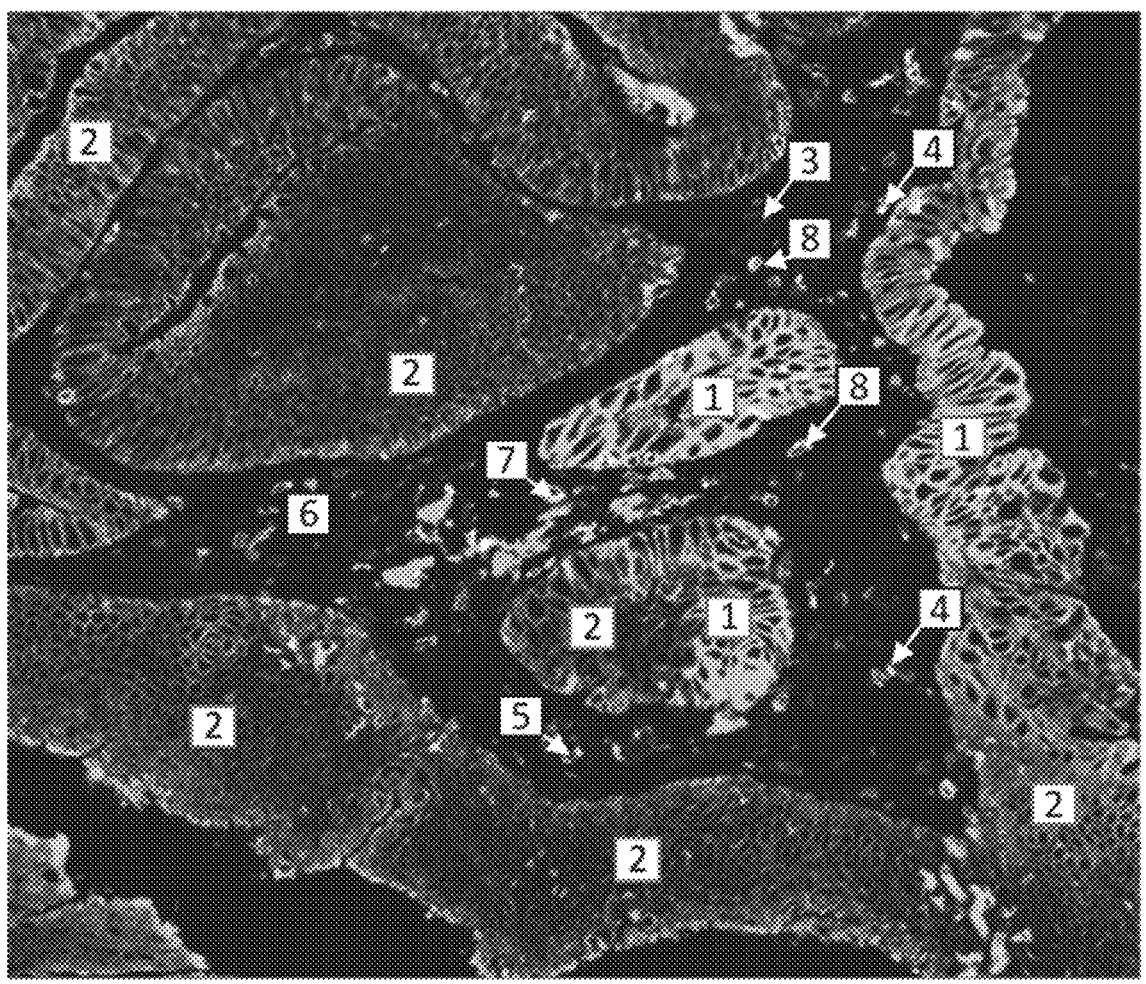
FIG. 6 illustrates an exemplary slide stained with panel 1.

The general concept of tyramide signal amplification is described by U.S. Pat. No. 6,593,100. The staining procedure is essentially the same as that described by Zhang I. Stains were applied sequentially as illustrated at FIG. 5. After each stain deposition a heat kill step was applied, comprising a process as described by Zhang I. An exemplary stained slide is illustrated at FIG. 6. A serial section of each sample was also stained for H & E using a VENTANA HE 600 automated slide stainer.

IHC-stained slides were scanned on a Zeiss AxioScan Z1 slide scanner and H & E stained slides were scanned on a VENTANA ISCAN COREO slide scanner. All images were exported into DPath, a proprietary digital pathology image analysis suite software suite from Roche.

I.C. Image Annotation and ROI Generation

A tumor region ROI and an invasive front of the tumor (if available) were annotated in the images by a pathologist. Additionally, necrotic regions and other regions to be excluded from analysis were annotated by the pathologist.

The DPath system automatically annotated epithelial tumor ROIs from aggregates of panCK+ cells, and stromal regions. First, the tumor area was subdivided into tiles. For each tile, a panCK mask was first generated by labelling each panCK+ cell and finding a union between the labelled cells. Post-processing was then performed on the mask to compensate for lymphocytes infiltrate by:
  (a) performing a morphological closing operation was with a 10-pixel radius disk-shaped structuring element (the resolution is 0.325 μms per pixel);
  (b) closing any holes within the mask greater than 80 pixels (8.5 μm$^2$) to generate a "PanCK mask with holes filled."
  (c) converting the PanCK mask with holes filled to a polygon.

The polygons from all of the tiles were then assembled to create polygons at the whole slide level. The whole slide level polygon was then converted to a mask at a lower resolution (reduced size by 3^3), and dilate by 8.8 μm to generate the final mask for "aggregates of PanCK+ cells" at the whole slide level.

Additionally, a peritumor inner ROI was automatically generated as an area 0.5 mm into the tumor from the invasive front, and a peritumor outer ROI was automatically generated as the area 0.5 mm outside the tumor from the invasive front.

I.C. Feature Computation and Data Analysis

The following features were computed for each ROI: Area density of all phenotypes; Fraction of panCK$^+$ cells that are PD-L1$^+$; Fraction of CD3$^+$ cells that are PD-L1$^+$; Fraction of CD8$^+$ cells that are PD-L1$^+$; Fraction of CD3$^+$CD8$^-$ cells that are also PD-L1$^+$; Descriptive statistics of distances of CD8+ cells to their nearest PD-L1$^+$/CD68$^+$ neighbor, Descriptive statistics of distances of CD8+ cells to their nearest PD-L1$^+$/panCK$^+$ neighbor, Descriptive statistics of distances of CD8+ cells to their nearest PD-L1$^+$/CD3$^+$ neighbor, Descriptive statistics of distances of panCK$^+$ cells to their nearest CD8$^+$ neighbor, and Average #PD-L1$^+$/panCK$^+$ cells within 10, 30 μm of CD8$^+$ cells. A complete list of computed features is at Table 9:

TABLE 9

| Name | ROI (how computed) | Explanation |
| --- | --- | --- |
| T.CD8-PDL1+CD68 Dist | Tumor region (pathologist) | CD8 to PDL1+CD68 Distance, in μm |
| T.CD8-PDL1+CD3All Dist | Tumor region (pathologist) | CD8 to PDL1+CD3All (CD3+, CD8+) Distance, in μm |
| T.PanCK-CD8 Dist | Tumor region (pathologist) | PanCK to CD8 Distance, in μm |
| T.No.PDL1+PanCK in10 μm CD8 | Tumor region (pathologist) | Number of PDL1+PanCK within 10 μm of CD8 |
| T.No.PDL1+PanCK in30 μm CD8 | Tumor region (pathologist) | Number of PDL1+PanCK within 30 μm of CD8 |
| T.No.CD8 in10 μm PanCK | Tumor region (pathologist) | Number of CD8 within 10 μm of PanCK |
| T.No.CD8 in30 μm PanCK | Tumor region (pathologist) | Number of CD8 within 30 μm of PanCK |
| Epith.CD8toPDL1+CD68 Dist | panCK stained TCs in tumor region | CD8 to PDL1+CD68 Distance, in μm |
| Epith.CD8toPDL1+CD3All Dist | panCK stained TCs in tumor region | CD8 to PDL1+CD3All (CD3+, CD8+) Distance, in μm |
| Epith.PanCKtoCD8 Dist | panCK stained TCs in tumor region | PanCK to CD8 Distance, in μm |
| Epith.No. PDL1+PanCK in10 μm CD8 | panCK stained TCs in tumor region | Number of PDL1+PanCK in within 10 μm of CD8 |
| Epith.No.PDL1+PanCK in30 μm CD8 | panCK stained TCs in tumor region | Number of PDL1+PanCK within 30 μm of CD8 |
| Epith.No.CD8 in 10 μm PanCK | panCK stained TCs in tumor region | Number of CD8 within 10 μm of PanCK |
| Epith.No.CD8 in30 μm PanCK | panCK stained TCs in tumor region | Number of CD8 within 30 μm of PanCK |
| Str.CD8toPDL1+CD68 Dist | Non-panCK stained area in tumor region | CD8 to PDL1+CD68 Distance, in μm |
| Str.CD8toPDL1+CD3All Dist | Non-panCK stained area in tumor region | CD8 to PDL1+CD3All (CD3+, CD8+) Distance, in μm |
| Str.PanCKtoCD8 Dist | Non-panCK stained area in tumor region | PanCK to CD8 Distance, in μm |
| Str.No.PDL1+PanCK in10 μm CD8 | Non-panCK stained area in tumor region | Number of PDL1+PanCK in within 10 μm of CD8 |
| Str.No.PDL1+PanCK in30 μm CD8 | Non-panCK stained area in tumor region | Number of PDL1+PanCK within 30 μm of CD8 |
| Str.No.CD8 in10 μm PanCK | Non-panCK stained area in tumor region | Number of CD8 within 10 μm of PanCK |
| Str.No.CD8 in30 μm PanCK | Non-panCK stained area in tumor region | Number of CD8 within 30 μm of PanCK |
| PTin.CD8toPDL1+CD68 Dist | 0.5 mm inside tumor annotation (system) | CD8 to PDL1+CD68 Distance, in μm |
| PTin.CD8toPDL1+CD3All Dist | 0.5 mm inside tumor annotation (system) | CD8 to PDL1+CD3All (CD3+, CD8+) Distance, in μm |
| PTin.PanCKtoCD8 Dist | 0.5 mm inside tumor annotation (system) | PanCK to CD8 Distance, in μm |
| PTin.No.PDL1+PanCK in10 μm CD8 | 0.5 mm inside tumor annotation (system) | Number of PDL1+PanCK in within 10 μm of CD8 |
| PTin.No.PDL1+PanCK in30 μm CD8 | 0.5 mm inside tumor annotation (system) | Number of PDL1+PanCK within 30 μm of CD8 |
| PTin.No.CD8 in10 μm PanCK | 0.5 mm inside tumor annotation (system) | Number of CD8 within 10 μm of PanCK |
| PTin.No.CD8 in30 μm PanCK | 0.5 mm inside tumor annotation (system) | Number of CD8 within 30 μm of PanCK |
| PTout.CD8toPDL1+CD68 Dist | 0.5 mm outside tumor annotation (system) | CD8 to PDL1+CD68 Distance, in μm |
| PTout.CD8toPDL1+CD3All Dist | 0.5 mm outside tumor annotation (system) | CD8 to PDL1+CD3All (CD3+, CD8+) Distance, in μm |
| PTout.PanCKtoCD8 Dist | 0.5 mm outside tumor annotation (system) | PanCK to CD8 Distance, in μm |

TABLE 9-continued

| Name | ROI (how computed) | Explanation |
| --- | --- | --- |
| PTout.No.PDL1+PanCK in10 μm CD8 | 0.5 mm outside tumor annotation (system) | Number of PDL1+PanCK in within 10 μm of CD8 |
| PTout.No.PDL1+PanCK in30 μm CD8 | 0.5 mm outside tumor annotation (system) | Number of PDL1+PanCK within 30 μm of CD8 |
| PTout.No.CD8 in10 μm PanCK | 0.5 mm outside tumor annotation (system) | Number of CD8 within 10 μm of PanCK |
| PTout.No.CD8 in30 μm PanCK | 0.5 mm outside tumor annotation (system) | Number of CD8 within 30 μm of PanCK |
| PDL1+CD3All density in T | Tumor region (pathologist) | PDL1+CD3All (CD3, CD8) density (in mm$^2$) |
| PDL1+CD3+CD8− density in T | Tumor region (pathologist) | PDL1+CD3All (CD3, CD8) density (in mm2) |
| PDL1+CD8+ density in T | Tumor region (pathologist) | PDL1+CD8+ density (in mm2) |
| PDL1+CD68+ density in T | Tumor region (pathologist) | PDL1+CD68+ density (in mm2) |
| PDL1+PanCK+ density in T | Tumor region (pathologist) | PDL1+PanCK+ density (in mm2) |
| CD3All density in T | Tumor region (pathologist) | CD3All density (in mm2) |
| CD8+ density in T | Tumor region (pathologist) | CD8+ density (in mm2) |
| CD68+ density in T | Tumor region (pathologist) | CD68+ density (in mm2) |
| PanCK+ density in T | Tumor region (pathologist) | PanCK+ density (in mm2) |
| PDL1+CD3All density in Epith | panCK stained TCs in tumor region | PDL1+CD3All (CD3, CD8) density (in mm2) |
| PDL1+CD3+CD8− density in Epith | panCK stained TCs in tumor region | PDL1+CD3All (CD3, CD8) density (in mm2) |
| PDL1+CD8+ density in Epith | panCK stained TCs in tumor region | PDL1+CD8+ density (in mm2) |
| PDL1+CD68+ density in Epith | panCK stained TCs in tumor region | PDL1+CD68+ density (in mm2) |
| PDL1+PanCK+ density in Epith | panCK stained TCs in tumor region | PDL1+PanCK+ density (in mm2) |
| CD3All density in Epith | panCK stained TCs in tumor region | CD3All density (in mm2) |
| CD8+ density in Epith | panCK stained TCs in tumor region | CD8+ density (in mm2) |
| CD68+ density in Epith | panCK stained TCs in tumor region | CD68+ density (in mm2) |
| PanCK+ density in Epith | panCK stained TCs in tumor region | PanCK+ density (in mm2) |
| PDL1+CD3All density in Str | Non-panCK stained area in tumor region | PDL1+CD3All (CD3, CD8) density (in mm2) |
| PDL1+CD3+CD8− density in Str | Non-panCK stained area in tumor region | PDL1+CD3All (CD3, CD8) density (in mm2) |
| PDL1+CD8+ density in Str | Non-panCK stained area in tumor region | PDL1+CD8+ density (in mm2) |
| PDL1+CD68+ density in Str | Non-panCK stained area in tumor region | PDL1+CD68+ density (in mm2) |
| PDL1+PanCK+ density in Str | Non-panCK stained area in tumor region | PDL1+PanCK+ density (in mm2) |
| CD3All density in Str | Non-panCK stained area in tumor region | CD3All density (in mm2) |
| CD8+ density in Str | Non-panCK stained area in tumor region | CD8+ density (in mm2) |
| CD68+ density in Str | Non-panCK stained area in tumor region | CD68+ density (in mm2) |
| PanCK+ density in Str | Non-panCK stained area in tumor region | PanCK+ density (in mm2) |
| PDL1+CD3All density in Ptin | 0.5 mm inside tumor annotation (system) | PDL1+CD3All (CD3, CD8) density (in mm2) |
| PDL1+CD3+CD8− density in Ptin | 0.5 mm inside tumor annotation (system) | PDL1+CD3All (CD3, CD8) density (in mm2) |
| PDL1+CD8+ density in Ptin | 0.5 mm inside tumor annotation (system) | PDL1+CD8+ density (in mm2) |
| PDL1+CD68+ density in Ptin | 0.5 mm inside tumor annotation (system) | PDL1+CD68+ density (in mm2) |
| PDL1+PanCK+ density in Ptin | 0.5 mm inside tumor annotation (system) | PDL1+PanCK+ density (in mm2) |
| CD3All density in Ptin | 0.5 mm inside tumor annotation (system) | CD3All density (in mm2) |
| CD8+ density in Ptin | 0.5 mm inside tumor annotation (system) | CD8+ density (in mm2) |
| CD68+ density in Ptin | 0.5 mm inside tumor annotation (system) | CD68+ density (in mm2) |

TABLE 9-continued

| Name | ROI (how computed) | Explanation |
|---|---|---|
| PanCK+ density in Ptin | 0.5 mm inside tumor annotation (system) | PanCK+ density (in mm2) |
| PDL1+CD3All density in Ptout | 0.5 mm outside tumor annotation (system) | PDL1+CD3All (CD3, CD8) density (in mm2) |
| PDL1+CD3+CD8− density in Ptout | 0.5 mm outside tumor annotation (system) | PDL1+CD3All (CD3, CD8) density (in mm2) |
| PDL1+CD8+ density in Ptout | 0.5 mm outside tumor annotation (system) | PDL1+CD8+ density (in mm2) |
| PDL1+CD68+ density in Ptout | 0.5 mm outside tumor annotation (system) | PDL1+CD68+ density (in mm2) |
| PDL1+PanCK+ density in Ptout | 0.5 mm outside tumor annotation (system) | PDL1+PanCK+ density (in mm2) |
| CD3All density in Ptout | 0.5 mm outside tumor annotation (system) | CD3All density (in mm2) |
| CD8+ density in Ptout | 0.5 mm outside tumor annotation (system) | CD8+ density (in mm2) |
| CD68+ density in Ptout | 0.5 mm outside tumor annotation (system) | CD68+ density (in mm2) |
| PanCK+ density in Ptout | 0.5 mm outside tumor annotation (system) | PanCK+ density (in mm2) |
| PDL1+PanCK+ area ratio in T | Tumor region (pathologist) | PDL1+PanCK+ area versus tumor region (ratio) |
| PanCK+ area ratio in T | Tumor region (pathologist) | PanCK+ area versus tumor region (ratio) |
| PDL1+PanCK+ area ratio in Epith | panCK stained TCs in tumor region | PDL1+PanCK+ area versus panCK stained area (ratio) |
| PanCK+ area ratio in Epith | panCK stained TCs in tumor region | PanCK+ area versus panCK stained area (ratio? No meaning) |
| PDL1+PanCK+ area ratio in Str | Non-panCK stained area in tumor region | PDL1+PanCK+ area versus non-panCK stained area (ratio) |
| PanCK+ area ratio in Str | Non-panCK stained area in tumor region | panCK+ areaversus non-panCK stained area (ratio, no clinical relevant |
| PDL1+PanCK+ area ratio in Ptin | 0.5 mm inside tumor annotation (system) | PDL1+PanCK+ area versus 0.5 mm inside peritumor region (ratio) |
| PanCK+ area ratio in Ptin | 0.5 mm inside tumor annotation (system) | PanCK+ area versus 0.5 mm inside peritumor region (ratio) |
| PDL1+PanCK+ area ratio in Ptout | 0.5 mm outside tumor annotation (system) | PDL1+PanCK+ area versus 0.5 mm outside peritumor region (ratio) |
| PanCK+ area ratio in Ptout | 0.5 mm outside tumor annotation (system) | PanCK+ area versus 0.5 mm outside peritumor region (ratio) |
| PDL1+PanCK/PanCK in T | Tumor region (pathologist) | PDL1+PanCK+ cells versus PanCK+ cells |
| PDL1+PanCK/PanCK in Epith | panCK stained TCs in tumor region | PDL1+PanCK+ cells versus PanCK+ cells |
| PDL1+PanCK/PanCK in Str | Non-panCK stained area in tumor region | PDL1+PanCK+ cells versus PanCK+ cells |
| PDL1+PanCK/PanCK in Ptin | 0.5 mm inside tumor annotation (system) | PDL1+PanCK+ cells versus PanCK+ cells |
| PDL1+PanCK/PanCK in Ptout | 0.5 mm outside tumor annotation (system) | PDL1+PanCK+ cells versus PanCK+ cells |
| PDL1+CD3All/CD3All in T | Tumor region (pathologist) | PDL1+CD3All(CD3+, CD8+) cells versus CD3All (CD3, CD8+) cells |
| PDL1+CD3All/CD3All in Epith | panCK stained TCs in tumor region | PDL1+CD3All(CD3+, CD8+) cells versus CD3All (CD3, CD8+) cells |
| PDL1+CD3All/CD3All in Str | Non-panCK stained area in tumor region | PDL1+CD3All(CD3+, CD8+) cells versus CD3All (CD3, CD8+) cells |
| PDL1+CD3All/CD3All in Ptin | 0.5 mm inside tumor annotation (system) | PDL1+CD3All(CD3+, CD8+) cells versus CD3All (CD3, CD8+) cells |
| PDL1+CD3All/CD3All in Ptout | 0.5 mm outside tumor annotation (system) | PDL1+CD3All(CD3+, CD8+) cells versus CD3All (CD3, CD8+) cells |
| PDL1+CD3+CD8−/ CD3+CD8− in T | Tumor region (pathologist) | PDL1+CD3+CD8− cells versus CD3+, CD8− (CD4) cells |
| PDL1+CD3+CD8−/ CD3+CD8− in Epith | panCK stained TCs in tumor region | PDL1+CD3+CD8− cells versus CD3+, CD8− (CD4) cells |
| PDL1+CD3+CD8−/ CD3+CD8− in Str | Non-panCK stained area in tumor region | PDL1+CD3+CD8− cells versus CD3+, CD8− (CD4) cells |
| PDL1+CD3+CD8−/ CD3+CD8− in Ptin | 0.5 mm inside tumor annotation (system) | PDL1+CD3+CD8− cells versus CD3+, CD8− (CD4) cells |
| PDL1+CD3+CD8−/ CD3+CD8− in Ptout | 0.5 mm outside tumor annotation (system) | PDL1+CD3+CD8− cells versus CD3+, CD8− (CD4) cells |
| PDL1+CD8+/CD8+ in T | Tumor region (pathologist) | PDL1+CD8+ cells versus CD8+ cells |

TABLE 9-continued

| Name | ROI (how computed) | Explanation |
| --- | --- | --- |
| PDL1+CD8+/CD8+ in Epith | panCK stained TCs in tumor region | PDL1+CD8+ cells versus CD8+ cells |
| PDL1+CD8+/CD8+ in Str | Non-panCK stained area in tumor region | PDL1+CD8+ cells versus CD8+ cells |
| PDL1+CD8+/CD8+ in Ptin | 0.5 mm inside tumor annotation (system) | PDL1+CD8+ cells versus CD8+ cells |
| PDL1+CD8+/CD8+ in Ptout | 0.5 mm outside tumor annotation (system) | PDL1+CD8+ cells versus CD8+ cells |
| PDL1+CD68+/CD68+ in T | Tumor region (pathologist) | PDL1+CD68+ cells versus CD68+ cells |
| PDL1+CD68+/CD68+ in Epith | panCK stained TCs in tumor region | PDL1+CD68+ cells versus CD68+ cells |
| PDL1+CD68+/CD68+ in Str | Non-panCK stained area in tumor region | PDL1+CD68+ cells versus CD68+ cells |
| PDL1+CD68+/CD68+ in Ptin | 0.5 mm inside tumor annotation (system) | PDL1+CD68+ cells versus CD68+ cells |
| PDL1+CD68+/CD68+ in Ptout | 0.5 mm outside tumor annotation (system) | PDL1+CD68+ cells versus CD68+ cells |
| CD3+CD8−/CD3All in T | Tumor region (pathologist) | CD3+CD8− cells versus CD3All (CD3+, CD8+) cells |
| CD3+CD8−/CD3All in Epith | panCK stained TCs in tumor region | CD3+CD8− cells versus CD3All (CD3+, CD8+) cells |
| CD3+CD8−/CD3All in Str | Non-panCK stained area in tumor region | CD3+CD8− cells versus CD3All (CD3+, CD8+) cells |
| CD3+CD8−/CD3All in PTin | 0.5 mm inside tumor annotation (system) | CD3+CD8− cells versus CD3All (CD3+, CD8+) cells |
| CD3+CD8−/CD3All in PTout | 0.5 mm outside tumor annotation (system) | CD3+CD8− cells versus CD3All (CD3+, CD8+) cells |

ReliefF feature selection was performed on the features to determine the importance of each feature in classifying the cases according to anti-PD-1 treatment outcome, followed by the selection of the 10 most important features and fitting a quadrant discriminant classifier model to them to predict response to treatment. Treatment outcomes were grouped together in 3 configurations (PD=progressive disease; SD=stable disease; PR=partial response; CR=complete response): PD vs. SD vs. PR+CR; PD vs. SD+PR+CR; PD+SD vs. PR+CR. The majority of the 54 specimens did not have a clear invasive front of tumor, so the feature was excluded from analysis on the peritumor inner and outer regions. Analysis for each configuration was done using 1) all features, 2) tumor only features, and 3) epithelial and stromal features only. This was done with the aim of removing features that were highly correlated to explore the impact on the final classification. Due to the small sample size, no cross-validation was performed and the classification results reported represent the classification accuracy on the training set.

Table 10 summarizes classification accuracy from different configurations and different feature sets.

TABLE 10

| Responses | Features | Mpx Data | Mpx Data + MMR status | MMR Status only |
| --- | --- | --- | --- | --- |
| PD vs. SD vs. PR + CR | All features | 0.80 | 0.85 | N/A |
| | Tumor only features | 0.78 | 0.74 | |
| | Epithelial and stromal features | 0.76 | 0.83 | |
| PD vs. SD + PR + CR | All features | 0.76 | 0.87 | 0.83 |
| | Tumor only features | 0.78 | 0.78 | |
| | Epithelial and stromal features | 0.81 | 0.85 | |
| PD + SD vs. PR + CR | All features | 0.85 | 0.87 | 0.70 |
| | Tumor only features | 0.80 | 0.81 | |
| | Epithelial and stromal features | 0.89 | 0.89 | |

Figure 7:
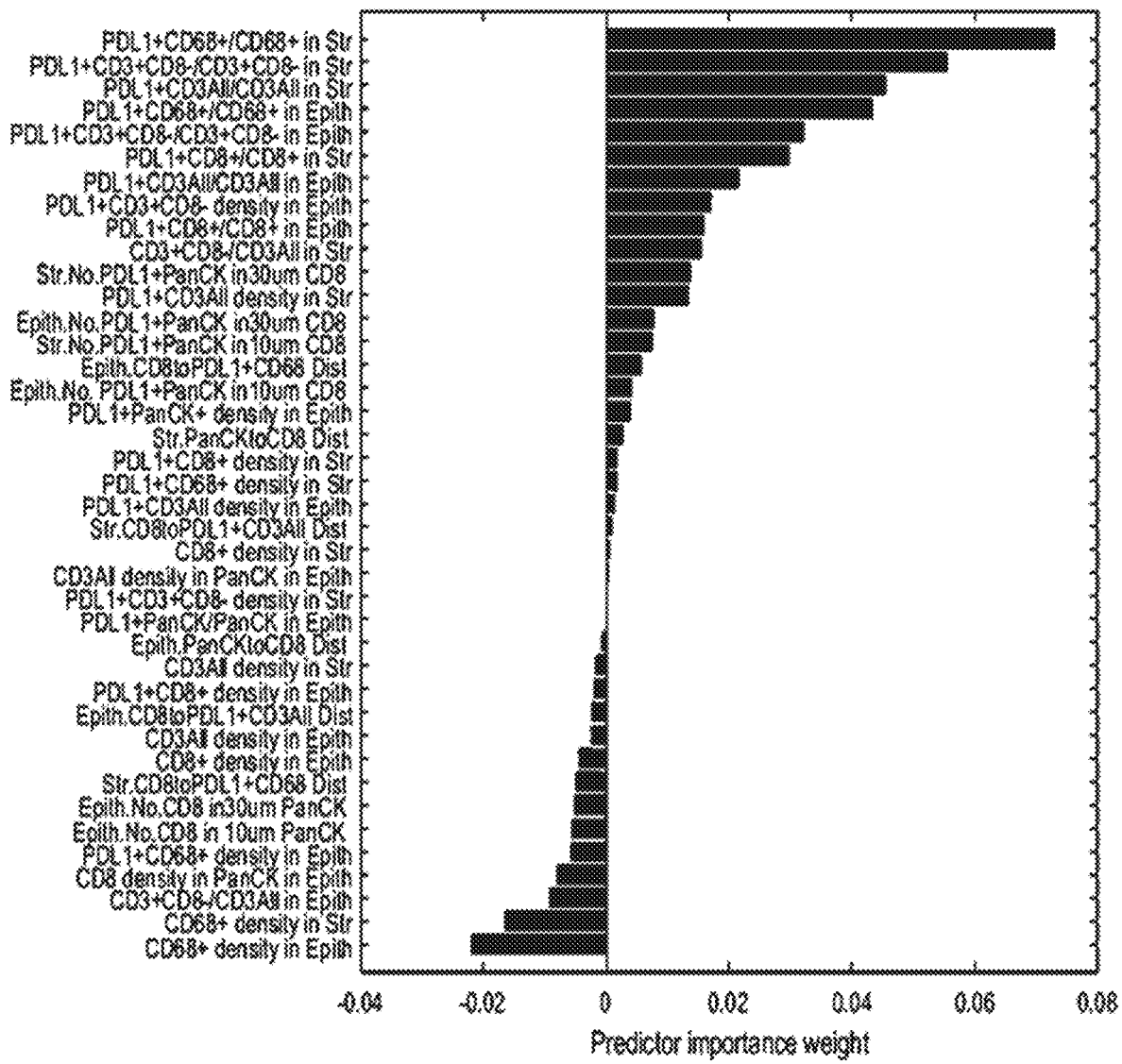
FIG. 7 illustrates the importance ranking of all features in all cases stained with panel 1.

Shaded cells show that for the 3rd configuration (binary response), multiplexed (Mpx) IHC data achieves an accuracy of 89% while the mismatch repair (MMR) status alone achieves 70%. FIG. 7 illustrates the importance ranking of all features in all cases. The following features were identified as most important:

(1) Fraction of PD-L1+ macrophages in stroma, (2) Fraction of PD-L1+ T helper cells in stroma, and (3) Fraction of PD-L1+ T cells in stroma.

Figure 8:
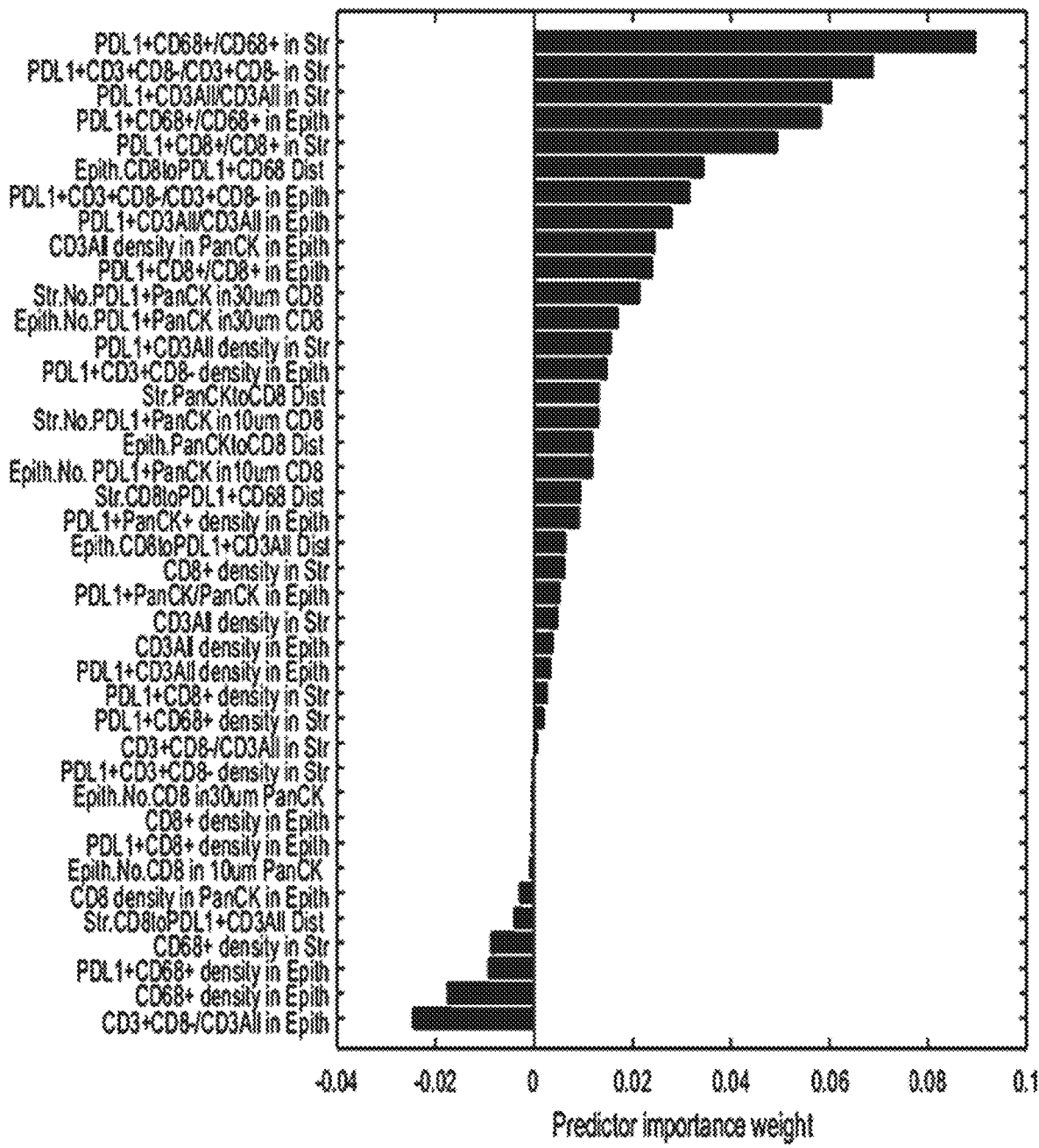
FIG. 8 illustrates the importance ranking of the features in cases MMR deficient cases stained with panel 1.
Figure 10:
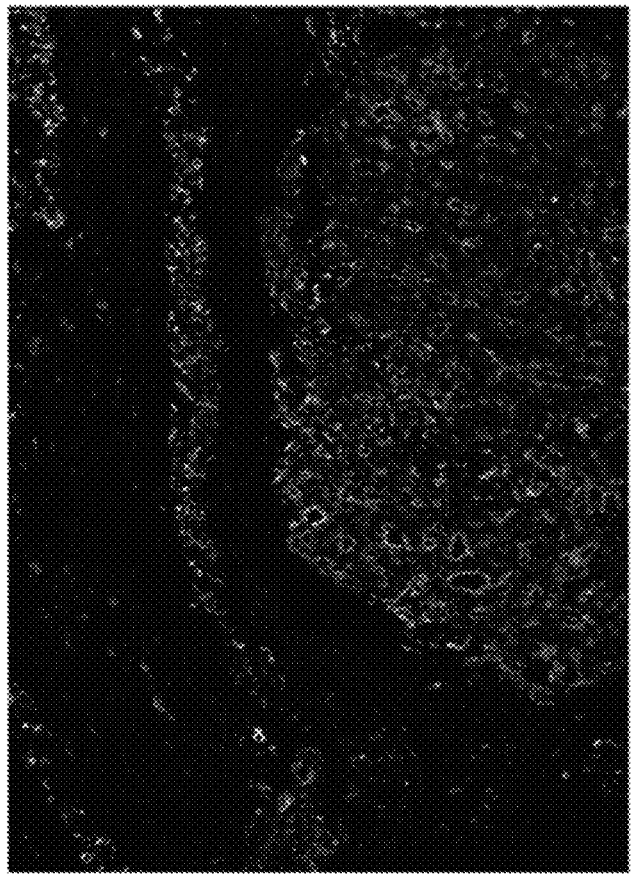
FIG. 10 is an IHC image of a sample stained with panel 1 from a patient who had progressive disease after treatment with a PD-1 axis directed therapy treatment.
Figure 9:
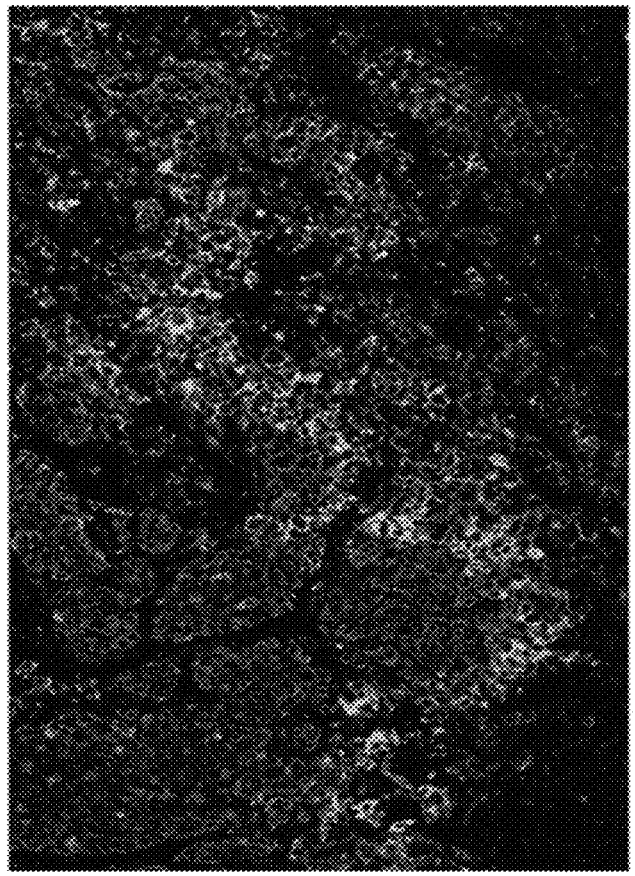
FIG. 9 is an IHC image of a sample stained with panel 1 from a patient that showed a complete response to the PD-1 axis directed therapy treatment.

Mismatch repair (MMR) deficiency has been shown in the past to predict response to anti-PD-1 treatment. An analysis was conducted that focused on only mismatch repair deficient cases, with the aim of identifying whether Multiplex (Mpx) IHC data could identify which MMR deficient cases respond to anti-PD-1 treatment. FIG. 8 shows the importance ranking of the features in the said analysis configuration in MMR deficiency cases. FIG. 9 is an image of a stained sample for a patient that showed a complete response to the treatment, while FIG. 10 is an image of a patient who had progressive disease after treatment. Table 11 shows that using epithelial and stromal Mpx IHC data can achieve a classification accuracy of 92% in separating PD+SD outcomes from PR+CR.

TABLE 11

| Responses | Features | MPX Data Prediction Accuracy |
| --- | --- | --- |
| PD + SD vs. PR + CR | All features | 0.78 |
| | Tumor only features | 0.81 |
| | Epithelial and Stromal features | 0.92 |

Table 12 shows the confusion matrix of the said classification. Among 37 deficient cases, 34 are correctly identified by Mpx IHC data for responders and non-responders, only 3 cases are misclassified. In contrast, 53.7% of MMR deficiency cases are responsive to anti-PD-1 treatment.

TABLE 12

| Responses | Predicted SD + PD by Mpx | Predicted PR + CR by Mpx |
|---|---|---|
| Actual SD + PD (15) | 13 | 2 |
| Actual PR + CR (22) | 1 | 21 |

II. Exploration of Spatial Interaction of PD-1/PD-L1 to Predict Response to Immunotherapy in GI Tracts Tumors by Quantitative Image Analysis of Automated Multiplexed IHC

II.A. Background

Blockade of the PD-1/L1 axis is an effective immunotherapy in some cancer patients. However, identification of predictive biomarkers for patient selection represents a major challenge. Current clinical practice based on PD-L1 expression level by IHC and the emerging biomarker-tumor mutational load and mismatch repair (MMR) status is inadequate. The predictive values are limited for the variable strength of association among studies and tumor types. Recent studies suggest spatial arrangement and interaction between cancer cells and immune cells influence patients' prognosis, survival, and response to treatment. Multiplex Immunohistochemistry (IHC) tissue staining could provide detailed profiles of tumor micro-environments based on specific tumor and immune molecular signatures.

II.B. Samples, Staining, and Image Acquisition

A cohort of 50 pre-treatment (anti-PD-1 pembrolizumab) patient gastrointestinal tract tumor specimens with acceptable image and tissue quality for automated analysis was available to this study. Table 13 shows the breakdown of responses.

TABLE 13

| Anti-PD-1 responses | # of patients (all pre-treatment specimens) |
|---|---|
| PD (progressive diseases) | 15 |
| SD (stable diseases) | 17 |
| NE (not evaluable) | 3 |
| PR (partial responses) | 11 |
| CR (complete responses) | 4 |
| Total | 50 |

Samples were formalin fixed, paraffin embedded, sectioned, and mounted on microscope slides.

Figure 11:
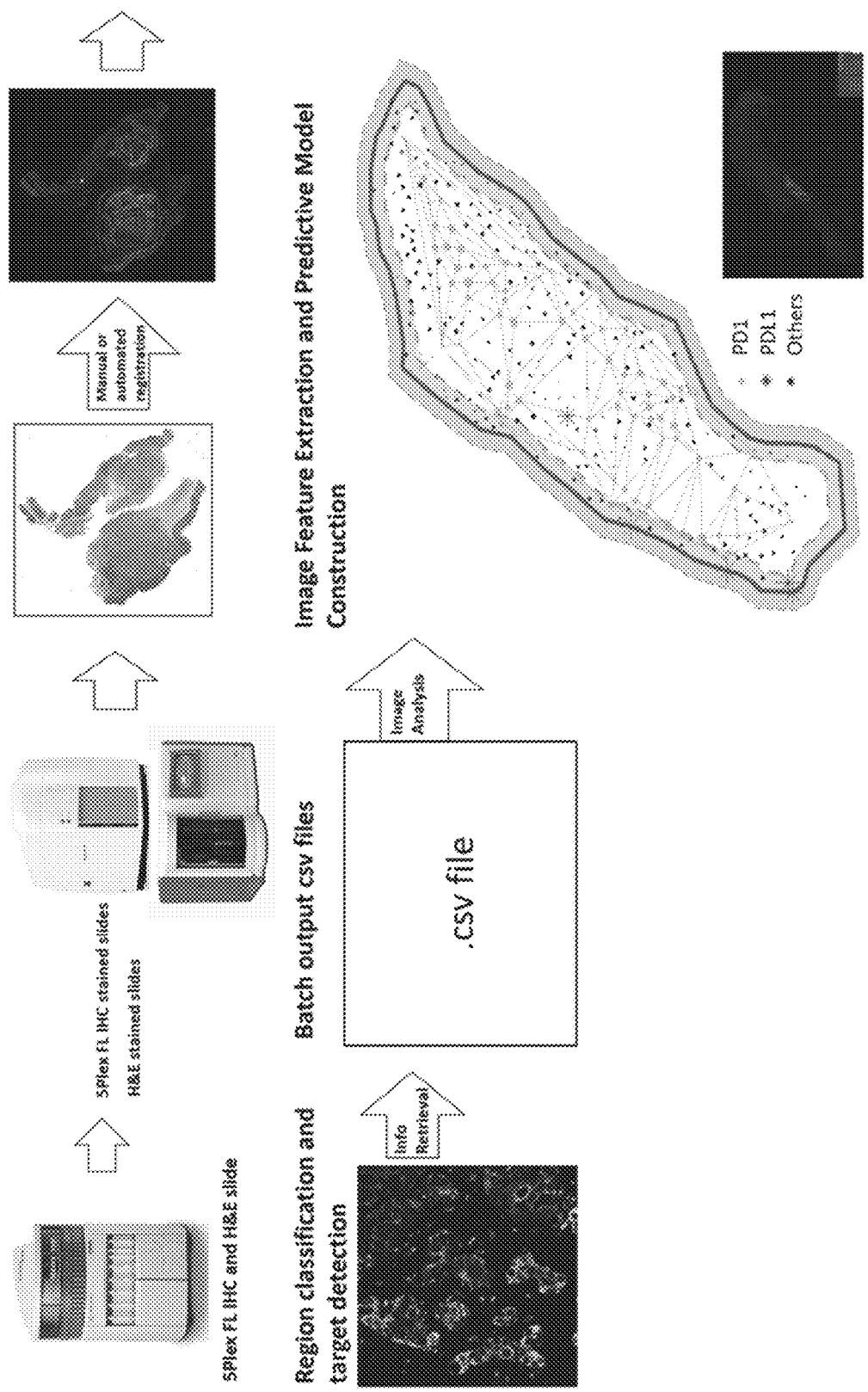
FIG. 11 illustrates the staining and image analysis process used in Example II for panel 2.

An overview of the staining and image analysis is illustrated at FIG. 11. Slides were stained in a multiplex IHC for PanCK, PD-L1, PD1, CD8, LAG3 on a BenchMark ULTRA IHC/ISH automated slide stainer with fluorescent tyramide dye conjugates in a tyramide signal amplification procedure as set forth in Table 14:

TABLE 14

| | Primary antibody | Secondary antibody | Tyramide Conjugate |
|---|---|---|---|
| 1 | CD8 (SP239) rabbit monoclonal [Roche] | Goat-anti-rabbit-HRP | Rhodamine-6-G |
| 2 | LAG3 (EPR4392(2)) rabbit monoclonal [Abcam] | Goat-anti-rabbit-HRP | 7-Diethylaminocoumarin (DEAC) |
| 3 | PanCK (AE1/AE3/PCK26) mouse cocktail [Roche] | Goat-anti-mouse-HRP | Red610 |
| 4 | PD-1 (NAT105) mouse monoclonal [Abcam] | Goat-anti-mouse-HRP | SulfoCy5 |
| 5 | PD-L1 (SP263) rabbit monoclonal [Roche] | Goat-anti-rabbit-HRP | FAM |

Stains were applied sequentially as in Example I. After each stain deposition a heat kill step was applied, comprising a process as described by Zhang (I). A serial section of each sample was also stained for H & E using a VENTANA HE 600 automated slide stainer.

Whole slides were scanned with Zeiss AXIO Z1 scanner, on which pathologists annotated tumor area. Halo Hi-Plex software was used for image analysis. MatLab Computer Vision, Image Processing, and Machine Learning Toolbox were used to: (a) Reconstruct graphs of each cell type from spatial locations in Halo output csv files; (b) Develop quantitative metrics to characterize the interplay between different cell signals; (c) Rank and mine the most predictive feature combinations in relation to anti-PD-1 responses; and (d) Build and optimize the predictive model based on the selected features.

II.C. Image Annotation and ROI Generation

A tumor region ROI and an invasive front of the tumor (if available) were annotated in the images by a pathologist. The DPath system automatically annotated epithelial tumor ROIs from aggregates of panCK+ cells, and stromal regions as described for Example I.

II.C. Feature Computation and Data Analysis

Each of the features in Table 16 were analyzed for each image and ranked by both ReliefF and Random Forest:

TABLE 16

1. 'number of PD1 positive cells in panCK positive area'
2. 'number of PD1 positive cells in panCK negative area'
3. 'number of PD1+ panCK+ cells divided by area of panCK positive cells'
4. 'number of PD1+ panCK− cells divided by area of panCK negative cells'
5. 'number of PDL1 positive cells in panCK positive area'
6. 'number of PDL1 positive cells in panCK negative area'
7. 'number of PDL1+ panCK+ cells divided by area of panCK positive cells'
8. 'number of PDL1+ panCK− cells divided by area of panCK negative cells'
9. 'number of CD8 positive cells in panCK positive area'
10. 'number of CD8 positive cells in panCK negative area'
11. 'number of CD8+ panCK+ cells divided by area of panCK positive cells'
12. 'number of CD8+ panCK− cells divided by area of panCK negative cells'
13. 'number of Lag3 positive cells in panCK positive area'
14. 'number of Lag3 positive cells in panCK negative area'
15. 'number of Lag3+ panCK+ cells divided by area of panCK positive cells'
16. 'number of Lag3+ panCK− cells divided by area of panCK negative cells'
17. 'number of Lag3 positive cells in panCK positive area'
18. 'number of Lag3 positive cells in panCK negative area'

TABLE 16-continued

19. 'number of Lag3+ panCK+ cells divided by area of panCK positive cells'
20. 'number of Lag3+ panCK− cells divided by area of panCK negative cells'
21. 'ratio of number of PD1+&CD8+ to CD8+ cell in panCK positive area'
22. 'ratio of number of PD1+&CD8+ to CD8+ cell in panCK negative area'
23. 'ratio of number of PD1−&CD8+ to CD8+ cell in panCK positive area'
24. 'ratio of number of PD1−&CD8+ to CD8+ cell in panCK negative area'
25. 'ratio of number of Lag3+&CD8+ to CD8+ cell in panCK positive area'
26. 'ratio of number of Lag3+&CD8+ to CD8+ cell in panCK negative area'
27. 'ratio of number of Lag3−&CD8+ to CD8+ cell in panCK positive area'
28. 'ratio of number of Lag3−&CD8+ to CD8+ cell in panCK negative area'
29. 'ratio of number of PDL1+&CD8+ to CD8+ cell in panCK positive area'
30. 'ratio of number of PDL1+&CD8+ to CD8+ cell in panCK negative area'
31. 'ratio of number of PDL1−&CD8+ to CD8+ cell in panCK positive area'
32. 'ratio of number of PDL1−&CD8+ to CD8+ cell in panCK negative area'
33. 'ratio of number of PD1+&Lag3+&CD8+ to CD8+ cell in panCK positive area'
34. 'ratio of number of PD1+&Lag3+&CD8+ to CD8+ cell in panCK negative area'
35. 'ratio of number of PD1+&PDL1+&CD8+ to CD8+ cell in panCK positive area'
36. 'ratio of number of PD1+&PDL1+&CD8+ to CD8+ cell in panCK negative area'
37. 'ratio of number of PD1+&PDL1+&Lag3+&CD8+ to CD8+ cell in panCK positive area'
38. 'ratio of number of PD1+&PDL1+&Lag3+&CD8+ to CD8+ cell in panCK negative area'
39. 'ratio of number of PD1−&PDL1+&Lag3+&CD8+ to CD8+ cell in panCK positive area'
40. 'ratio of number of PD1−&PDL1+&Lag3+&CD8+ to CD8+ cell in panCK negative area'
41. 'ratio of number of PD1+&PDL1−&Lag3+&CD8+ to CD8+ cell in panCK positive area'
42. 'ratio of number of PD1+&PDL1−&Lag3+&CD8+ to CD8+ cell in panCK negative area'
43. 'mean value of all cell PD1 intensity'
44. 'variance of all cell PD1 intensity'
45. 'min value of all cell PD1 intensity'
46. 'max value of all cell PD1 intensity'
47. 'mean value of CD8+ cell PD1 intensity'
48. 'variance of CD8+ cell PD1 intensity'
49. 'min value of CD8+ cell PD1 intensity'
50. 'max value of CD8+ cell PD1 intensity'
51. 'mean value of all cell PDL1 intensity'
52. 'variance of all cell PDL1 intensity'
53. 'min value of all cell PDL1 intensity'
54. 'max value of all cell PDL1 intensity'
55. 'mean value of CD8+ cell PDL1 intensity'
56. 'variance of CD8+ cell PDL1 intensity'
57. 'min value of CD8+ cell PDL1 intensity'
58. 'max value of CD8+ cell PDL1 intensity'
59. 'mean value of panCK+ cell PDL1 intensity'
60. 'variance of panCK+ cell PDL1 intensity'
61. 'min value of panCK+ cell PDL1 intensity'
62. 'max value of panCK+ cell PDL1 intensity'
63. 'mean value of all cell Lag3 intensity'
64. 'variance of all cell Lag3 intensity'
65. 'min value of all cell Lag3 intensity'
66. 'max value of all cell Lag3 intensity'
67. 'mean value of CD8+ cell Lag3 intensity'
68. 'variance of CD8+ cell Lag3 intensity'
69. 'min value of CD8+ cell Lag3 intensity'
70. 'max value of CD8+ cell Lag3 intensity'
71. 'mean number of PD1 within 10 μm radius of PDL1'
72. 'variance of number of PD1 within 10 μm radius of PDL1'
73. 'min number of PD1 within 10 μm radius of PDL1'
74. 'max number of PD1 within 10 μm radius of PDL1'
75. 'mean number of PD1 within 20 μm radius of PDL1'
76. 'variance of number of PD1 within 20 μm radius of PDL1'
77. 'min number of PD1 within 20 μm radius of PDL1'
78. 'max number of PD1 within 20 μm radius of PDL1'
79. 'mean number of PDL1 within 10 μm radius of PD1'
80. 'variance of number of PDL1 within 10 μm radius of PD1'
81. 'min number of PDL1 within 10 μm radius of PD1'
82. 'max number of PDL1 within 10 μm radius of PD1'
83. 'mean number of PDL1 within 20 μm radius of PD1'
84. 'variance of number of PDL1 within 20 μm radius of PD1'
85. 'min number of PDL1 within 20 μm radius of PD1'
86. 'max number of PDL1 within 20 μm radius of PD1'
87. 'mean number of PD1+&CD8+ within 10 μm radius of PDL1'
88. 'variance of number of PD1+&CD8+ within 10 μm radius of PDL1'
89. 'min number of PD1+&CD8+ within 10 μm radius of PDL1'
90. 'max number of PD1+&CD8+ within 10 μm radius of PDL1'
91. 'mean number of PD1+&CD8+ within 20 μm radius of PDL1'
92. 'variance of number of PD1+&CD8+ within 20 μm radius of PDL1'
93. 'min number of PD1+&CD8+ within 20 μm radius of PDL1'
94. 'max number of PD1+&CD8+ within 20 μm radius of PDL1'
95. 'mean number of PD1+&CD8+ within 10 μm radius of PDL1+&panCK+'
96. 'variance of number of PD1+&CD8+ within 10 μm radius of PDL1+&panCK+'
97. 'min number of PD1+&CD8+ within 10 μm radius of PDL1+&panCK+'
98. 'max number of PD1+&CD8+ within 10 μm radius of PDL1+&panCK+'
99. 'mean number of PD1+&CD8+ within 20 μm radius of PDL1+&panCK+'
100. 'variance of number of PD1+&CD8+ within 20 μm radius of PDL1+&panCK+'
101. 'min number of PD1+&CD8+ within 20 μm radius of PDL1+&panCK+'
102. 'max number of PD1+&CD8+ within 20 μm radius of PDL1+&panCK+'
103. 'mean number of PD1+&CD8+ within 10 μm radius of PDL1+&CD8+'
104. 'variance of number of PD1+&CD8+ within 10 μm radius of PDL1+&CD8+'
105. 'min number of PD1+&CD8+ within 10 μm radius of PDL1+&CD8+'
106. 'max number of PD1+&CD8+ within 10 μm radius of PDL1+&CD8+'
107. 'mean number of PD1+&CD8+ within 20 μm radius of PDL1+&CD8+'
108. 'variance of number of PD1+&CD8+ within 20 μm radius of PDL1+&CD8+'
109. 'min number of PD1+&CD8+ within 20 μm radius of PDL1+&CD8+'
110. 'max number of PD1+&CD8+ within 20 μm radius of PDL1+&CD8+'
111. 'mean number of PD1Low&CD8+ within 10 μm radius of PDL1'
112. 'variance of number of PD1Low&CD8+ within 10 μm radius of PDL1'
113. 'min number of PD1Low&CD8+ within 10 μm radius of PDL1'
114. 'max number of PD1Low&CD8+ within 10 μm radius of PDL1'
115. 'mean number of PD1Low&CD8+ within 20 μm radius of PDL1'
116. 'variance of number of PD1Low&CD8+ within 20 μm radius of PDL1'
117. 'min number of PD1Low&CD8+ within 20 μm radius of PDL1'
118. 'max number of PD1Low&CD8+ within 20 μm radius of PDL1'
119. 'mean number of PD1Low&CD8+ within 10 μm radius of PDL1+&panCK+'
120. 'variance of number of PD1Low&CD8+ within 10 μm radius of PDL1+&panCK+'
121. 'min number of PD1Low&CD8+ within 10 μm radius of PDL1+&panCK+'

TABLE 16-continued

122. 'max number of PD1Low&CD8+ within 10 μm radius of PDL1+&panCK+'
123. 'mean number of PD1Low&CD8+ within 20 μm radius of PDL1+&panCK+'
124. 'variance of number of PD1Low&CD8+ within 20 μm radius of PDL1+&panCK+'
125. 'min number of PD1Low&CD8+ within 20 μm radius of PDL1+&panCK+'
126. 'max number of PD1Low&CD8+ within 20 μm radius of PDL1+&panCK+'
127. 'mean number of PD1Low&CD8+ within 10 μm radius of PDL1+&CD8+'
128. 'variance of number of PD1Low&CD8+ within 10 μm radius of PDL1+&CD8+'
129. 'min number of PD1Low&CD8+ within 10 μm radius of PDL1+&CD8+'
130. 'max number of PD1Low&CD8+ within 10 μm radius of PDL1+&CD8+'
131. 'mean number of PD1Low&CD8+ within 20 μm radius of PDL1+&CD8+'
132. 'variance of number of PD1Low&CD8+ within 20 μm radius of PDL1+&CD8+'
133. 'min number of PD1Low&CD8+ within 20 μm radius of PDL1+&CD8+'
134. 'max number of PD1Low&CD8+ within 20 μm radius of PDL1+&CD8+'
135. 'mean number of PD1Med&CD8+ within 10 μm radius of PDL1'
136. 'variance of number of PD1Med&CD8+ within 10 μm radius of PDL1'
137. 'min number of PD1Med&CD8+ within 10 μm radius of PDL1'
138. 'max number of PD1Med&CD8+ within 10 μm radius of PDL1'
139. 'mean number of PD1Med&CD8+ within 20 μm radius of PDL1'
140. 'variance of number of PD1Med&CD8+ within 20 μm radius of PDL1'
141. 'min number of PD1Med&CD8+ within 20 μm radius of PDL1'
142. 'max number of PD1Med&CD8+ within 20 μm radius of PDL1'
143. 'mean number of PD1Med&CD8+ within 10 μm radius of PDL1+&panCK+'
144. 'variance of number of PD1Med&CD8+ within 10 μm radius of PDL1+&panCK+'
145. 'min number of PD1Med&CD8+ within 10 μm radius of PDL1+&panCK+'
146. 'max number of PD1Med&CD8+ within 10 μm radius of PDL1+&panCK+'
147. 'mean number of PD1Med&CD8+ within 20 μm radius of PDL1+&panCK+'
148. 'variance of number of PD1Med&CD8+ within 20 μm radius of PDL1+&panCK+'
149. 'min number of PD1Med&CD8+ within 20 μm radius of PDL1+&panCK+'
150. 'max number of PD1Med&CD8+ within 20 μm radius of PDL1+&panCK+'
151. 'mean number of PD1Med&CD8+ within 10 μm radius of PDL1+&CD8+'
152. 'variance of number of PD1Med&CD8+ within 10 μm radius of PDL1+&CD8+'
153. 'min number of PD1Med&CD8+ within 10 μm radius of PDL1+&CD8+'
154. 'max number of PD1Med&CD8+ within 10 μm radius of PDL1+&CD8+'
155. 'mean number of PD1Med&CD8+ within 20 μm radius of PDL1+&CD8+'
156. 'variance of number of PD1Med&CD8+ within 20 μm radius of PDL1+&CD8+'
157. 'min number of PD1Med&CD8+ within 20 μm radius of PDL1+&CD8+'
158. 'max number of PD1Med&CD8+ within 20 μm radius of PDL1+&CD8+'
159. 'mean number of PD1High&CD8+ within 10 μm radius of PDL1'
160. 'variance of number of PD1High&CD8+ within 10 μm radius of PDL1'
161. 'min number of PD1High&CD8+ within 10 μm radius of PDL1'
162. 'max number of PD1High&CD8+ within 10 μm radius of PDL1'
163. 'mean number of PD1High&CD8+ within 20 μm radius of PDL1'
164. 'variance of number of PD1High&CD8+ within 20 μm radius of PDL1'
165. 'min number of PD1High&CD8+ within 20 μm radius of PDL1'
166. 'max number of PD1High&CD8+ within 20 μm radius of PDL1'
167. 'mean number of PD1High&CD8+ within 10 μm radius of PDL1+&panCK+'
168. 'variance of number of PD1High&CD8+ within 10 μm radius of PDL1+&panCK+'
169. 'min number of PD1High&CD8+ within 10 μm radius of PDL1+&panCK+'
170. 'max number of PD1High&CD8+ within 10 μm radius of PDL1+&panCK+'
171. 'mean number of PD1High&CD8+ within 20 μm radius of PDL1+&panCK+'
172. 'variance of number of PD1High&CD8+ within 20 μm radius of PDL1+&panCK+'
173. 'min number of PD1High&CD8+ within 20 μm radius of PDL1+&panCK+'
174. 'max number of PD1High&CD8+ within 20 μm radius of PDL1+&panCK+'
175. 'mean number of PD1High&CD8+ within 10 μm radius of PDL1+&CD8+'
176. 'variance of number of PD1High&CD8+ within 10 μm radius of PDL1+&CD8+'
177. 'min number of PD1High&CD8+ within 10 μm radius of PDL1+&CD8+'
178. 'max number of PD1High&CD8+ within 10 μm radius of PDL1+&CD8+'
179. 'mean number of PD1High&CD8+ within 20 μm radius of PDL1+&CD8+'
180. 'variance of number of PD1High&CD8+ within 20 μm radius of PDL1+&CD8+'
181. 'min number of PD1High&CD8+ within 20 μm radius of PDL1+&CD8+'
182. 'max number of PD1High&CD8+ within 20 μm radius of PDL1+&CD8+'
183. 'number of co-expressed PD1/PDL1 cells'
184. 'number of co-expressed PD1PosCD8Pos/PDL1 cells'
185. 'average distance from PD1 to its nearest PDL1'
186. 'average distance from PD1Pos&CD8Pos to its nearest PDL1'
187. 'average distance from PDL1 to its nearest PD1'
188. 'std of distance from PD1 to its nearest PDL1'
189. 'std of distance from PD1 to its nearest PDL1'
190. 'std of distance from PDL1 to its nearest PD1'

Figure 12:
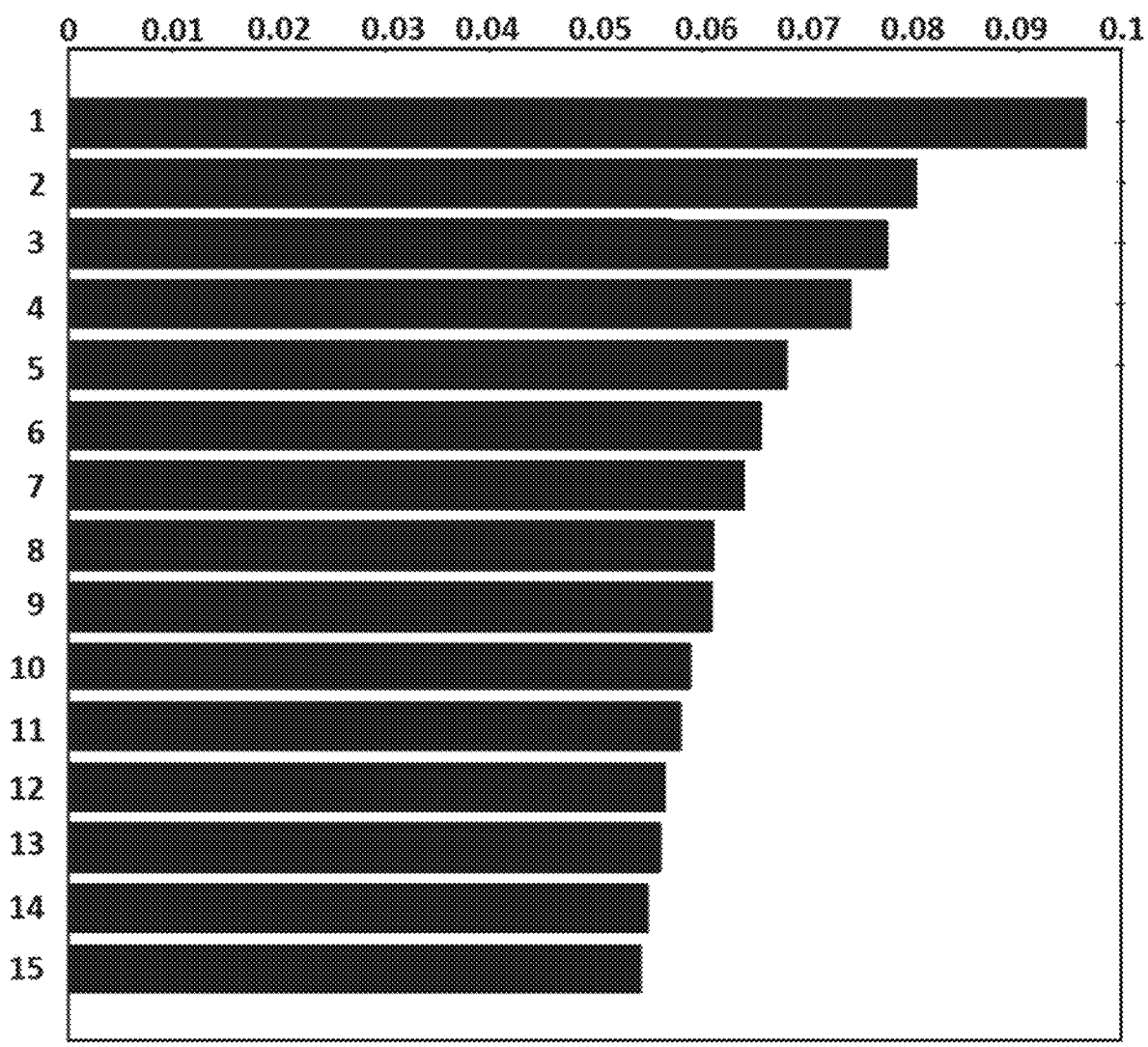
FIG. 12 illustrates the ranking of the top 15 features for panel 2 using ReliefF feature selection function. Features are as follows: (1) Max number of PD-$1_{Low\ Intensity}$/CD8+ cells within 20 μm radius of a PD-L1+/CD8+ cell; (2) max value of PD-L1 intensity from a PD-L1+/CD8+ cell; (3) ratio of the number of PD-1+/PD-L1−/Lag3+/CD8+ cells to CD8+ cells in panCK− area; (4) Spatial variance in the number of PD-$1_{Low\ Intensity}$/CD8+ cells within a 20 μm radius of a PD-L1+ cell; (5) Max value of PD-L1 intensity from all PD-L1+ cells; (6) Number of Lag3+ cells in panCK− area; (7) Density of PD-L1+/panCK− cells in panCK− area; (8) Number of PD-L1+ cells in panCK+ area; (9) Number of PD-L1+ cells in panCK− area; (10) Number of PD-1+ cells in panCK− area; (11) max number of PD-$1_{Low\ Intensity}$/CD8+ cells within a 20 μm radius of a PD-L1+ cell; (12) mean number of PD-$1_{Low\ Intensity}$/CD8+ cells within a 20 μm radius of a PD-L1+ cell; (13) Max value of Lag3 intensity from CD8+/Lag3+ cells; (14) number of CD8+ cells in panCK− area; and (15) Variance in the number of PD-$1_{Low\ Intensity}$/CD8+ cells within a 20 μm radius of a PD-L1+/CD8+ cell.
Figure 13:
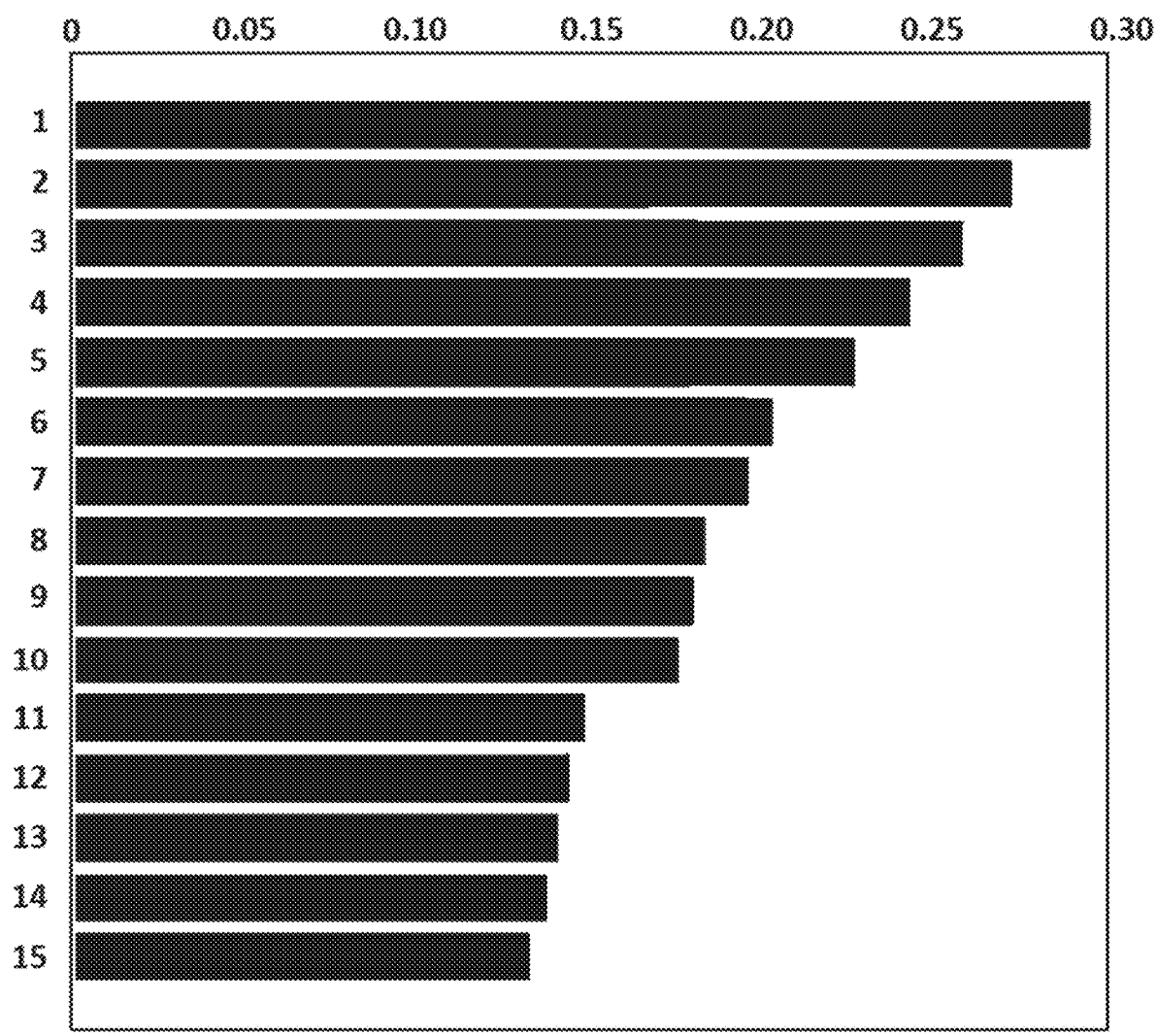
FIG. 13 illustrates the ranking of the top 15 features for panel 2 using Random Forest feature selection function. Features are as follows: (1) Average distance from PD-L1+ cell to its nearest PD-1+ cell; (2) Max number of PD-$1_{Low\ Intensity}$/CD8+ cells within 20 μm radius of a PD-L1+/CD8+ cell; (3) Max number of PD-$1_{Low\ Intensity}$/CD8+ cells within 20 μm radius of a PD-L1+/panCK+ cell; (4) std distance from PD-L1+ cell to the nearest PD-1+ cell; (5) ratio of the number of Lag3+/CD8+ cells to CD8+ cells in panCK− area; (6) ratio of the number of PD-L1+/CD8+ cells to CD8+ cells in panCK− area; (7) mean number of PD-$1_{Low\ Intensity}$/CD8+ cells within 10 μm radius of a PD-L1+ cell; (8) variance in the number of PD-$1_{Low\ Intensity}$/CD8+ cells within 10 μm radius of a PD-L1+ cell; (9) mean value of PD-1 intensity from all PD-1+ cells; (10) minimum value of Lag3 intensity from all Lag3+ cells; (11) density of PD-L1+ cells in panCK− area; (12) maximum number of PD-$1_{Low\ Intensity}$/CD8+ cells within 10 μm radius of a PD-L1+/CD8+ cell; (13) number of PD-1+ cells in the panCK+ area; (14) ratio of the number of PD-1+/PD-L1−/Lag3+/CD8+ cells to CD8+ cells in panCK− area; and (15) max value of Lag3 intensity from Lag3+/CD8+ cells.

Ranking of the top 15 features from each of the ReliefF and Random Forest rank are illustrated at FIG. 12 and FIG. 13, respectively. Of the 190 features analyzed, both Relieff and Random Forest rank the following feature in the top two features in predicting response to treatment: "Maximum number of CD8+/PD-1low-intensity cells within 20 μm of PD-L1+ cells in epithelial tumor". Quadrant Discriminant Analysis (QDA) with 5-fold cross validation yields a prediction accuracy of 85%. When combined with the "average #PD-1+ cells within 20 μm radius of PD-L1+ cells" and the "max value of Lag3+ intensity on CD8+ cell", the accuracy reaches 90.2%, regardless of the MMR status (see FIG. 14 and Tables 17 and 18).

TABLE 17

| Anti-PD-1 responses | MMR Proficient | MMR Deficient |
|---|---|---|
| PD + SD + NE | 17 | 18 |
| PR + CR | 1 | 14 |

TABLE 18

| Predictor | MPX | MMR | MPX + MMR |
|---|---|---|---|
| Accuracy | 90.2% | 62% | 80% |

Other features have lower accuracy (e.g. 60-70%).

Figure 14A:
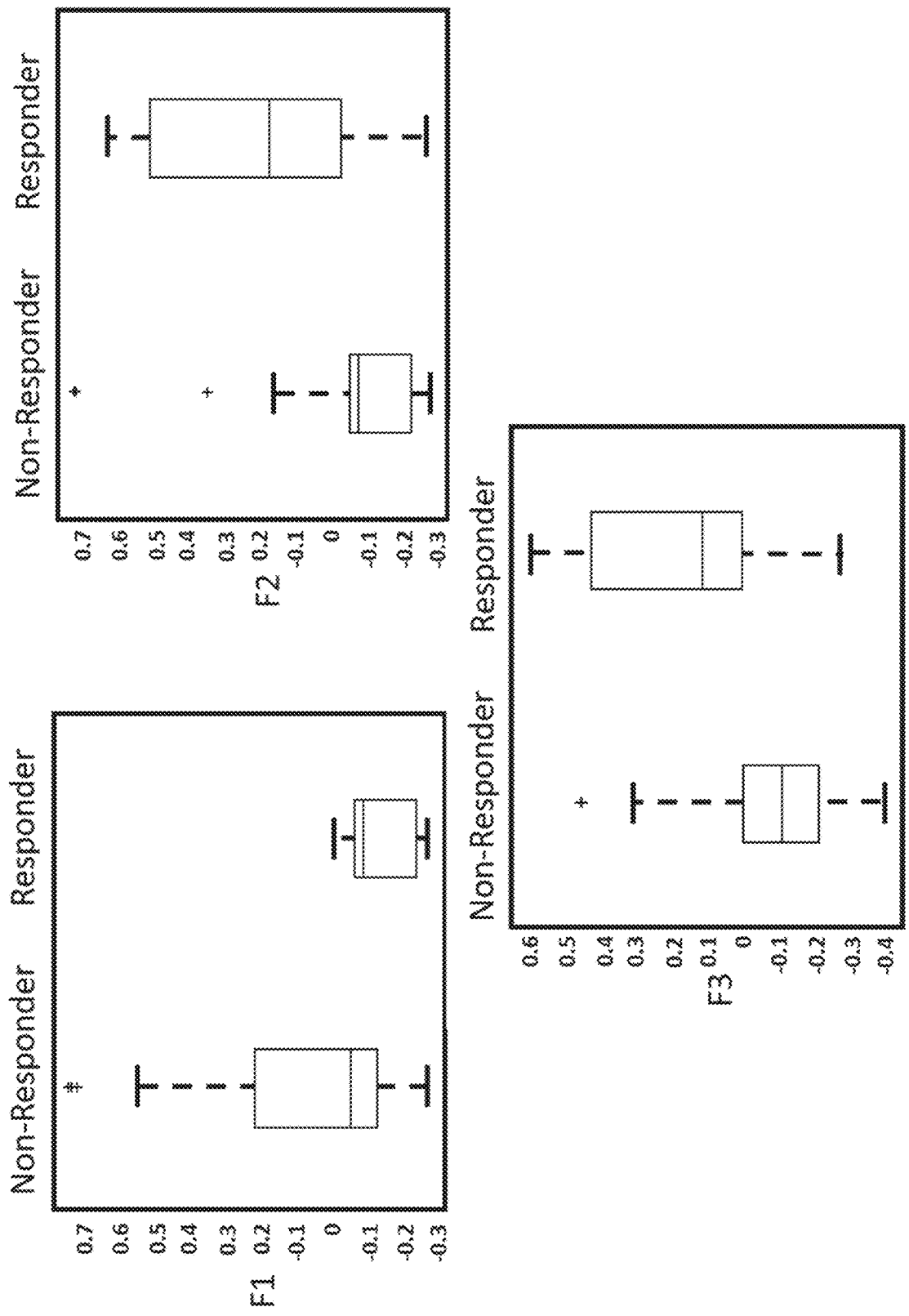
FIG. 14A contains charts illustrating: the predictive value of spatial variance #PD-1+ cells within 10 μm radius of PD-L1+ cells (F1), the predictive value of mean #PD-$1_{Low\ Intensity}$CD8+ cells within 20 μm radius of PD-L1+ cells (F2), and the predictive value of max value of Lag3 intensity in CD8+Lag3+ cells (F3).
Figure 14B:
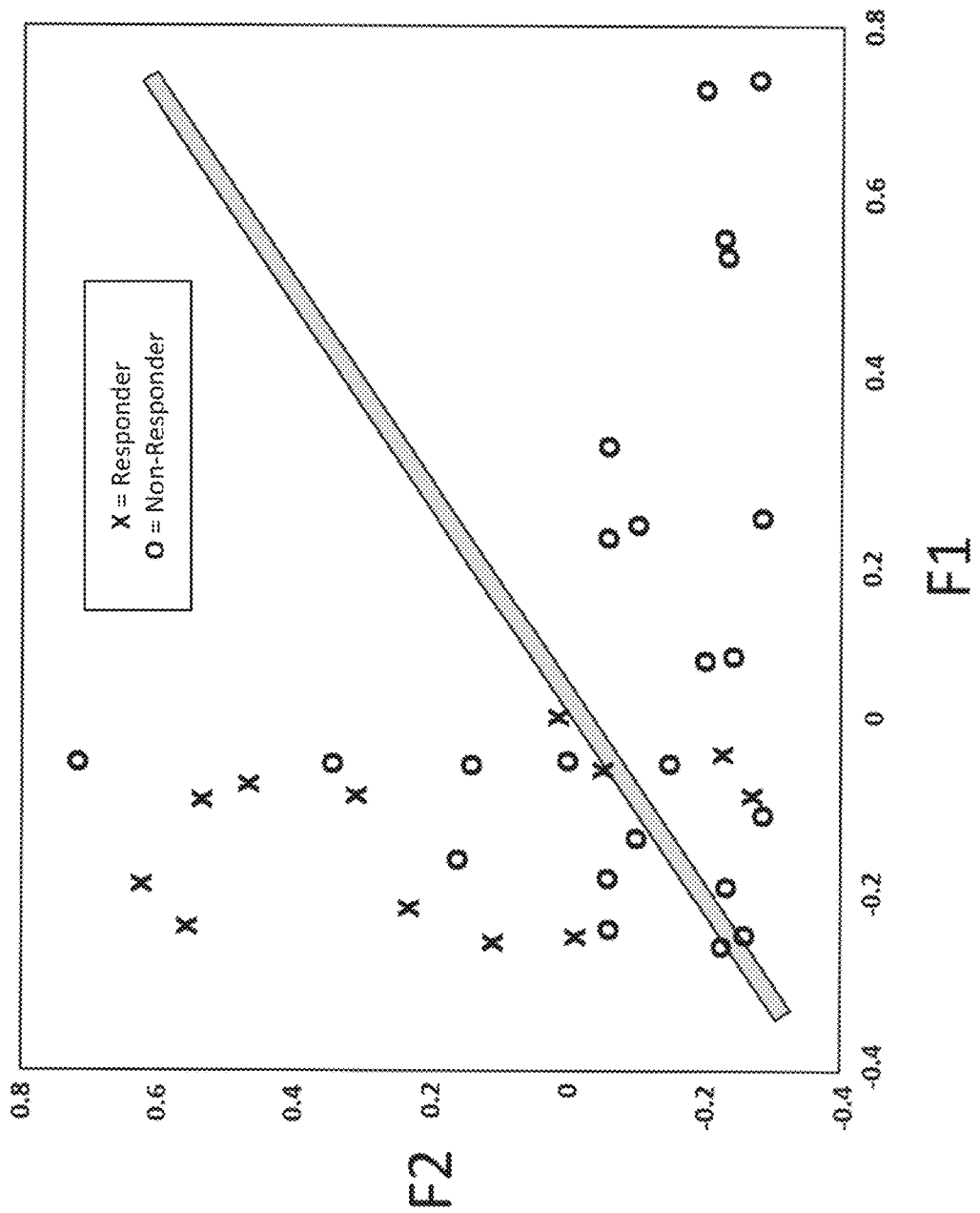
FIG. 14B is a scatter plot showing the predictive value of spatial variance #PD-1+ cells within 10 μm radius of PD-L1+ cells (F1) and the mean #PD-$1_{Low\ Intensity}$CD8+ cells within 20 μm radius of PD-L1+ cells (F2).
Figure 14C:
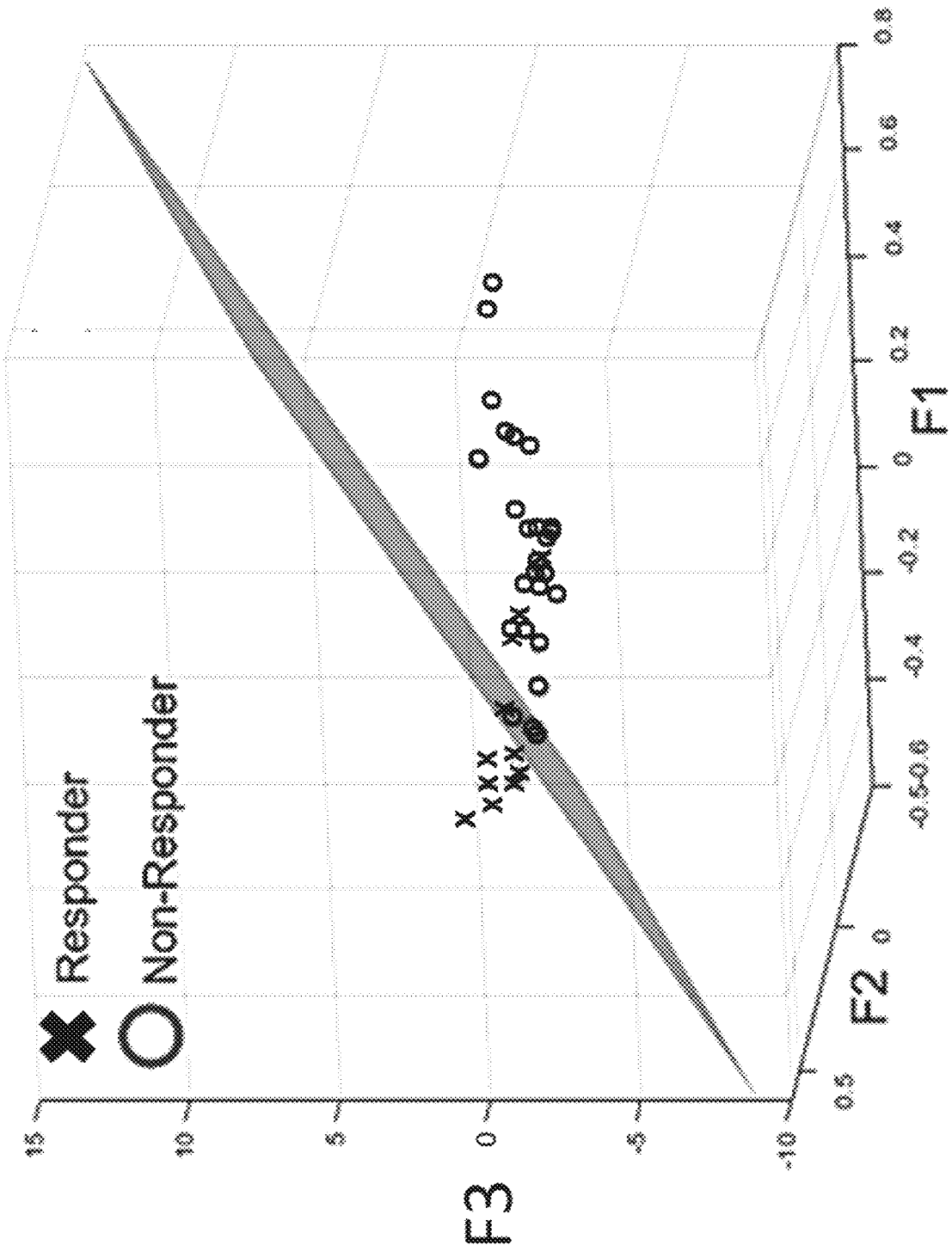
FIG. 14C is a scatter plot showing the predictive value of the spatial variance #PD-1+ cells within 10 μm radius of PD-L1+ cells (F1), the mean #PD-$1_{Low\ Intensity}$CD8+ cells within 20 μm radius of PD-L1+ cells (F2), and the max value of Lag3 intensity in CD8+Lag3+ cells (F3).

FIG. 14A-14C illustrates: (a) the predictive value of spatial variance #PD-1+ cells within 10 µm radius of PD-L1+ cells; (b) the predictive value of mean #PD-1$_{Low\ Intensity}$CD8$^+$ cells within 20 µm radius of PD-L1$^+$ cells; (c) the predictive value of max value of Lag3 intensity in CD8$^+$Lag3$^+$ cells; and (d) a scatter plot showing (a) versus (b).

Figure 15:
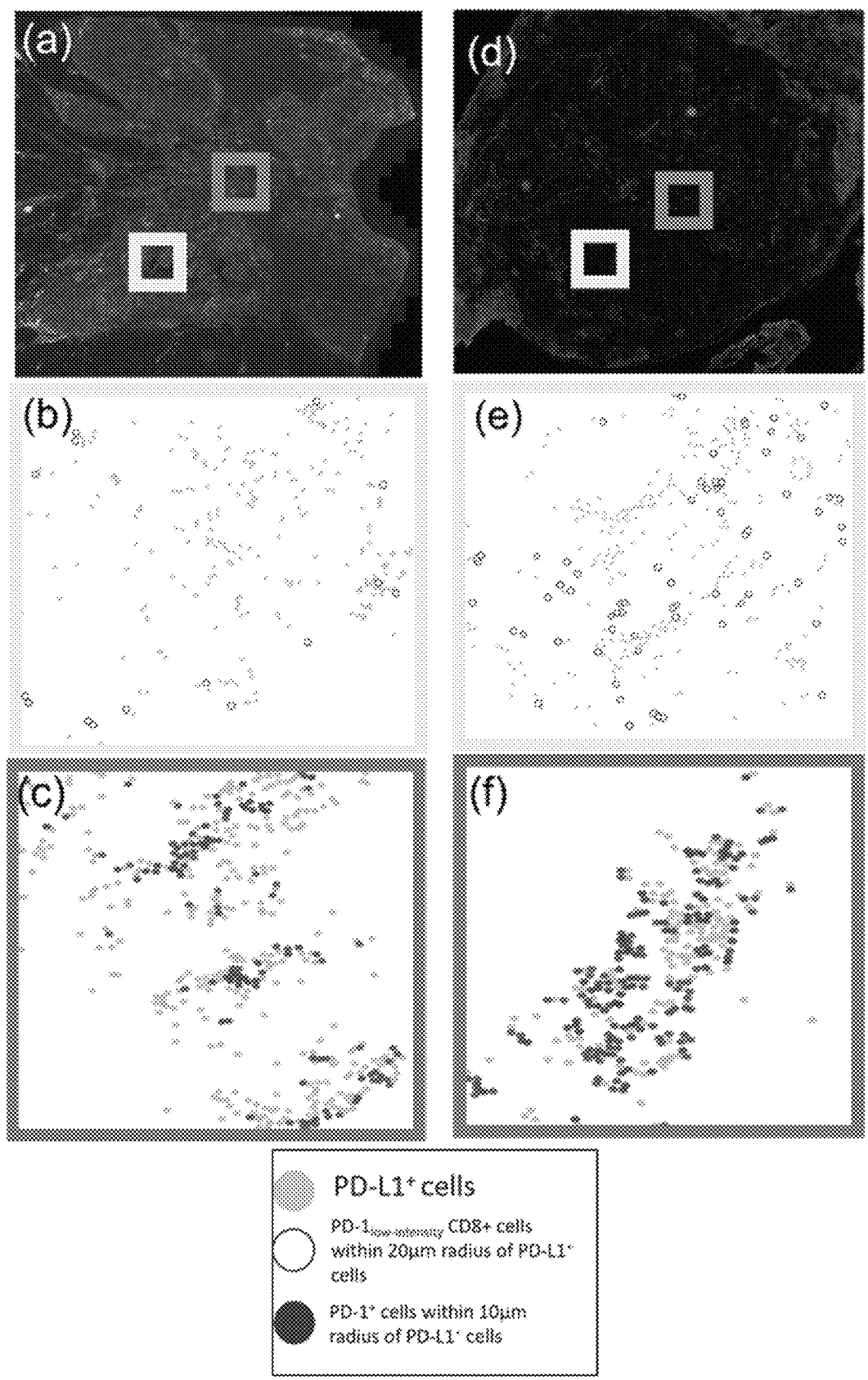
FIG. 15 illustrates exemplary IHC images of non-responders and responders, along with graphical reconstructions showing the locations of PD-L1+ cells (grey dots), PD-$1_{low}$ cells within 20 μm of PD-L1+ cells (white dots), and PD-1+ cells within 10 μm of PD-L1+ cells (black dots). Frame (a) is a raw fluorescent image of a non-responder. Frame (b) is a graphical reconstruction of the white box from frame (a), showing the spatial relationship between PD-L1+ cells and PD-$1_{low}$ cells within 20 μm of PD-L1+ cells in a non-responder. Frame (c) is a graphical reconstruction of the grey box from frame (a), showing the spatial relationship between PD-L1+ cells and PD-1+ cells within 10 μm of a PD-L1+ cell in a non-responder. Frame (d) is a raw fluorescent image of a responder. Frame (e) is a graphical reconstruction of the white box from frame (d), showing the spatial relationship between PD-L1+ cells and PD-$1_{low}$ cells within 20 μm of PD-L1+ cells in a responder. Frame (f) is a graphical reconstruction of the grey box from frame (d), showing the spatial relationship between PD-L1+ cells and PD-1+ cells within 10 μm of a PD-L1+ cell in a responder.
Figure 16A:
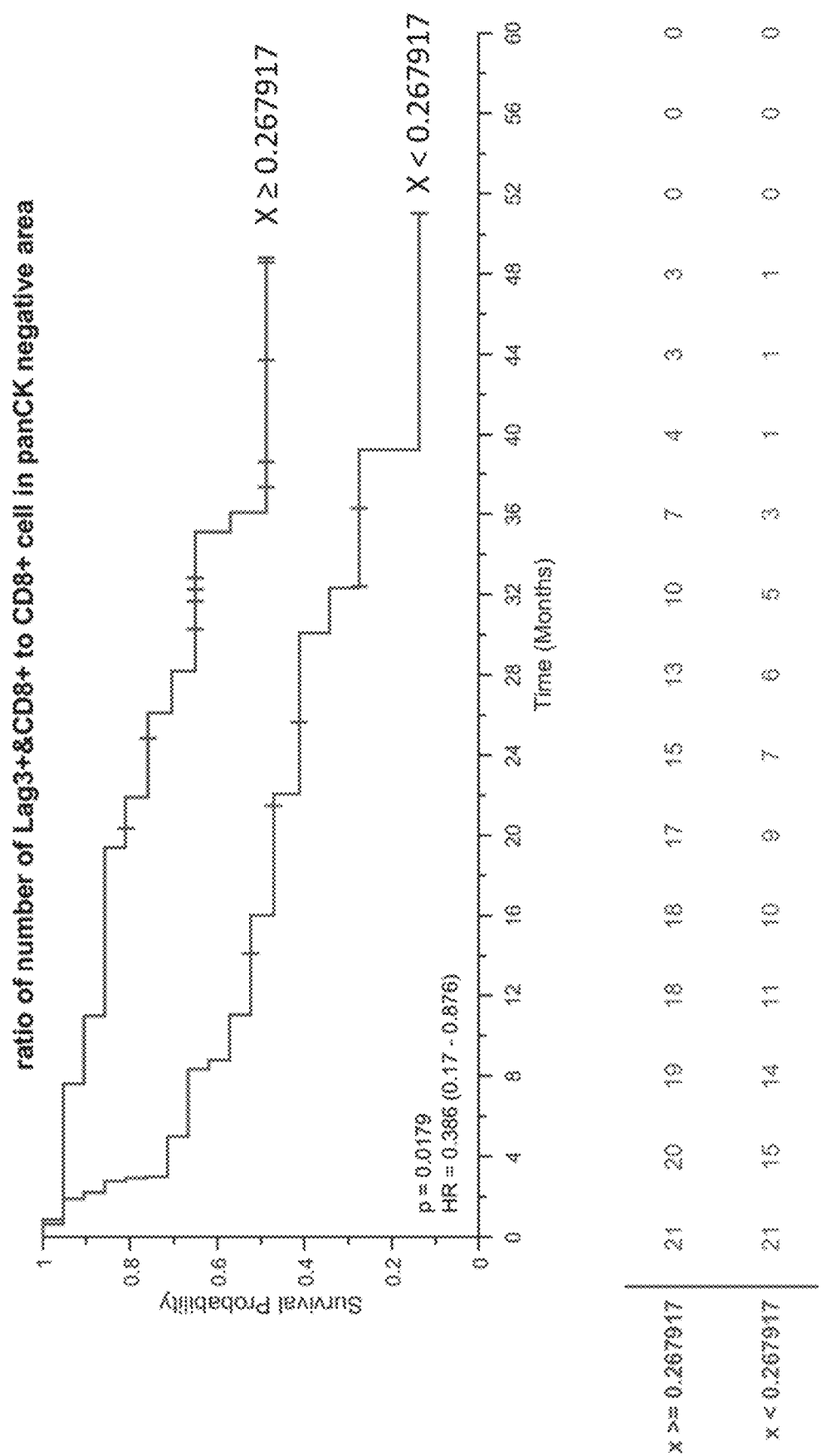
FIG. 16A is a Kaplan-Meier survival curve for prediction of overall survival post-pembrolizumab treatment on the basis of the ratio of the number of Lag3+/CD8+ cells to total CD8+ cells in panCK-negative area.
Figure 16B:
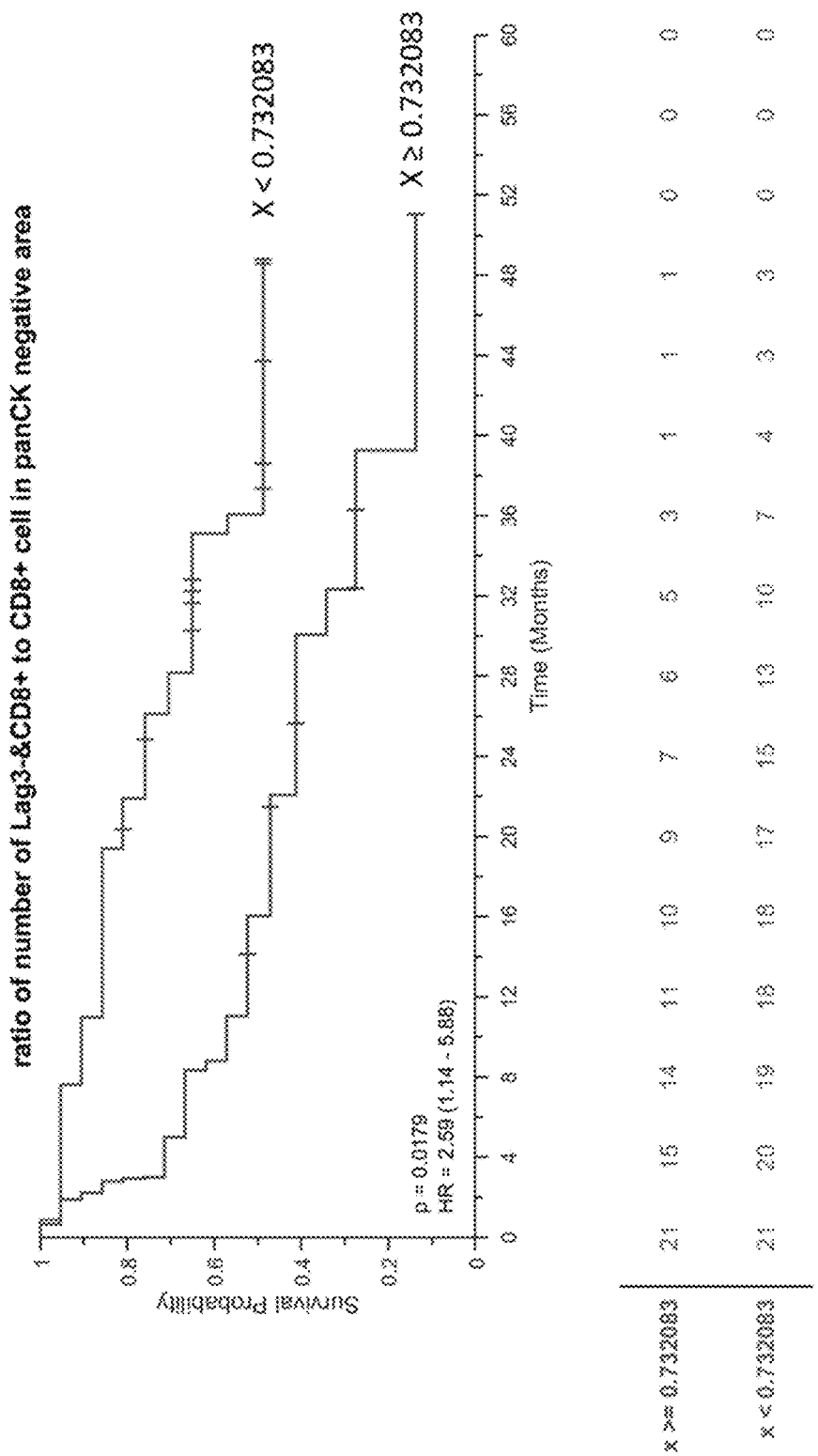
FIG. 16B is a Kaplan-Meier survival curve for prediction of overall survival post-pembrolizumab treatment on the basis of the ratio of number of Lag3−/CD8+ cells to CD8+ cells in panCK-negative area.
Figure 16C:
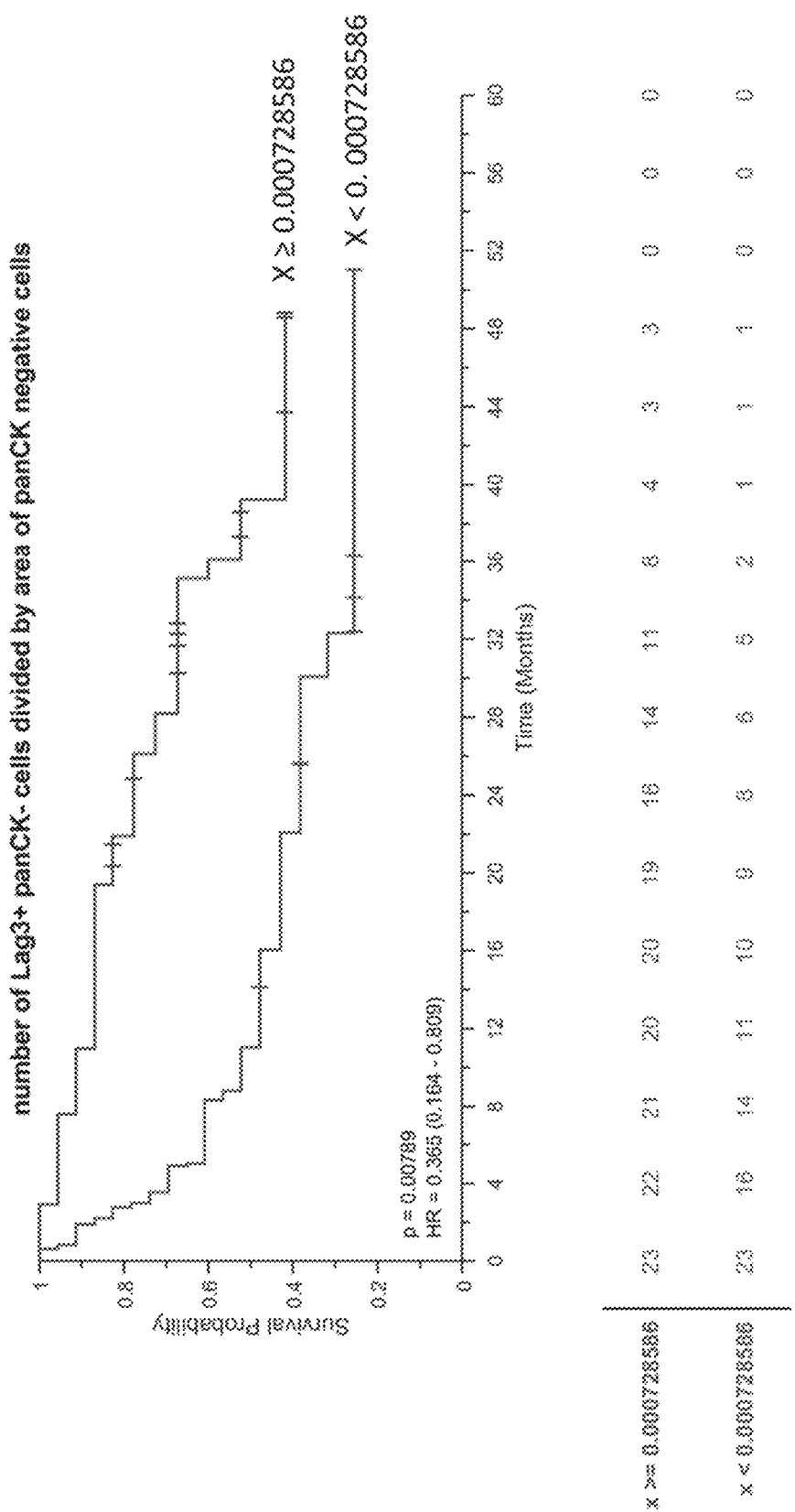
FIG. 16C is a Kaplan-Meier survival curve for prediction of overall survival post-pembrolizumab treatment on the basis of the number of Lag3+/panCK− cells divided by panCK-negative area.
Figure 16D:
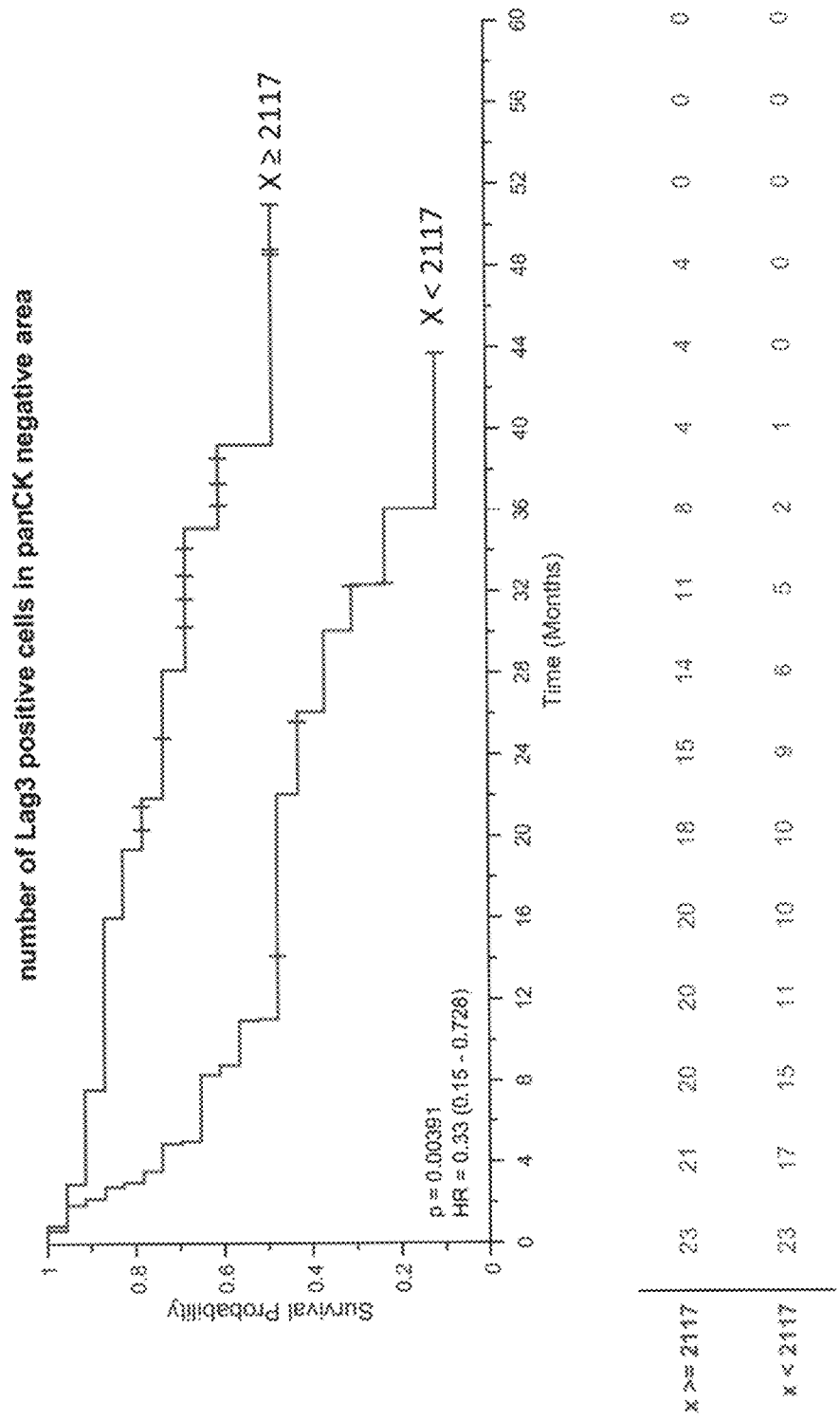
FIG. 16D is a Kaplan-Meier survival curve for prediction of overall survival post-pembrolizumab treatment on the basis of the number of Lag3 positive cells in panCK negative area.
Figure 16E:
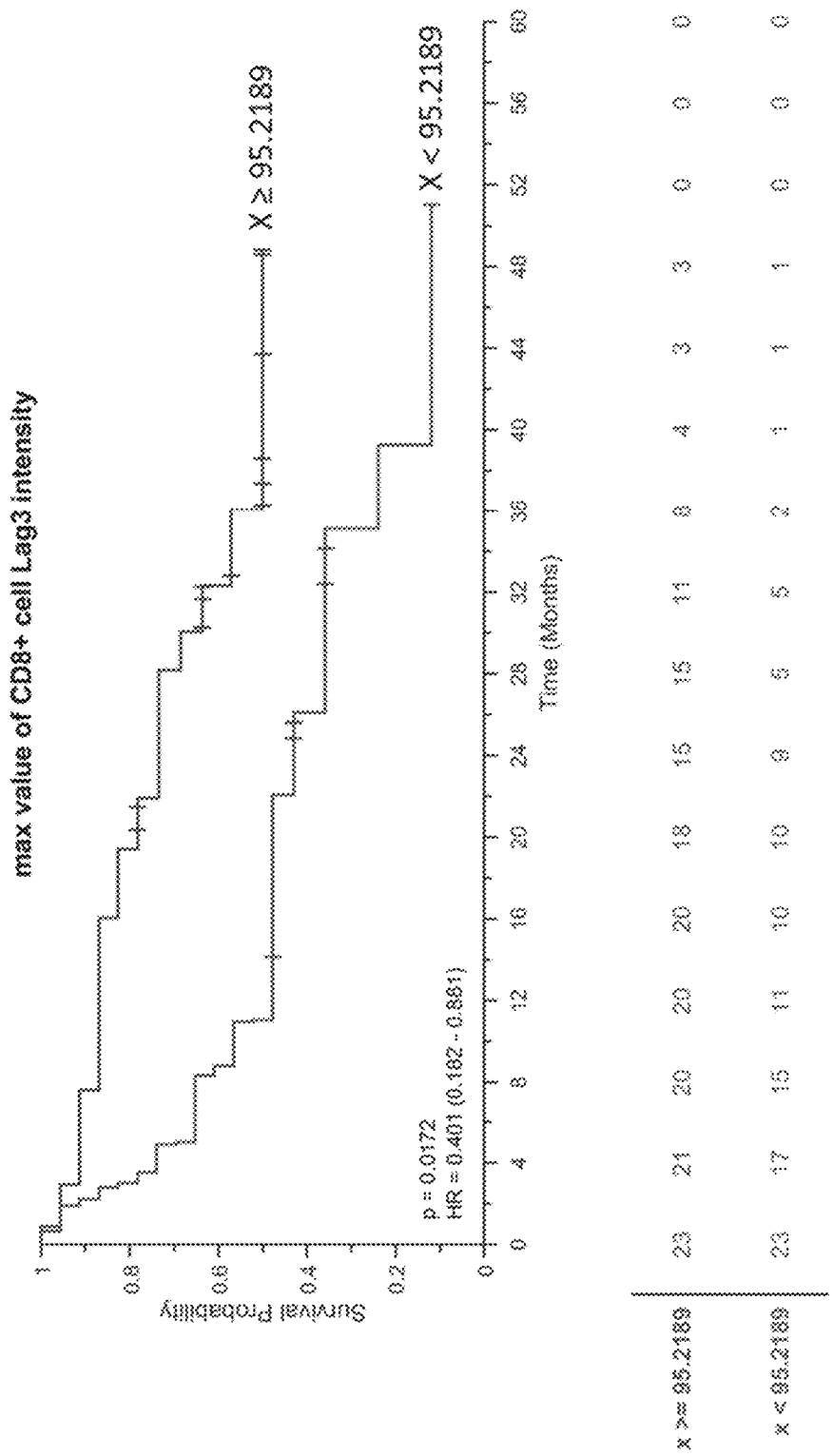
FIG. 16E is a Kaplan-Meier survival curve for prediction of overall survival post-pembrolizumab treatment on the basis of the max value of Lag3 intensity in CD8+ cells.
Figure 16F:
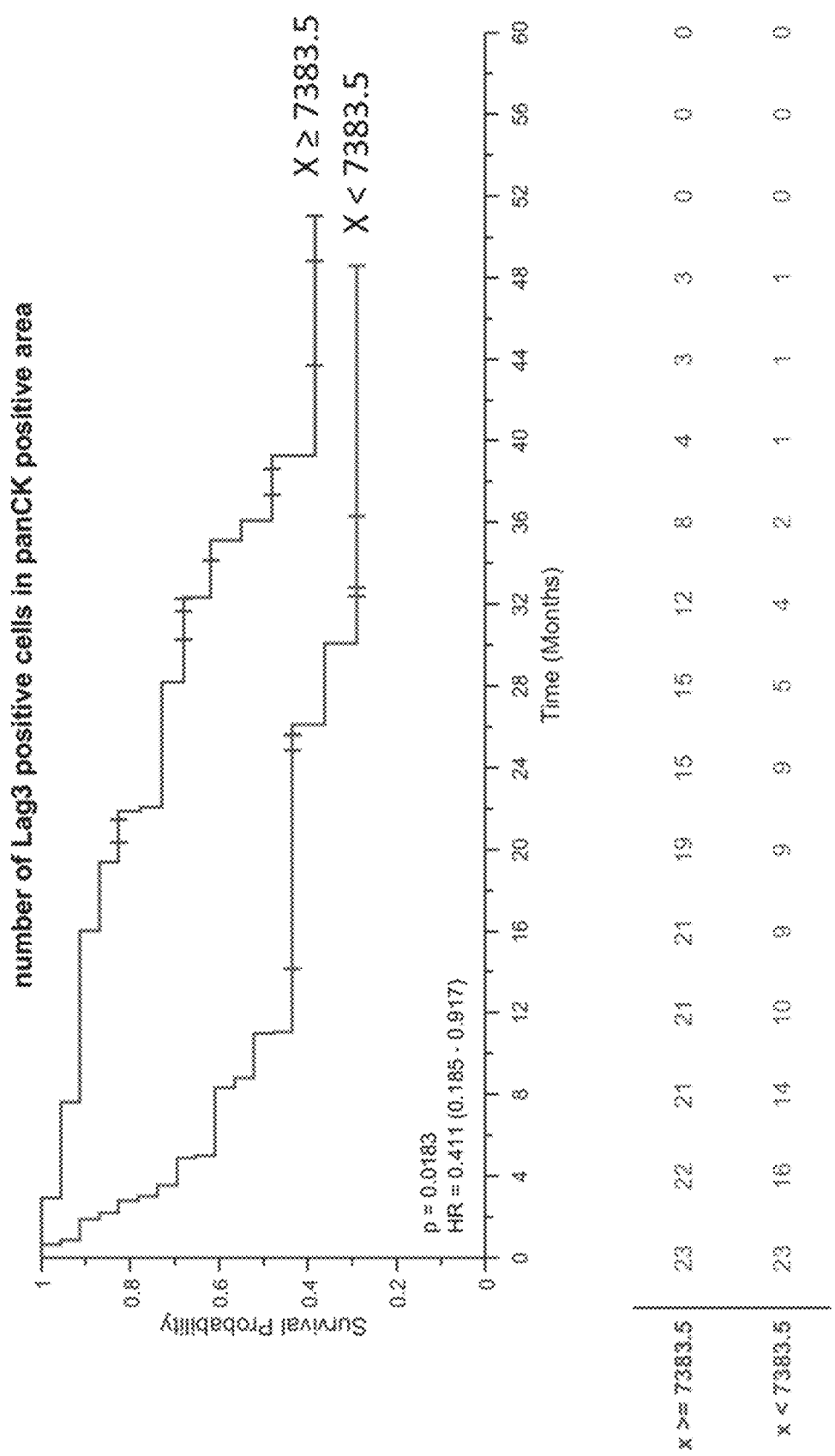
FIG. 16F is a Kaplan-Meier survival curve for prediction of overall survival post-pembrolizumab treatment on the basis of the number of Lag3+ cells in panCK-positive area.
Figure 16G:
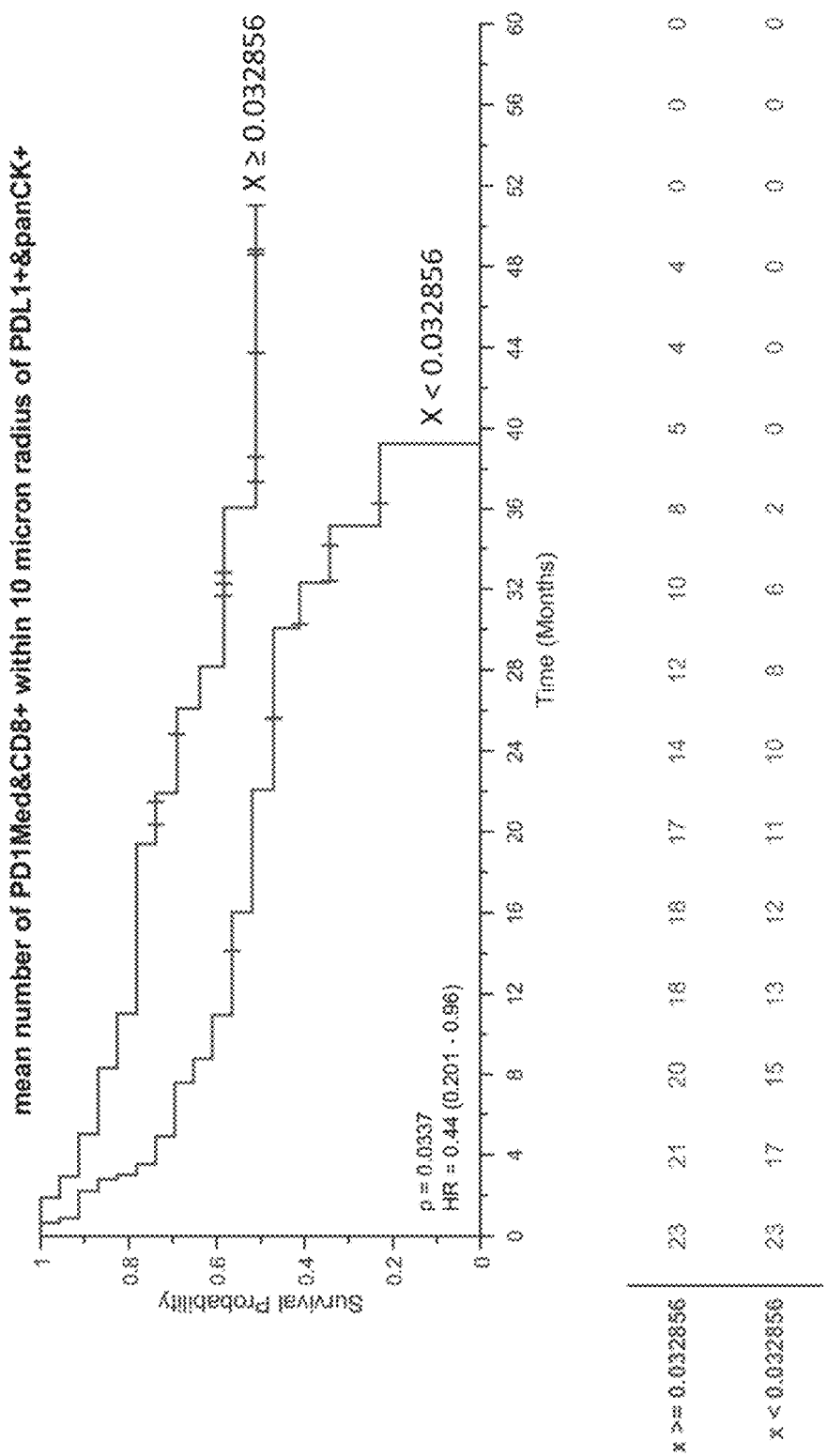
FIG. 16G is a Kaplan-Meier survival curve for prediction of overall survival post-pembrolizumab treatment on the basis of the mean number of PD-$1_{med}$/CD8+ cells within a 10 μm radius of PD-L1+/panCK+ cell.
Figure 16H:
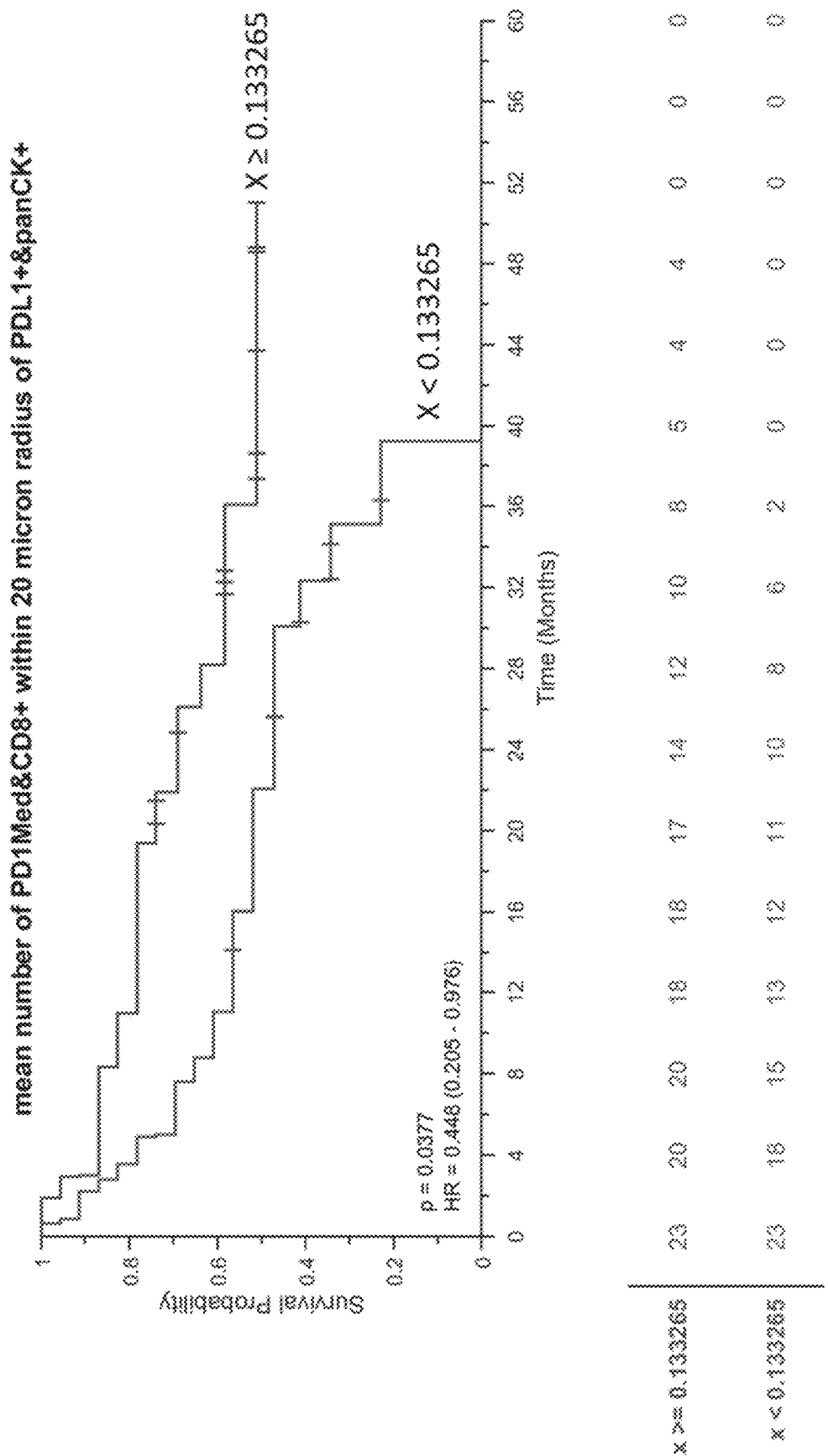
FIG. 16H is a Kaplan-Meier survival curve for prediction of overall survival post-pembrolizumab treatment on the basis of the mean number of PD-$1_{med}$/CD8+ cells within a 20 μm radius of PD-L1+/panCK+ cell.
Figure 16I:
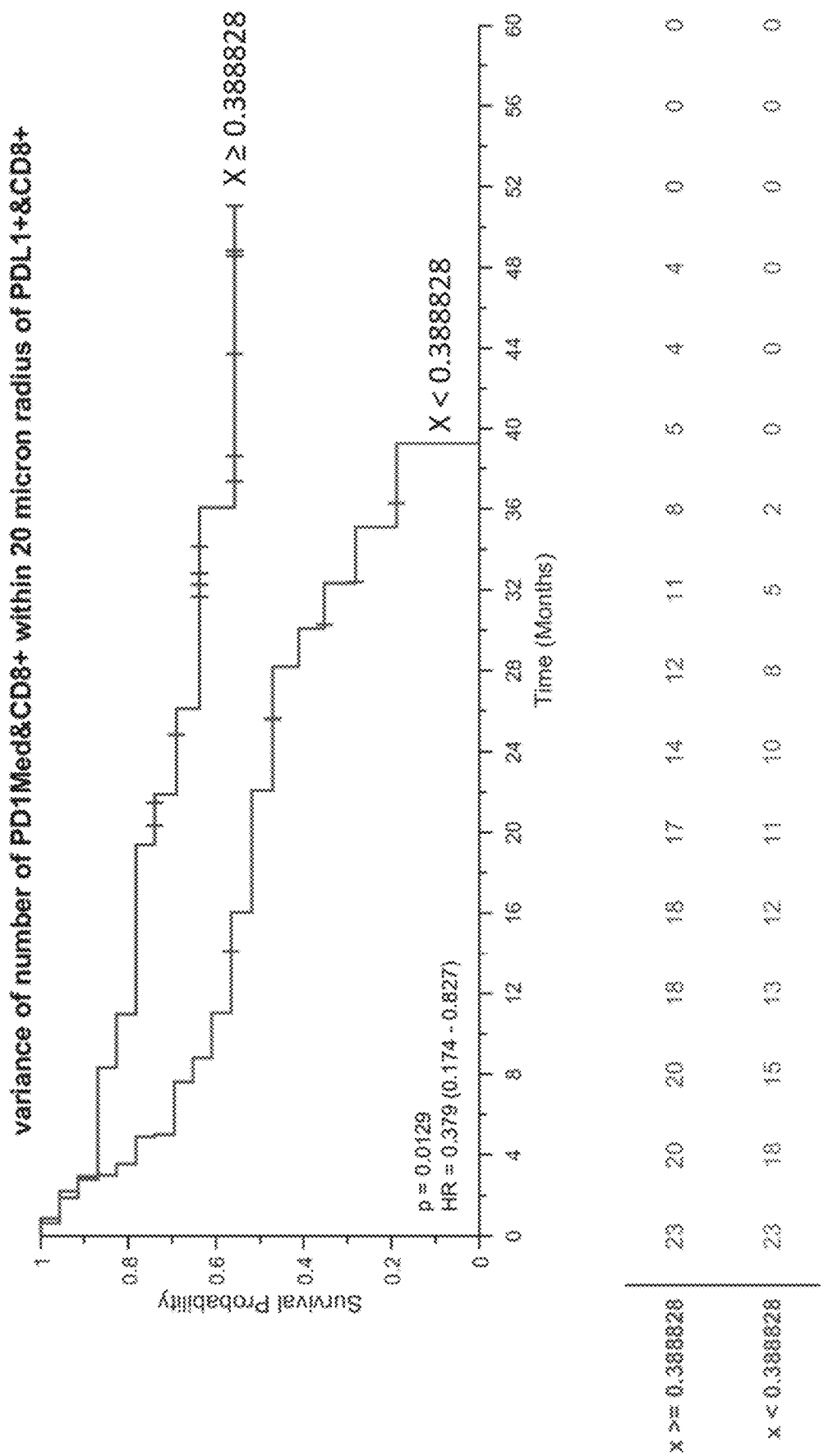
FIG. 16I is a Kaplan-Meier survival curve for prediction of overall survival post-pembrolizumab treatment on the basis of the variance of the number of PD-$1_{med}$/CD8+ cells within a 20 μm radius of PD-L1+/CD8+ cell.
Figure 16J:
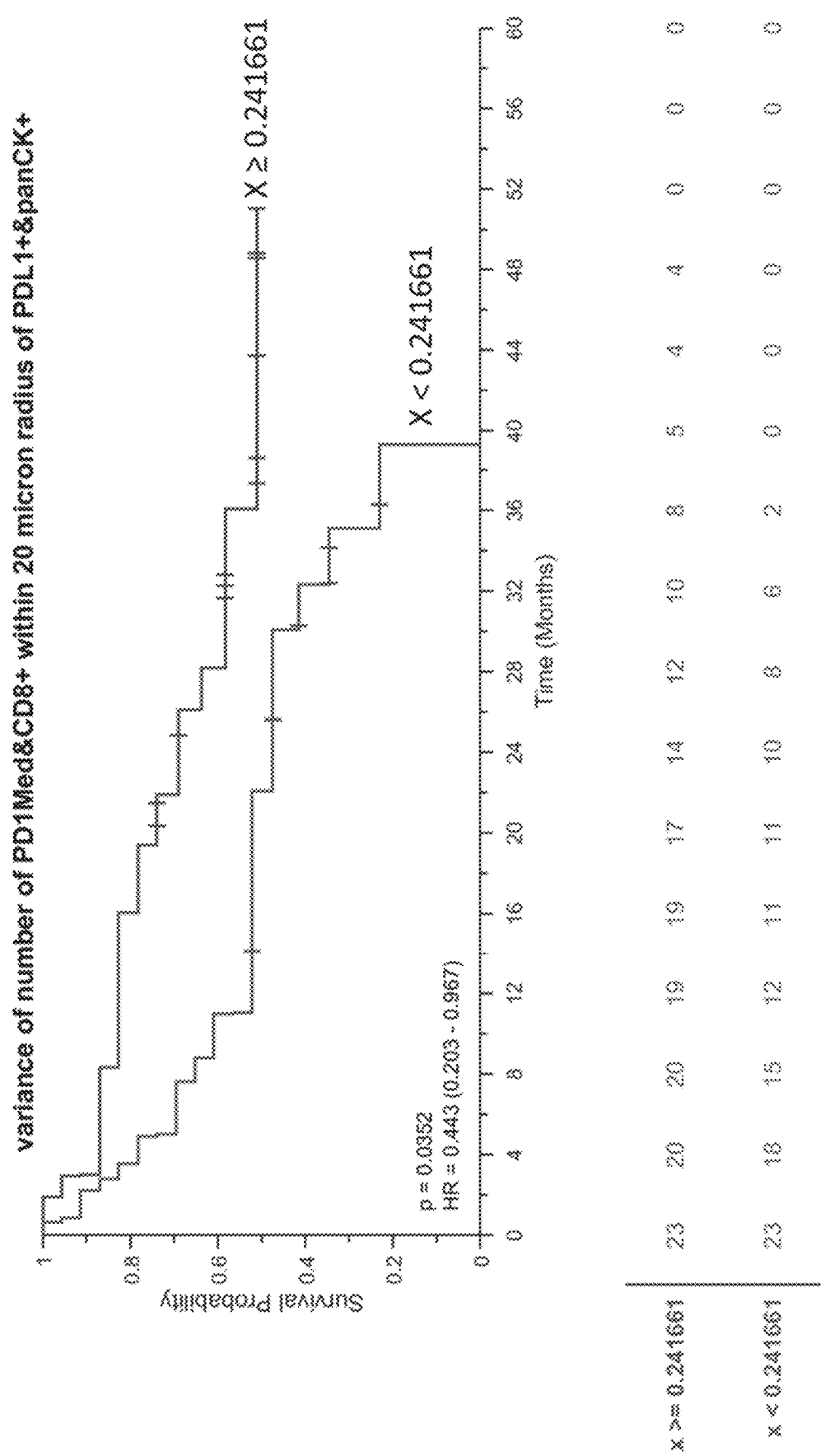
FIG. 16J is a Kaplan-Meier survival curve for prediction of overall survival post-pembrolizumab treatment on the basis of the variance of the number of PD-$1_{med}$/CD8+ cells within a 20 μm radius of PD-L1+/panCK+ cell.
Figure 16K:
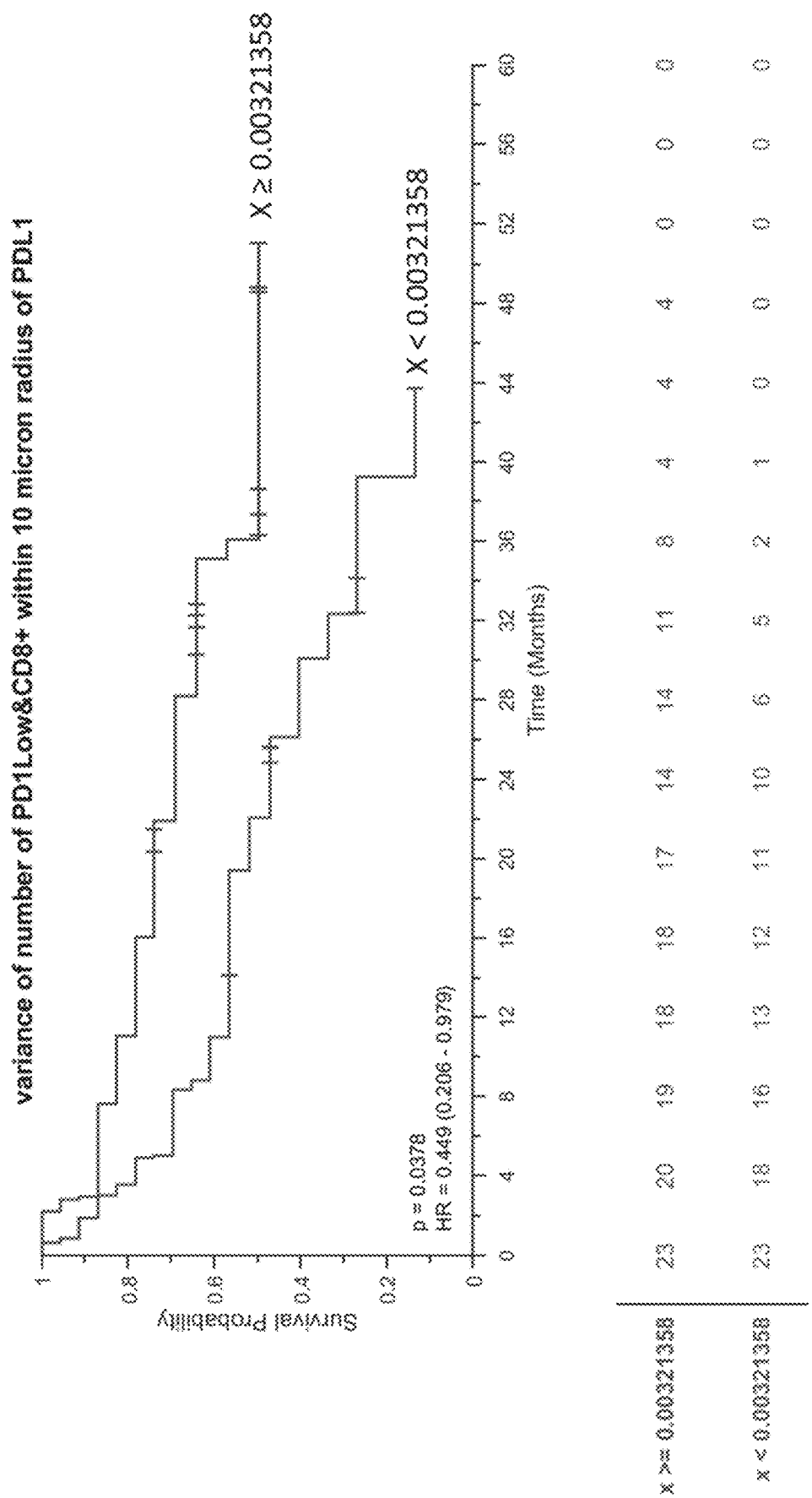
FIG. 16K is a Kaplan-Meier survival curve for prediction of overall survival post-pembrolizumab treatment on the basis of the variance of the number of PD-$1_{low}$/CD8+ cells within a 10 μm radius of a PD-L1+ cell.
Figure 16L:
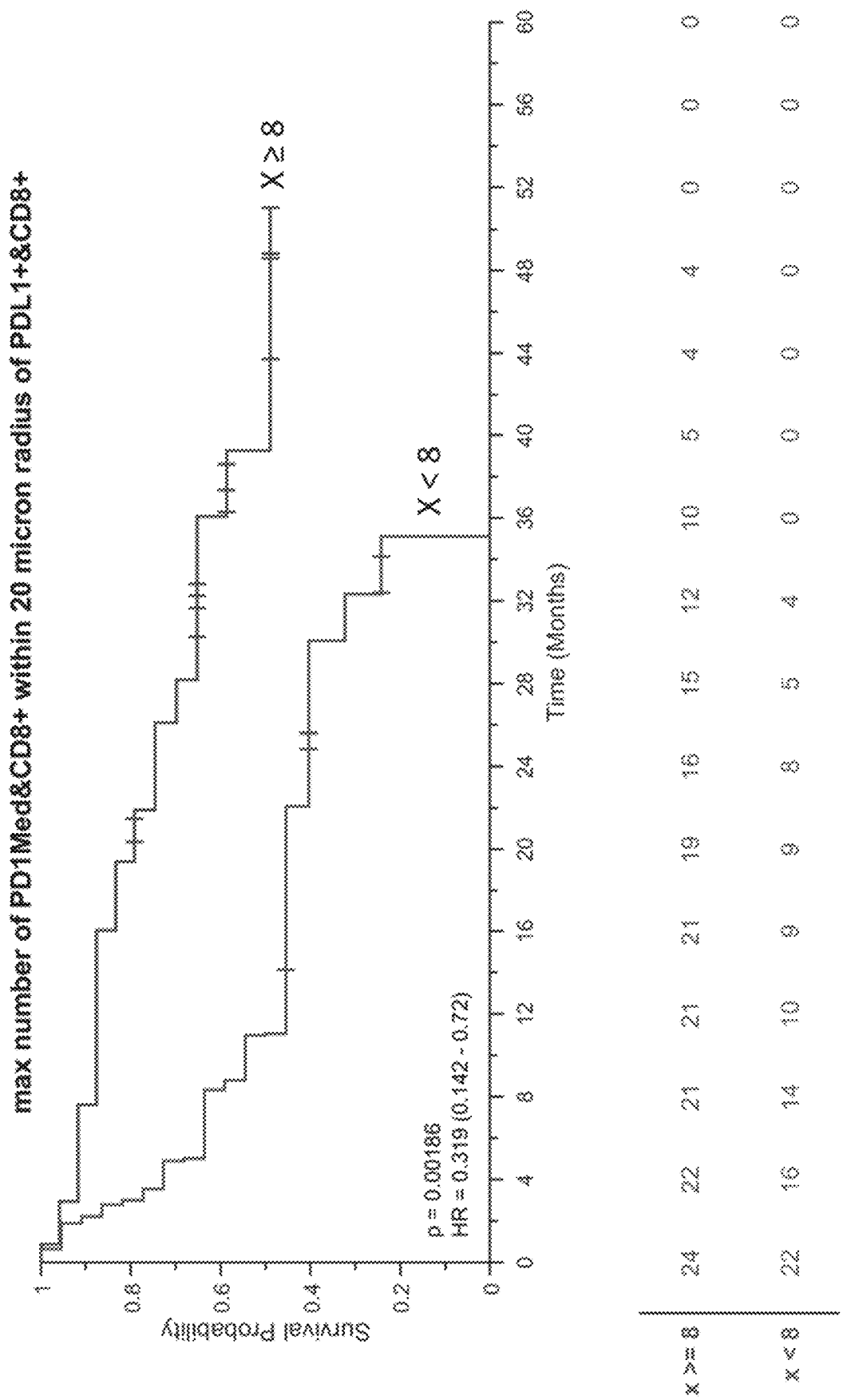
FIG. 16L is a Kaplan-Meier survival curve for prediction of overall survival post-pembrolizumab treatment on the basis of the max number of PD-$1_{med}$/CD8+ cells within a 20 μm radius of a PD-L1+/CD8+ cell.
Figure 16M:
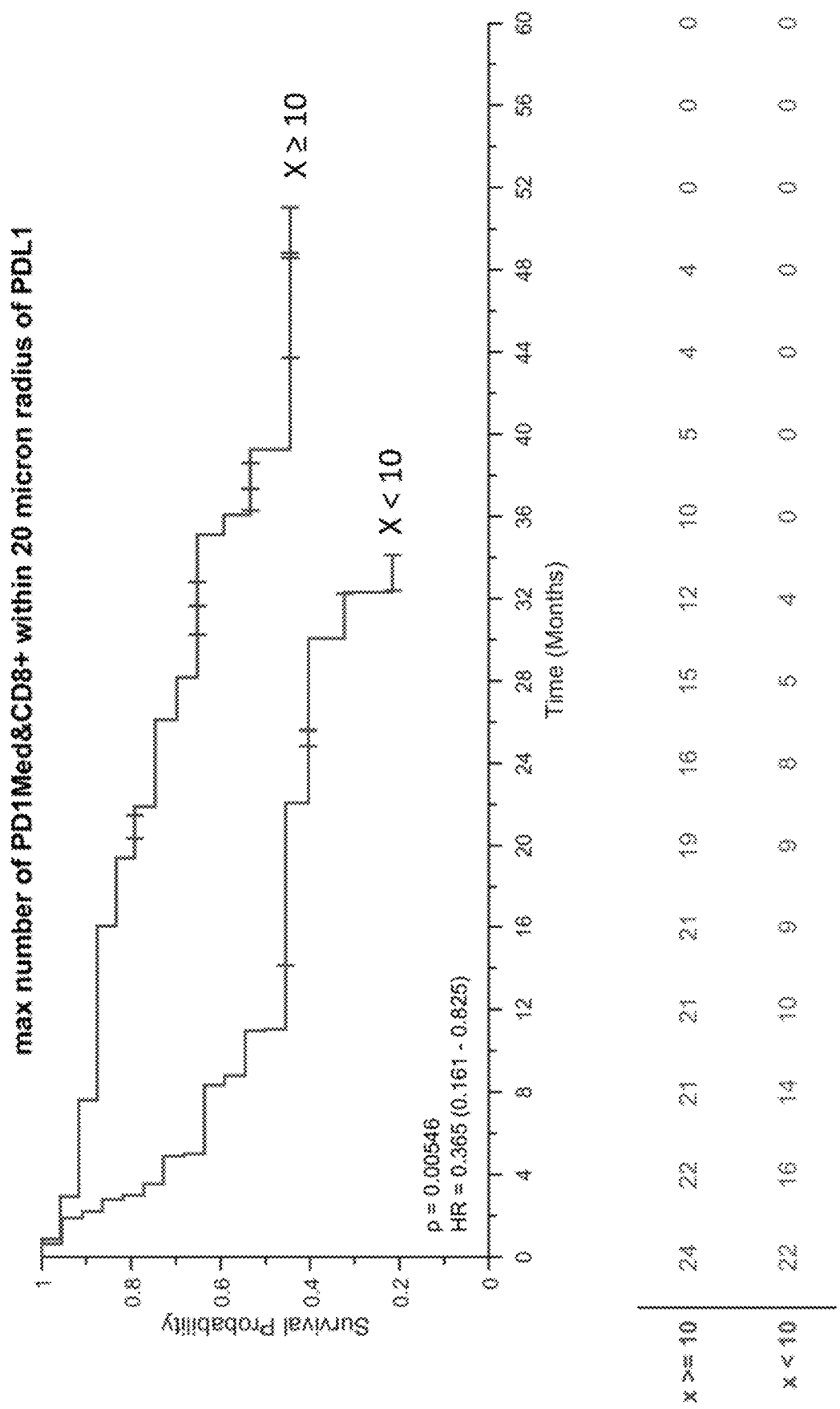
FIG. 16M is a Kaplan-Meier survival curve for prediction of overall survival post-pembrolizumab treatment on the basis of the max number of PD-$1_{med}$/CD8+ cells within a 20 μm radius of a PD-L1+ cell. For each feature metric. the cohort was divided into two groups using the median of a distribution of the feature metric as a cutoff.

FIG. 15 illustrates exemplary IHC images of non-responders, along with graphical reconstructions showing the locations of PD-L1$^+$ cells (grey dots), PD-1$_{low}$ cells within 20 µm of PD-L1+ cells (white dots), and PD-1$^+$ cells within 10 µm of PD-L1+ cells (black dots). As can be seen, there is a similar presence of PD-L1+ cells in non-responders and responders. However, the responder show a higher presence of CD8+ PD-1$_{low}$, cells within 20 µm of PD-L1$^+$ cells in responders and non-responders. Additionally, there is a more uniform distribution of PD-1$^+$ cells within 10 µm of PD-L1+ cells in responders than in non-responders.

II.D. Survival Analysis

Overall survival (OS) data was available for a subset of 46 patients. Survival analysis was conducted for each of the variables of Table 14. The following variables were significantly predictive for a survival benefit: (a) Ratio of the number of Lag3$^+$/CD8$^+$ cells to total CD8$^+$ cells in panCK-negative area; (b) Ratio of number of Lag3$^-$/CD8$^+$ cells to CD8$^+$ cells in panCK-negative area, (c) Number of Lag3$^+$/panCK$^-$ cells divided by panCK-negative area, (d) number of Lag3 positive cells in panCK negative area, (e) max value of Lag3 intensity in CD8$^+$ cells, (f) number of Lag3+ cells in panCK-positive area, (g) mean number of PD-1$_{med}$/CD8+ cells within a 10 µm radius of PD-L1$^+$/panCK$^+$ cell, (h) mean number of PD-1$_{med}$/CD8+ cells within a 20 µm radius of PD-L1$^+$/panCK$^+$ cell, (i) variance of the number of PD-1$_{med}$/CD8+ cells within a 20 µm radius of PD-L1$^+$/CD8$^+$ cell, (j) variance of the number of PD-1$_{med}$/CD8+ cells within a 20 µm radius of PD-L1$^+$/panCK$^+$ cell, (k) variance of the number of PD-1$_{low}$/CD8+ cells within a 10 µm radius of a PD-L1$^+$ cell, (l) max number of PD-1$_{med}$/CD8+ cells within a 20 µm radius of a PD-L1$^+$/CD8$^+$ cell, and (m) max number of PD-1$_{med}$/CD8+ cells within a 20 µm radius of a PD-L1$^+$ cell. For each feature metric, the cohort was divided into two groups using the median of a distribution of the feature metric as a cutoff. Kaplan-Meier survival curves are depicted at FIGS. 16A-16M.

IV. Exemplary Image Analysis System and Clinical Workflow

In clinical practice, the scoring function may be integrated into prognostic analysis and making treatment decisions. After biopsy or surgical resection of the tumor, a representative tissue block showing a tumor cross-section from the patient's tumor sample is chosen for analysis. At least three 4 µm thick sections are cut from this tissue block, and transferred to glass slides. The sections are stained as:
1. IHC negative control (i.e. staining protocol with primary antibody diluent in place of primary antibody);
2. Multiplex IHC including at least PD-L1, PD1, CD8, and LAG3 primary antibodies; and
3. H & E.

All sections are scanned on a slide scanner. Images are transferred to a Digital Pathology system together with slide metadata. Slide metadata includes an identification of the tumor sample and the staining of the slide (H & E, IHC, or negative control) and can either be entered by a user when scanning a slide or automatically obtained from a laboratory information system. The Digital Pathology system uses the slide metadata to trigger the execution of automated calculation of one or more features of Table 9 or Table 16. For example, the feature includes at least Maximum number of CD8$^+$/PD-1low-intensity cells within 20 µm of PD-L1+ cells in epithelial tumor, and optionally further includes "average #PD-1+ cells within 20 µm radius of PD-L1+ cells" and the "max value of Lag3+ intensity on CD8+ cell".

In the Digital Pathology system, a pathologist or expert observer opens the digital image of the H & E slide in viewing software to understand relevant morphologic areas to score. The user then annotates the tumor using annotation tools provided by the viewing software. Typically, the tumor is defined by creating one or more outlines and identifying them as tumor outlines. For this, the user creates additional outlines that intersect with the tumor outline. The intersections define the beginning and end of sections on the tumor outline that are involved in an invasive process. The new outlines are identified as invasive margin.

The user then triggers the automated transfer of the annotations onto the adjacent IHC slide. The Digital pathology system offers a registration function that transfers annotations onto adjacent slides, taking position, orientation, and local deformations of the tissue section into account. The user opens the IHC slide image in the viewer software and controls the location of the automatically registered annotations. The viewer software offers tools to modify and edit annotations if this is necessary. Editing functions include shifting annotations, rotating annotations, and locally modifying their outlines. The user further examines the IHC slide images in the viewer software for tissue, staining, or imaging artifacts. The user delineates such artifact regions with annotations and identifies them to be excluded from analysis.

In the Digital Pathology system, the user may choose one or more IHC slides and triggers the report generation. The user may obtain quality control reports, which may include the following components:
1. A low- to mid-resolution image that shows all tissue on the slide
2. The same low- to mid-resolution image overlaid with the outline and/or transparent colored regions that indicate the morphologic regions of interest like the tumor margin. Furthermore, regions that are annotated to be excluded from the analysis are overlaid in this image.
3. The same low- to mid-resolution image with automatically generated small rectangular markers that indicate the position of high-resolution FOVs for quality control
4. Each of the high-resolution FOVs
5. Each of the high-resolution FOVs overlaid with markers that indicate the presence of each cell phenotype that was determined by automated cell counting.

As an option, the morphologic regions of interest and markers indicating the cells from automated cell counting can also be presented in the viewer software.

The user reviews the QC data and decides to accept or reject the case. For accepted cases, the Digital Pathology system reports quantitative readouts and passes them to a scoring module. These quantitative readouts may include:

1. The area of each morphologic region of interest in mm².
2. The number of cells in each morphologic region of interest.
3. Descriptive statistics that describe the spatial distribution of the cells and/or the spatial relationship between cells of different phenotypes in each morphologic region of interest.

Additional information about the samples may further be input into the Digital Pathology system, such as, for example, MMR status, prior exposure of the subject to a therapy (such as chemotherapy, radiation therapy, and/or a targeted therapy), tumor scores using a TNM staging system, and/or overall tumor stage, and clinical variables (such as age, sidedness of the tumor, number of lymph nodes harvested, and sex of the patient), which may be used by the system to, for example, select an appropriate scoring function to apply to the image. Additionally or alternatively, the user may select an appropriate scoring function based on such criteria or other criteria. The scoring module calculates the score based on the extracted features, which may be reported as a raw number. Additionally, a binning function may be applied to the score to assign the patient to a risk bin (for example, by applying cutoffs between populations based on "likely to respond" or "unlikely to respond" to the checkpoint inhibitor) and/or a population stratification bin (for example, a quartile or decile bin based on score); and/or a feature selection function to rank the score. The clinician reviews the report and discusses results with patient deciding on clinical pathologist-based results, which may then be used to make a treatment decision for the patient.

REFERENCES

Barrera et al., *Computer-extracted features relating to spatial arrangement of tumor infiltrating lymphocytes to predict response to nivolumab in non-small cell lung cancer (NSCLC).* ASCO Annual Meeting 2018: Abstract #: 12115.

Le et al., *PD-1 Blockade in Tumors with Mismatch-Repair Deficiency*, N Engl J Med. 2015 Jun. 25; 372(26):2509-20 ("Le (I)").

Le et al., *Mismatch-repair deficiency predicts response of solid tumors to PD-1 blockade*, Science, 10.1126/science.aan6733 (2017) ("Le (II)").

Li & Tian, *Development of small-molecule immune checkpoint inhibitors of PD-1/PD-L1 as a new therapeutic strategy for tumour immunotherapy*, J. of Drug Targeting, DOI: 10.1080/1061186X.2018.1440400 (published online 20 Feb. 2018).

Nordic Immunohistochemical Quality Control, CK-Pan run 47 (2016), available at http://www.nordiqc.org/downloads/assessments/82_85.pdf (last accessed 4 Oct. 2018) ("NordiQC").

Topalian, Suzanne L., et al. "Safety, activity, and immune correlates of anti-PD-1 antibody in cancer." New England Journal of Medicine 366.26 (2012): 2443-2454.

Wang, et al., *Prediction of recurrence in early stage non-small cell lung cancer using computer extracted nuclear features from digital H&E images.*, Scientific Reports 7.1 (2017): 13543.

Woodcock-Mitchell et al. *Immunolocalization of keratin polypeptides in human epidermis using monoclonal antibodies.* J Cell Biol. 1982; 95(2):580-588.

Yi et al., *Biomarkers for predicting efficacy of PD-1/PD-L1 inhibitors*, Mol Cancer. 2018; 17: 129. (Published online 2018 Aug. 23)

Zhang et al. "Automated 5-plex fluorescent immunohistochemistry with tyramide signal amplification using antibodies from the same species." J Immunother Cancer. 2015; 3(Suppl 2): P111 ("Zhang (I)").

Zhang et al. "An automated 5-plex fluorescent immunohistochemistry enabled characterization of PD-L1 expression and tumor infiltrating immune cells in lung and bladder cancer specimens." Cancer Research 2016, 76(14 Supplement):5117 ("Zhang (II)").

The invention claimed is:

1. A method of scoring a tumor sample for likelihood of responding to a PD-1 axis directed therapy, the method comprising:
   (a) obtaining a digital image of a tumor section from the tumor sample, wherein the tumor section is stained in a multiplex affinity histochemical stain for each of PD-L1, CD8, CD3, CD68, and an epithelial marker (EM⁻);
   (b) extracting a feature metric from a region of interest (ROI) in the image, the feature metric selected from the group consisting of:
   (i) mean distance between CD8⁺ cells in the ROI and closest PD-L1⁺/CD68⁺ cell,
   (ii) mean distance between CD8⁺ cells in the ROI and closest PD-L1⁺/CD3⁺ cells,
   (iii) mean distance between epithelial cells in the ROI and closest CD8⁺ cell,
   (iv) number of PD-L1⁺ epithelial cells in the ROI within 10 μm of a CD8⁺ cell,
   (v) number of PD-L1⁺ epithelial cells in the ROI within 30 μm of a CD8⁺ cell
   (vi) number of CD8⁺ cells in the ROI within 10 μm of an epithelial cell
   (vii) number of CD8⁺ cells in the ROI within 30 μm of an epithelial cell
   (viii) density of PD-L1⁺/CD3⁺ cells in the ROI
   (ix) density of PD-L1⁺/CD3⁺/CD8⁻ cells in the ROI
   (x) density of PD-L1⁺/CD8⁺ cells in the ROI
   (xi) density of PD-L1⁺/CD68⁺ cells in the ROI
   (xii) density of PD-L1⁺ epithelial cells in the ROI
   (xiii) density of CD3⁺ cells in the ROI
   (xiv) density of CD8⁺ cells in the ROI
   (xv) density of CD68⁺ cells in the ROI
   (xvi) density of epithelial cells in the ROI
   (xvii) ratio between area occupied by PD-L1⁺ epithelial cells in the ROI and the total area of the ROI
   (xviii) ratio between area occupied by epithelial cells in the ROI and the total area of the ROI
   (xix) ratio between number of PD-L1⁺ epithelial cells in the ROI and the total number of epithelial cells in the ROI
   (xx) ratio between number of PD-L1⁺/CD3⁺ cells in the ROI and the total number of CD3⁺ cells in the ROI
   (xxi) ratio between number of PD-L1⁺/CD3⁺/CD8⁻ cells in the ROI and the total number of CD3⁺/CD8⁻ cells in the ROI
   (xxii) ratio between number of PD-L1⁺/CD8⁺ cells in the ROI and the total number of CD8⁺ cells in the ROI
   (xxiii) ratio between number of PD-L1⁺/CD68⁺ cells in the ROI and the total number of CD68⁺ cells in the ROI
   (xxiv) ratio between number of PD-L1⁺/CD3⁺/CD8⁻ cells in the ROI and the total number of CD3⁺/CD8⁻ cells in the ROI,
   (xxv) ratio between number of CD3⁺/CD8⁻ cells in the ROI and the total number of CD3⁺ cells in the ROI,
   (xxvi) total area occupied by CD3⁺ cells; and
   (c) applying a scoring function to a feature vector comprising the feature metric to generate a score indicative of the likelihood that the tumor will respond to the PD-1 axis directed therapy.

2. The method of claim 1, wherein the ROI is selected from the group consisting of a tumor ROI, a stromal ROI, an epithelial marker-positive (EM⁺) ROI, an epithelial marker-negative (EM⁻) ROI, a Peritumor inner (PI) ROI, a Peritumor outer (PO) ROI, and a Peritumor region (PR) ROI.

3. The method of claim 2, wherein the ROI is the stromal ROI or the EM⁻ ROI and the feature vector comprises one or more features metrics selected from the group consisting of:
   (xx) ratio between number of PD-L1⁺/CD3⁺ cells in the ROI and the total number of CD3⁺ cells in the ROI,
   (xxii) ratio between number of PD-L1⁺/CD8⁺ cells in the ROI and the total number of CD8⁺ cells in the ROI,
   (xxiii) ratio between number of PD-L1⁺/CD68⁺ cells in the ROI and the total number of CD68⁺ cells in the ROI, and
   (xxiv) ratio between number of PD-L1⁺/CD3⁺/CD8⁻ cells in the ROI and the total number of CD3+CD8⁻ cells in the ROI.

4. The method of claim 3, wherein the feature vector comprises each of:
   Ratio between number of PD-L1⁺/CD68⁺ cells in the stromal ROI or the EM⁻ ROI and the total number of CD68⁺ cells in the stromal ROI or the EM⁻ ROI,
   Ratio between number of PD-L1⁺/CD3⁺/CD8⁻ cells in the stromal ROI or the EM ROI and the total number of CD3⁺/CD8⁻ cells in the stromal ROI or the EM⁻ ROI, and
   Ratio between number of PD-L1⁺/CD3⁺ cells in the stromal ROI or the EM⁻ ROI and the total number of CD3⁺ cells in the stromal ROI or the EM⁻ ROI.

5. The method of claim 2, wherein the ROI is the tumor ROI or the EM⁺ ROI and the feature vector comprises one or more features metrics selected from the group consisting of:
   (i) mean distance between CD8⁺ cells in the EM⁺ ROI OR tumor ROI and closest PD-L1⁺/CD68⁺ cell,
   (ix) PD-L1⁺/CD3⁺/CD8⁻ density in the ROI,
   (xx) ratio between number of PD-L1⁺/CD3⁺ cells in the ROI and the total number of CD3⁺ cells in the ROI,
   (xxii) ratio between number of PD-L1⁺/CD8⁺ cells in the EM⁺ ROI OR tumor ROI and the total number of CD8⁺ cells in the EM⁺ ROI OR tumor ROI,
   (xxiii) ratio between number of PD-L1⁺/CD68⁺ cells in the ROI and the total number of CD68⁺ cells in the ROI,
   (xxiv) ratio between number of PD-L1⁺/CD3⁺/CD8⁻ cells in the ROI and the total number of CD3⁺/CD8⁻ cells in the ROI, and (XXV) ratio between number of CD3$^+$/CD8$^-$ cells in the EM$^+$ ROI OR tumor ROI and the total number of CD3$^+$ cells in the EM$^+$ ROI OR tumor ROI.

6. The method of claim 1, wherein the ROI is derived from a digital image of a morphologically stained section of the tumor sample, wherein the morphologically stained section and the multiplex affinity histochemical stained sample are serial sections.

7. The method of claim 1, wherein the ROI is identified by a user in the digital image of the morphologically stained section and automatically registered to the digital image of the multiplex affinity histochemical stained section.

8. A method of scoring a tumor sample for likelihood of responding to a PD-1 axis directed therapy, the method comprising:
  (a) obtaining a digital image of a tumor section from the tumor sample, wherein the tumor section is stained in a multiplex affinity histochemical stain for each of PD-1, PD-L1, CD8, Lag3, and one or more epithelial markers;
  (b) extracting a feature metric from a region of interest (ROI) in the image, the feature metric selected from the group consisting of the feature metrics listed in Table 9; and
  (c) applying a scoring function to a feature vector comprising the feature metric to generate a score indicative of the likelihood that the tumor will respond to the PD-1 axis directed therapy.

9. The method of claim 8, wherein the ROI is selected from the group consisting of a tumor ROI, a stromal ROI, an epithelial marker-positive (EM$^+$) ROI, an epithelial marker-negative (EM$^-$) ROI, a Peritumor inner (PI) ROI, a Peritumor outer (PO) ROI, and a Peritumor region (PR) ROI.

10. The method of claim 8, wherein the feature metric is selected from the group consisting of:
  (i) max number of PD-1$_{Low}$/CD8$^+$ within a 20 μm radius of PD-L1$^+$/CD8$^+$ cells,
  (ii) max value of CD8$^+$ cell PD-L1 intensity,
  (iii) ratio of number of PD-1$^+$/PD-L1$^-$/Lag3$^+$/CD8$^+$ cells to CD8$^+$ cells in epithelial area,
  (iv) spatial variance number of PD-1$^+$ cells within 20 μm radius of PD-L1$^+$ cells,
  (v) max value of all cell PD-L1 intensity,
  (vi) number of Lag3 positive cells in EM$^+$ ROI,
  (vii) density of PD-L1$^+$/EM$^-$ cells in EM$^-$ ROI,
  (viii) Number of PD-L1$^+$ cells in EM$^+$ ROI,
  (ix) Number of PD-L1$^+$ cells in EM$^-$ ROI,
  (x) Number of PD-1$^+$ cells in EM$^-$ ROI,
  (xi) max number of PD-1$_{Low}$/CD8$^+$ cells within 20 μm radius of PD-L1$^+$ cell,
  (xii) mean number of PD-1$_{Low}$/CD8$^+$ cells within 20 μm radius of PD-L1$^+$ cell,
  (xiii) max value Lag3 intensity from CD8$^+$Lag3$^+$ cells,
  (xiv) Number of CD8$^+$ cells in EM$^+$ ROI,
  (xv) Variance in number of PD-1$_{Low}$/CD8$^+$ cells within 20 μm radius of PD-L1$^+$/CD8$^+$ cells,
  (xvi) Average distance from PD-L1$^+$ cells to its nearest PD-1$^+$ cell,
  (xvii) max number of PD-1$_{Low}$/CD8$^+$ cells within 20 μm radius of PD-L1$^+$/EM$^+$ cell,
  (xviii) Standard deviation of distance from PD-L1$^+$ cells in the ROI to its nearest PD-1$^+$ cell,
  (xix) Ratio of number of Lag3$^+$/CD8$^+$ cells to number of CD8$^+$ cells in EM$^+$ ROI,
  (xx) Ratio of number of PD-L1$^+$/CD8$^+$ cells to number of CD8$^+$ cells in EM$^+$ ROI,
  (xxi) Mean number of PD-1$_{Low}$/CD8$^+$ cells within 10 μm radius of PD-L1$^+$ cells,
  (xxii) Variance in number of PD-1$_{Low}$/CD8$^+$ cells within 10 μm radius of PD-L1$^+$ cells,
  (xxiii) Mean value of PD-1 intensity from all PD-1$^+$ cells,
  (xxiv) Min value of Lag3 intensity from all Lag3$^+$ cells,
  (xxv) Density of PD-L1$^+$/EM$^+$ cells in EM$^-$ ROI,
  (xxvi) max number of PD-1$_{Low}$/CD8$^+$ cells within 10 μm radius of PD-L1$^+$ cell,
  (xxvii) Number of PD-1$^+$ cells in EM$^+$ ROI,
  (xxviii) ratio of number of PD-1$^+$/PD-L1$^-$/Lag3$^+$/CD8$^+$ cells to CD8$^+$ cells in EM$^-$ ROI, and
  (xxix) Max value of Lag3 intensity from CD8$^+$/Lag3$^+$ cells,
  (xxx) Ratio of number of Lag3$^+$/CD8$^+$ cells to number of CD8$^+$ cells in EM$^-$ ROI, and
  (xxxi) number of Lag3 positive cells in EM$^+$ ROI.

11. The method of claim 8, wherein the feature metric is selected from the group consisting of:
  Maximum number of CD8$^+$/PD-1$_{low}$ cells within 20 μm of PD-L1$^+$ cells in the EM+ ROI o the tumor ROI,
  Mean number of PD-1$_{Low}$/CD8$^+$ cells within 20 μm radius of PD-L1$^+$ cells,
  Max value of Lag3 intensity in CD8$^+$/Lag3$^+$ cells,
  Average number of PD-1$^+$ cells within 20 μm radius of PD-L1$^+$ cells, and
  Max value of Lag3$^+$ intensity on CD8$^+$ cell.

12. The method of claim 8, wherein the feature vector comprises each of:
  Maximum number of CD8$^+$/PD-1$_{Low}$ cells within 20 μm of PD-L1$^+$ cells in EM$^+$ ROI,
  Mean number of PD-1$_{Low}$/CD8$^+$ cells within 20 μm radius of PD-L1$^+$ cells,
  Max value of Lag3 intensity in CD8$^+$/Lag3$^+$ cells,
  Average number of PD-1$^+$ cells within 20 μm radius of PD-L1$^+$ cells, and
  Max value of Lag3$^+$ intensity on CD8$^+$ cell.

13. The method of claim 8, wherein the feature metric is selected from the group consisting of:
  Ratio of the number of Lag3$^+$/CD8$^+$ cells to CD8$^+$ cells in the EM$^-$ area,
  Number of Lag3/EM$^-$ cells divided by an area of the EM$^-$ ROI,
  Number of Lag3$^+$ cells in the EM$^-$ ROI,
  Max value of Lag3 intensity in CD8$^+$ cells,
  Number of Lag3$^+$ cells in the EM$^+$ ROI,
  Mean number of PD-1$_{Med}$/CD8$^+$ cells within 10 μm radius of PD-L1$^+$/EM$^+$ cells,
  Mean number of PD-1$_{Med}$/CD8$^+$ cells within 20 μm radius of PD-L1$^+$/EM$^+$ cells,
  Variance of PD-1$_{Med}$/CD8$^+$ cells within 20 μm radius of PD-L1$^+$/CD8$^+$ cells,
  Variance of PD-1$_{Med}$/CD8$^+$ cells within 20 μm radius of PD-L1$^+$/EM$^+$ cells,
  Variance of PD-1$_{Low}$/CD8$^+$ cells within 10 μm radius of PD-L1$^+$ cells,
  Max number of PD-1$_{Med}$/CD8$^+$ cells within 20 μm radius of PD-L1$^+$/CD8$^+$ cells, and
  Max number of PD-1$_{Med}$/CD8$^+$ cells within 20 μm radius of PD-L1$^+$ cells.

14. The method of claim 8, wherein the ROI is derived from a digital image of a morphologically stained section of the tumor sample, wherein the morphologically stained section and the multiplex affinity histochemical stained sample are serial sections.

15. The method of claim 9, wherein the ROI is identified by a user in the digital image of the morphologically stained section and automatically registered to the digital image of the multiplex affinity histochemical stained section.

16. The method of claim 1, wherein the scoring function is derived from a modeling function selected from the group consisting of quadrant discriminant analysis (QDA), Linear discriminant analysis (LDA), Support vector machine (SVM), and Artificial neural network (ANN).

17. The method of claim 16, wherein the scoring function is a QDA model fit to the selected features to predict response to treatment, and wherein the treatment outcomes used to fit the QDA model are grouped together in a configuration selected from the group consisting of:
progressive disease (PD) versus stable disease (SD) versus partial response (PR)+ complete response (CR);
PD versus SD+PR+CR; and
PD+SD vs. PR+CR.

18. A method of selecting a patient to receive a PD-1 axis directed therapy, the method comprising:
generating a score of the method of claim 1,
comparing the score to a pre-determined cutoff value, and
selecting the patient to receive the PD-1 axis therapy or an alternate therapy based on whether the score is above or below the pre determined cutoff value.

19. A method of treating a patient with a PD-1 axis directed therapy, the method comprising:
selecting a patient to receive the PD-1 axis directed therapy according of the method of claim 18; and
administering the PD-1 axis directed therapy to the patient.

20. The method of claim 19, wherein the PD-1 axis directed therapy is a PD-1 specific monoclonal antibody or a PD-L1 specific monoclonal antibody.

21. The method of claim 19, wherein the PD-1 axis directed therapy is selected from the group consisting of pembrolizumab, nivolumab, atezolizumab, avelumab, durvalumab, cemiplimab, tislelizumab, and LY3300054.

22. A method of developing a scoring function for predicting response of a tumor to a PD-1 axis directed therapy is disclosed, the method comprising:
(a) obtaining:
(i) a set of digital images of tumor tissue samples obtained from a plurality of patients prior to treatment with the PD-1 axis directed therapy, wherein at least one digital image for each patient is a digital image of a tissue sections stained in a multiplex affinity histochemical stain for each of one or more epithelial markers, one or more immune cell markers, and one or more PD-1 axis pathway markers; and
(ii) post-treatment response data for each patient;
(b) extracting a plurality of feature metrics from the digital images of the multiplexed stained tissue section, the plurality of feature metrics selected from the group consisting of the features of Table 4;
(c) applying the feature selection function to the extracted plurality of feature metrics and the post-treatment response data to obtain a rank of each feature for the strength of correlation to response to the PD-1 axis directed therapy;
(d) applying a modeling function to one or more of the ranked features and the post-treatment response data to generating a plurality of candidate models predictive of the response to the checkpoint inhibitor therapy and testing each candidate model for concordance with response; and
(e) selecting the candidate model having the highest concordance to the response as the scoring function.

23. The method of claim 22, wherein the multiplex affinity histochemical stain comprises histochemical stain using biomarker-specific reagents for each of PD-L1, CD8, CD3, CD68 and an epithelial marker (EM⁻) (panel 1), and the features are selected from the group consisting of the features in Table 4, left column.

24. The method of claim 22, wherein the multiplex affinity histochemical stain comprises histochemical stain using biomarker-specific reagents for each of PD-L1, PD1, CD8, LAG3, and an epithelial marker (EM⁻) (panel 2), and the features are selected from the group consisting of the features in Table 4, right column.

25. The method of claim 22, wherein the feature selection function is selected from the group consisting of ensemble feature selection methods (including, for example, a Random Forest function), filter methods (including, for example, Mutual information based functions, (mRMR)/ correlation coefficient based functions, and Relief based functions), and/or an embedded feature selection function (such as an elastic net/least absolute shrinkage function or a selection operator (LASSO) functions).

26. The method of claim 22, wherein the candidate models are made using one or more of the top 25, top 20, top 15, top 10, top 9, top 8, top 7, top 6, top 5, top 4 or top 3 features identified by the feature selection function.

27. The method of claim 26, wherein the candidate models use at least 1, at least 2, at least 3, at least 4, or at least 5 features identified in the top 10 features of the feature selection function.

28. The method of claim 26, wherein the candidate models include at least one feature present in the top 5 features of at least 2 feature selection functions.

29. The method of claim 22, wherein the modeling function is selected from the group consisting of quadrant discriminant analysis (QDA), Linear discriminant analysis (LDA), Support vector machine (SVM), and Artificial neural network (ANN).

30. The method of claim 29, wherein said scoring function is a QDA model fit to the selected features to predict response to treatment.

31. The method of claim 30, wherein the treatment outcomes used to fit the QDA model are grouped together in a configuration selected from the group consisting of:
progressive disease (PD) versus stable disease (SD) versus partial response (PR)+ complete response (CR);
PD vs. SD+PR+CR; and
PD+SD vs. PR+CR.

32. A method comprising:
(a) annotating a region of interest (ROI) on a digital image of a test sample of a tumor, wherein said digital image is a digital image of a sample multiplex affinity stained for PD-L1, CD8, CD3, CD68 and an epithelial marker (EM⁻) (panel 1);
(b) extracting from the ROI one or more feature metrics of Table 4, left column; and
(c) applying a scoring function obtained by the method of claim 29 to a feature vector comprising the feature(s) of (b).

33. The method of claim 32, wherein the ROI is annotated in a digital image of a first serial section of the test sample, wherein the first serial section is stained with hematoxylin and eosin, and wherein the ROI is automatically registered to a digital image of at least a second serial section of the test sample, wherein the second serial section is stained with panel 1.

34. A method comprising:
(a) annotating a region of interest (ROI) on a digital image of a test sample of a tumor, wherein said digital image is a digital image of a sample multiplex affinity stained for PD-L1, PD-1, CD8, LAG3, and an epithelial marker (panel 2);
(b) extracting from the ROI one or more feature metrics of Table 4, right column; and
(c) applying a scoring function obtained by the method of claim 29 to a feature vector comprising the feature(s) of (b).

35. The method of claim 34, wherein the ROI is identified in a digital image of a first serial section of the test sample, wherein the first serial section is stained with hematoxylin and eosin, and wherein the ROI is automatically registered to a digital image of at least a second serial section of the test sample, wherein the second serial section is stained with panel 2.

36. A system for predicting a response of a patient to a PD-1 axis therapy, the system comprising: a processor; and a memory coupled to the processor, the memory to store computer executable instructions that, when executed by the processor, cause the processor to perform operations comprising one or more methods of claim 1.

37. The system of claim 36, further comprising a scanner or microscope adapted to capture a digital image of a section of the tissue sample and to communicate the image to the computer apparatus.

38. The system of claim 36, wherein the system further comprises an automated slide stainer programmed to histochemically stain a section of the tissue sample with panel 1 or panel 2.

39. The system of claim 38, wherein the system further comprises an automated hematoxylin and eosin stainer programmed to stain one or more serial sections of the section stained by the automated slide stainer.

40. The system of claim 36, the system further comprising a laboratory information system (LIS) for tracking sample and image workflow and diagnostic information, the LIS comprising a central database configured to receive and store information related to the tissue sample, the information comprising at least one of the following: processing steps to be carried out on the tumor tissue sample, processing steps to be carried out on digital images of sections of the tumor tissue sample, processing history of the tumor tissue sample and digital images; and one or more clinical variables relevant to likelihood that the patient will respond to the therapy (such as MMR or MSI status).

41. A non-transitory computer readable storage medium for storing computer-executable instructions that are executed by a processor to perform operations, the operations comprising the method of claim 1.

42. A method of treating a patient having a tumor, said method comprising identifying a level of a feature of the tumor indicative that the tumor is likely to respond to the PD-1 axis directed therapy, and administering to the patient the PD-1 axis directed therapy, wherein the feature is selected from the group consisting of:
(a) ratio between a number of stromal PD-L1$^+$/CD3$^+$ cells and the total number of stromal CD3$^+$ cells,
(b) ratio between a number of stromal PD-L1$^+$/CD8$^+$ cells and the total number of stromal CD8$^+$ cells,
(c) ratio between a number of stromal PD-L1$^+$/CD68$^+$ cells and the total number of stromal CD68$^+$ cells, and
(d) ratio between number of stromal PD-L1$^+$/CD3$^+$/CD8$^-$ cells and the total number of stromal CD3+CD8$^-$ cells
(e) mean distance between epithelial CD8$^+$ cells and the closest PD-L1$^+$/CD68$^+$ cell,
(f) density epithelial PD-L1$^+$/CD3$^+$/CD8$^-$ cells,
(g) ratio between number of epithelial PD-L1$^+$/CD3$^+$ cells the total number of epithelial CD3$^+$ cells,
(h) ratio between number of epithelial PD-L1$^+$/CD8$^+$ cells in the EM$^+$ ROI OR tumor ROI and the total number of epithelial CD8$^+$ cells in the EM$^+$ ROI OR tumor ROI,
(i) ratio between number of epithelial PD-L1$^+$/CD68$^+$ cells in the ROI and the total number of epithelial CD68$^+$ cells in the ROI,
(j) ratio between number of epithelial PD-L1$^+$/CD3$^+$/CD8$^-$ cells in the ROI and the total number of epithelial CD3$^+$/CD8$^-$ cells in the ROI,
(k) ratio between number of epithelial CD3$^+$/CD8$^-$ cells in the EM$^+$ ROI OR tumor ROI and the total number of epithelial CD3$^+$ cells in the EM$^+$ ROI OR tumor ROI,
(l) max number of PD-1$_{Low}$/CD8$^+$ within a 20 μm radius of PD-L1$^+$/CD8$^+$ cells,
(m) max value of CD8$^+$ cell PD-L1 intensity,
(n) ratio of number of PD-1$^+$/PD-L1/Lag3$^+$/CD8$^+$ cells to CD8$^+$ cells in epithelial area,
(o) spatial variance number of PD-1$^+$ cells within 20 μm radius of PD-L1$^+$ cells,
(p) max value of all cell PD-L1 intensity,
(q) number of Lag3 positive cells in EM$^+$ ROI,
(r) density of PD-L1$^+$/EM cells in EM$^-$ ROI,
(s) Number of PD-L1$^+$ cells in EM$^+$ ROI,
(t) Number of PD-L1$^+$ cells in EM$^-$ ROI,
(u) Number of PD-1$^+$ cells in EM$^-$ ROI,
(v) max number of PD-1$_{Low}$/CD8$^+$ cells within 20 μm radius of PD-L1$^+$ cell,
(w) mean number of PD-1$_{Low}$/CD8$^+$ cells within 20 μm radius of PD-L1$^+$ cell,
(x) max value Lag3 intensity from CD8$^+$Lag3$^+$ cells,
(y) Number of CD8$^+$ cells in EM$^+$ ROI,
(z) Variance in number of PD-1$_{Low}$/CD8$^+$ cells within 20 μm radius of PD-L1$^+$/CD8$^+$ cells,
(aa) Average distance from PD-L1$^+$ cells to its nearest PD-1$^+$ cell,
(bb) max number of PD-1$_{Low}$/CD8$^+$ cells within 20 μm radius of PD-L1$^+$/EM$^+$ cell,
(cc) Standard deviation of distance from PD-L1$^+$ cells to its nearest PD-1$^+$ cell,
(dd) Ratio of number of Lag3$^+$/CD8$^+$ cells to number of CD8$^+$ cells in EM$^+$ ROI,
(ee) Ratio of number of PD-L1$^+$/CD8$^+$ cells to number of CD8$^+$ cells in EM$^+$ ROI,
(ff) Mean number of PD-1$_{Low}$/CD8$^+$ cells within 10 μm radius of PD-L1$^+$ cells,
(gg) Variance in number of PD-1$_{Low}$/CD8$^+$ cells within 10 μm radius of PD-L1$^+$ cells,
(hh) Mean value of PD-1 intensity from all PD-1$^+$ cells,
(ii) Min value of Lag3 intensity from all Lag3$^+$ cells,
(jj) Density of PD-L1$^+$/EM$^+$ cells in EM$^+$ ROI,
(kk) max number of PD-1$_{Low}$/CD8$^+$ within 10 μm radius of PD-L1$^+$ cell,
(ll) Number of PD-1$^+$ cells in EM$^+$ ROI,
(mm) ratio of number of PD-1$^+$/PD-L1$^-$/Lag3$^+$/CD8$^+$ cells to CD8$^+$ cells in EM$^-$ ROI,
(nn) Max value of Lag3 intensity from CD8$^+$/Lag3$^+$ cells,
(oo) Ratio of number of Lag3$^+$/CD8$^+$ cells to number of CD8$^+$ cells in EM$^-$ ROI, and
(pp) number of Lag3 positive cells in EM$^+$ ROI.

43. A method of treating a patient having a tumor, said method comprising identifying a level of a feature of the tumor indicative that the tumor is likely to respond to the PD-1 axis directed therapy, and administering to the patient the PD-1 axis directed therapy, wherein the feature is selected from the group consisting of:
- (a) ratio of the number of Lag3$^+$/CD8$^+$ cells to total CD8$^+$ cells in panCK-negative area;
- (b) ratio of number of Lag3$^-$/CD8$^+$ cells to CD8$^+$ cells in panCK-negative area,
- (c) number of Lag3$^+$/panCK$^-$ cells divided by panCK-negative area,
- (d) number of Lag3 positive cells in panCK negative area,
- (e) max value of Lag3 intensity in CD8$^+$ cells,
- (f) number of Lag3$^+$ cells in panCK-positive area,
- (g) mean number of PD-1$_{med}$/CD8$^+$ cells within a 10 μm radius of PD-L1$^+$/panCK+ cell,
- (h) mean number of PD-1$_{med}$/CD8$^+$ cells within a 20 μm radius of PD-L1$^+$/panCK+ cell,
- (i) variance of the number of PD-1$_{med}$/CD8$^+$ cells within a 20 μm radius of PD-L1$^+$/CD8$^+$ cell,
- (j) variance of the number of PD-1$_{med}$/CD8$^+$ cells within a 20 μm radius of PD-L1$^+$/panCK$^+$ cell,
- (k) variance of the number of PD-1$_{Low}$/CD8$^+$ cells within a 10 μm radius of a PD-L1$^+$ cell,
- (l) max number of PD-1$_{med}$/CD8$^+$ cells within a 20 μm radius of a PD-L1$^+$/CD8$^+$ cell, and
- (m) max number of PD-1$_{med}$/CD8$^+$ cells within a 20 μm radius of a PD-L1$^+$ cell.

* * * * *